United States Patent
Dillingham

(10) Patent No.: US 8,845,755 B2
(45) Date of Patent: Sep. 30, 2014

(54) MODULAR PROSTHETIC DEVICES AND PROSTHESIS SYSTEM

(71) Applicant: iFIT Prosthetics, LLC, Pewaukee, WI (US)

(72) Inventor: Timothy R. Dillingham, Merion Station, PA (US)

(73) Assignee: iFit Prosthetics, LLC, Pewaukee, WI (US)

( * ) Notice: Subject to any disclaimer, the term of this patent is extended or adjusted under 35 U.S.C. 154(b) by 0 days.

(21) Appl. No.: 14/050,739

(22) Filed: Oct. 10, 2013

(65) Prior Publication Data

US 2014/0039644 A1  Feb. 6, 2014

Related U.S. Application Data

(63) Continuation-in-part of application No. 13/274,146, filed on Oct. 14, 2011, now abandoned, which is a continuation-in-part of application No. 13/083,403, filed on Apr. 8, 2011, now Pat. No. 8,491,667, and a continuation-in-part of application No. 13/274,130, filed on Oct. 14, 2011, now Pat. No. 8,470,050.

(51) Int. Cl.
| | | |
|---|---|---|
| *A61F 2/62* | (2006.01) | |
| *A61F 2/76* | (2006.01) | |
| *A61F 2/78* | (2006.01) | |
| *A61F 2/80* | (2006.01) | |
| *F16C 11/10* | (2006.01) | |
| *A61F 2/64* | (2006.01) | |
| *A61F 2/60* | (2006.01) | |
| *A61F 2/54* | (2006.01) | |
| *A61F 2/50* | (2006.01) | |

(52) U.S. Cl.
CPC ... *A61F 2/64* (2013.01); *A61F 2/78* (2013.01); *F16C 11/106* (2013.01); *A61F 2/60* (2013.01); *A61F 2/601* (2013.01); *A61F 2/76* (2013.01); *A61F 2/7812* (2013.01); *A61F 2/80* (2013.01); *A61F 2002/5018* (2013.01); *A61F 2002/502* (2013.01); *A61F 2002/5026* (2013.01); *A61F 2002/608* (2013.01); *A61F 2002/7862* (2013.01); *A61F 2002/7881* (2013.01); *A61F 2/54* (2013.01); *A61F 2002/5023* (2013.01); *A61F 2002/5027* (2013.01); *A61F 2002/546* (2013.01); *A61F 2002/785* (2013.01); *A61F 2002/7875* (2013.01)

USPC .................................. 623/38; 403/87

(58) Field of Classification Search
CPC ................... A61F 2002/5018; F16C 11/106
USPC .................................. 623/38; 403/87
See application file for complete search history.

(56) References Cited

U.S. PATENT DOCUMENTS

| 1,090,881 A | 3/1914 | Rowley |
|---|---|---|
| 4,161,042 A | 7/1979 | Cottingham et al. |

(Continued)

FOREIGN PATENT DOCUMENTS

| EP | 0395630 B1 | 10/1993 |
|---|---|---|
| EP | 1656911 A1 | 5/2006 |

(Continued)

OTHER PUBLICATIONS

Office Action issued on Feb. 22, 2013 in related U.S. Appl. No. 13/083,403.

(Continued)

*Primary Examiner* — David H Willse
(74) *Attorney, Agent, or Firm* — Caesar, Rivise, Bernstein, Cohen & Pokotilow, Ltd.

(57) ABSTRACT

An adjustable prosthesis system for a residual limb includes: an adjustable outer shell having an adjustable inner volume and an adjustable inner shape; at least one closure component attached to the adjustable outer shell and adapted to adjust at least one of the adjustable inner volume and the adjustable inner shape of the adjustable outer shell; an inner liner adapted to receive the residual limb and to be inserted in the adjustable inner volume of the adjustable outer shell; and an adjustable connector having a proximal end adjustably connected to a distal end of the adjustable outer shell and adapted to provide concurrently for a plurality of directional adjustments and/or angular adjustments of a position of the distal end of the adjustable outer shell relative to the proximal end of the adjustable connector, a distal end of the adjustable connector being adapted to connect to a prosthetic device.

21 Claims, 31 Drawing Sheets

(56) References Cited

U.S. PATENT DOCUMENTS

| | | |
|---|---|---|
| 4,302,856 A | 12/1981 | May |
| 4,872,879 A | 10/1989 | Shamp |
| 5,314,497 A | 5/1994 | Fay et al. |
| 5,425,782 A | 6/1995 | Phillips |
| 5,443,526 A | 8/1995 | Hoerner |
| 5,529,575 A | 6/1996 | Klotz |
| 5,571,209 A | 11/1996 | Brown, Sr. |
| 5,651,792 A | 7/1997 | Telikicherla |
| 5,728,165 A | 3/1998 | Brown, Sr. |
| 5,728,170 A | 3/1998 | Becker et al. |
| 5,888,233 A | 3/1999 | Randstrom |
| 5,888,234 A | 3/1999 | Littig |
| 5,941,912 A | 8/1999 | Taylor et al. |
| 6,051,026 A | 4/2000 | Biedermann et al. |
| 6,267,787 B1 | 7/2001 | Capper et al. |
| 6,368,357 B1 | 4/2002 | Schon et al. |
| 6,398,817 B1 | 6/2002 | Hellberg et al. |
| 6,402,789 B1 | 6/2002 | Gramnas |
| 6,576,022 B2 | 6/2003 | Meyer et al. |
| 6,689,171 B2 | 2/2004 | Slemker et al. |
| 6,797,008 B1 * | 9/2004 | Arbogast et al. ............... 623/34 |
| 6,942,703 B2 | 9/2005 | Carstens |
| 6,991,657 B1 | 1/2006 | Price, Jr. |
| 7,083,654 B2 | 8/2006 | Helenberger et al. |
| D617,460 S | 6/2010 | Okuda et al. |
| 7,867,286 B2 | 1/2011 | Einarsson |
| 2002/0116789 A1 | 8/2002 | McDevitt |
| 2003/0023320 A1 | 1/2003 | Laghi |
| 2003/0065403 A1 | 4/2003 | Meyer et al. |
| 2003/0233151 A1 | 12/2003 | Lund |
| 2005/0271462 A1 | 12/2005 | Curtis |
| 2005/0278038 A1 | 12/2005 | Ikeda |
| 2007/0260328 A1 | 11/2007 | Bertels et al. |
| 2009/0043402 A1 | 2/2009 | Slemker |
| 2010/0036505 A1 | 2/2010 | Hassler |
| 2010/0274364 A1 | 10/2010 | Pacanowsky et al. |
| 2011/0015761 A1 | 1/2011 | Celebi et al. |
| 2011/0071647 A1 | 3/2011 | Mahon |

FOREIGN PATENT DOCUMENTS

| | | |
|---|---|---|
| GB | 2169207 A | 7/1986 |
| GB | 2274994 A | 8/1994 |
| JP | 08089519 A | 4/1996 |
| RU | 2088182 C1 | 8/1997 |
| WO | 98/43559 A1 | 10/1998 |
| WO | 2006/103430 A1 | 10/2006 |

OTHER PUBLICATIONS

Notice of Allowance issued Apr. 15, 2013 in related U.S. Appl. No. 13/083,403.

Written Opinion and International Search Report issued Mar. 29, 2013 in corresponding International Patent Application No. PCT/US2012/060168.

Written Opinion and International Search Report issued Mar. 15, 2013 in related International Patent Application No. PCT/US2012/060166.

JP 7-155343 A (Jun. 20, 1995) English language translation.

Office Action issued Apr. 16, 2013 in related U.S. Appl. No. 13/274,146.

Office Action issued on Aug. 29, 2013 in related U.S. Appl. No. 13/274,146.

* cited by examiner

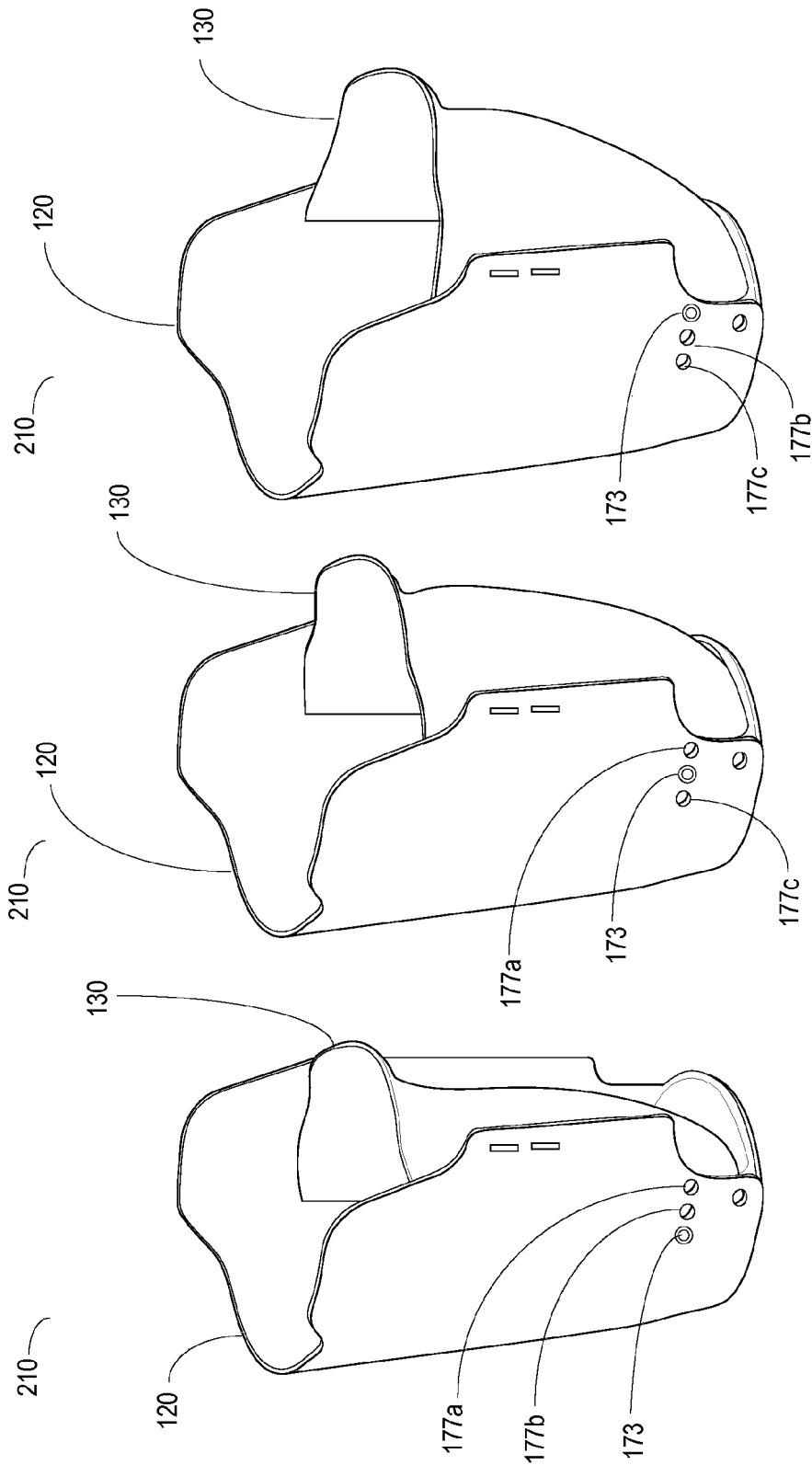

MODULAR PROSTHETIC DEVICES AND PROSTHESIS SYSTEM

CROSS-REFERENCE TO RELATED APPLICATIONS

This application is a continuation-in-part of U.S. patent application Ser. No. 13/274,146, entitled "Above-the Knee Modular Prosthesis System," filed on Oct. 14, 2011, now abandoned, which is a continuation-in-part of U.S. patent application Ser. No. 13/083,403 entitled "Modular Prosthesis System," filed on Apr. 8, 2011, now U.S. Pat. No. 8,491,667, and U.S. patent application Ser. No. 13/274,130, entitled "Rapid Fit Modular Prosthetic Device for Accommodating Gait Alignment and Residual Limb Shape and Volume," filed on Oct. 14, 2011, now U.S. Pat. No. 8,470,050, which is a continuation-in-part of U.S. patent application Ser. No. 13/083,403 entitled "Modular Prosthesis System," filed on Apr. 8, 2011, now U.S. Pat. No. 8,491,667, the entire disclosures of which are hereby expressly incorporated by reference herein, and this application claims priority benefit of each and all of the aforesaid earlier filed patent applications.

STATEMENT REGARDING FEDERALLY SPONSORED RESEARCH OR DEVELOPMENT

This invention(s) was made with government support under NIH Grant 2R42HD069067-02 awarded by the National Institutes of Health. The government has certain rights in the invention(s).

FIELD OF INVENTION

The present invention(s) relates to the field of prostheses, and more particularly to modular prosthetic devices and prosthesis systems which accommodate gait alignment and residual limb shape and volume.

BRIEF DESCRIPTION OF THE DRAWINGS

Applicant's systems and devices will be described by way of example with reference to the accompanying drawings, in which:

FIGS. 17a, 17b, 17c illustrate the adjustability of an exemplary embodiment of a rear limb engaging member for a rapid fit modular prosthetic device for accommodating gait alignment and residual limb shape and volume.

GLOSSARY

Figure 1:
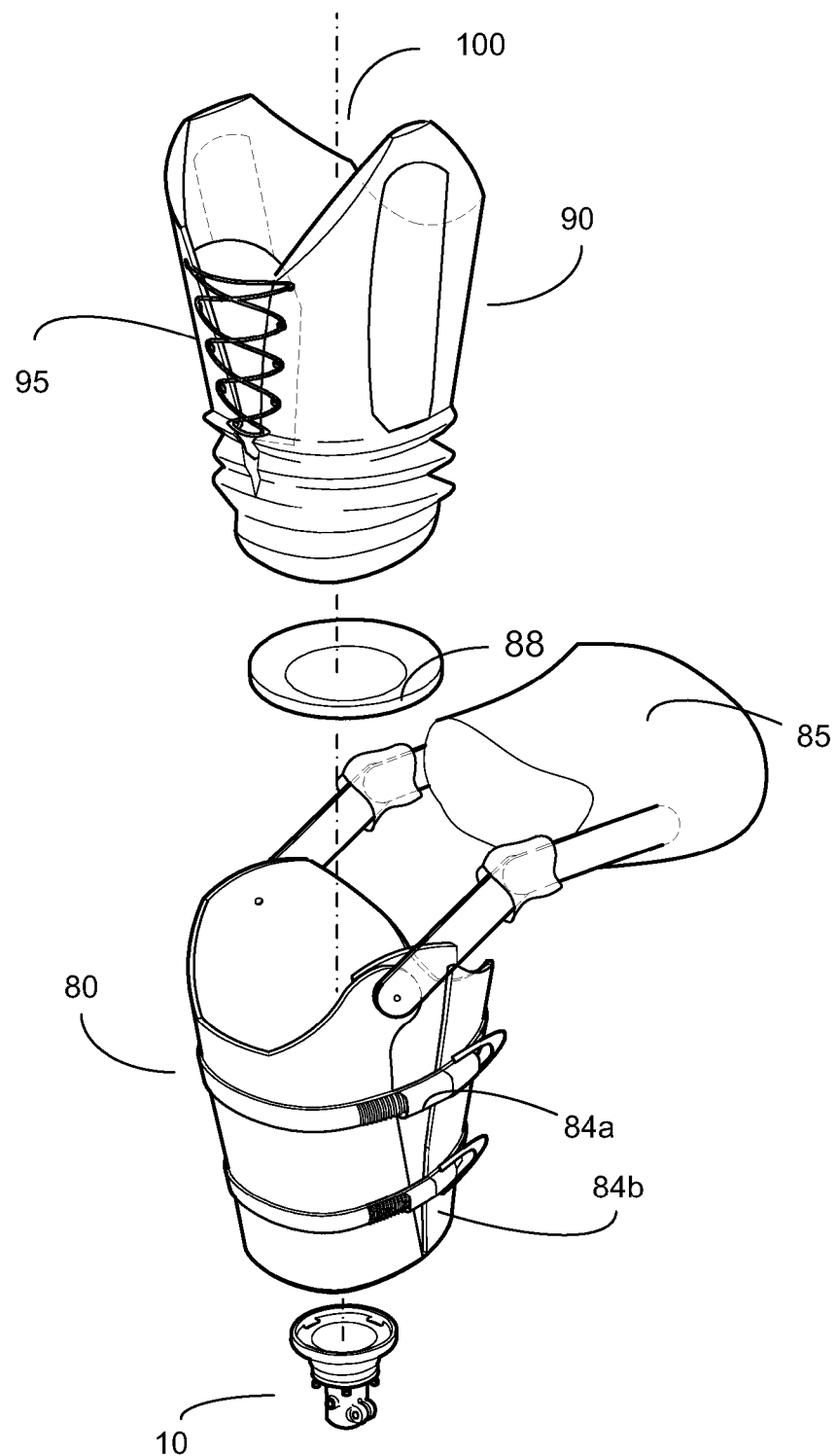
FIG. 1 illustrates an exploded view of an exemplary embodiment of a modular prosthesis system.

As used herein, the term "closure component" refers to any component which adjusts for the circumference of a residual limb to secure an outer housing.

As used herein, the term "connector tube" refers to any off-the-shelf 27-50 millimeter tube known in the art for use with a prosthetic limb, such as SAFETY KNEE.

As used herein, the term "deformable" means any structure with accommodating features for comfort and/or to reduce impact. Deformable materials may include, but are not limited to, padding, foam, cushioning, gel, rubber and any other malleable, moldable or adjustable material or combinations of materials known in the art.

As used herein, the term "dynamic stress point profile" refers to the unique anatomic and physiologic characteristics of an amputee's residual limb which govern the distribution of forces and stresses on the residual limb during activity.

As used herein, the term "flexible" means able to bend repeatedly without damage or breaking.

As used herein, the term "gait" means an individual's walking pattern, including all forces which could impact a residual limb.

As used herein, the term "grid pattern" refers to a configuration of uniformly repeating shapes arranged in a network of uniformly spaced horizontal and perpendicular lines.

As used herein, the term "modular" refers to components that are interchangeable and designed to function together as a unit. Components of a modular prosthesis system may be off-the-shelf or custom-made.

As used herein, the term "modular prosthesis system" refers to a prosthesis system comprised of components that are interchangeable and designed to function together as a unit. Components of a modular prosthesis system may be off-the-shelf or custom-made.

As used herein, the term "off-the-shelf knee joint" refers to a standard connector tube type prosthetic knee joint having an approximately 30 millimeter pipe which is commercially available. An off-the-shelf knee joint may be a low-cost foot and knee joint component known in the art that only needs to be adjusted for height.

As used herein, the term "pivotal side joints" refers to components of a suspension system that allow an amputee to bend his or her knee while wearing the prosthesis. Pivotal side joints may be comprised of one or more straight, curved, or irregular-shaped components. The components of a multi-component pivotal side joint are connected at a pivot point, the location of which may vary.

As used herein, the term "shank" refers to a component, such as a tubular component, attached to a connector or knee mechanism at one end and to another component, such as a prosthetic foot, at the other end.

As used herein, the term "supporting component" refers to a component which provides additional foundation for bearing the weight of a central plate and an upper assembly of a connector as well as the weight of an amputee.

As used herein, the term "washer" refers to a component which distributes pressure from another component and provides a firm attachment through friction to prevent movement of the component. For example, a washer placed under a threaded fastener will distribute the pressure from the head of the fastener and prevent movement of the fastener.

BACKGROUND

Over 150,000 amputations occur in the United States annually. Amputations are rising in frequency due to diabetes and peripheral vascular disease. The transtibial level of amputation is the most frequently performed.

A transtibial amputation is an amputation of the lower limb below the knee. A transtibial prosthesis is an artificial limb that replaces the portion of the leg below the knee that is missing. The shape of the residual limb varies for each individual and generally requires a custom-fitted prosthesis. A custom-fitted prosthesis that is comfortable is difficult to fabricate and is costly.

The transfemoral (above knee) level of amputation is less common than the below knee (transtibial) level of limb loss, but results in the highest level of gait dysfunction and disability. Further, the transfemoral level is difficult to fit with a prosthetic socket due to redundant soft tissues and variable lengths and sizes of the residual limb.

A transfemoral prosthesis is an artificial limb that replaces the portion of the leg above the knee that is missing. The shape of the residual limb varies for each individual and generally requires a custom-fitted prosthesis. A comfortable custom-fitted prosthesis is difficult to fabricate and costly to provide using conventional manufacturing techniques.

The initial cost of a conventional prosthesis for a transtibial amputee typically ranges from about $6,000 to about $14,000. In addition, there are additional costs to ensure the comfort and functionality of the device.

The initial cost of a conventional prosthesis for a transfemoral amputee typically ranges from $10,000 to $20,000 depending upon the components used and the difficulty in fitting the individual. In addition, there are additional costs to ensure the comfort and functionality of the device including replacement or revision of the socket.

Insurance coverage of such prosthetic devices is variable across insurers and has often impeded prescription and availability of high quality devices even for amputees with insurance coverage. The uninsured often go without comfortable prosthetic devices for long periods of time before public insurance enables them to receive a functional prosthesis.

The present state of prosthesis fabrication often requires three or more visits to the prosthetist and there are multiple steps in the fabrication process. First, a cast mold of the residual limb is made and a positive cast that resembles the residual limb is generated. Then, a prosthetic socket is built to custom-fit over the positive cast. Sometimes a check or temporary socket is made to insure a better fit. Typical fabrication techniques require specialized facilities. Generally, the final prosthesis requires post-fabrication adjustments as the residual limb tissue changes over time.

Recent advancements have been made in the field of prosthetic devices. However, devices such as computerized knee mechanisms and energy storing feet are costly and beyond the economic means of many prosthetic users, particularly those in nations outside the United States.

Attempts have been made in the prior art to develop prosthesis systems that can be globally manufactured and distributed. These prosthesis systems, however, have several limitations. They are difficult to fabricate and require specialized facilities for initial manufacturing (e.g., casting) and subsequent adjustments. These systems all require expertise and consulting support that is not widely available. In particular, the socket (i.e., the portion of the prosthesis into which the residual limb fits), socket attachment, and alignment aspects of the device seem to be a common problematic area of development.

It is desirable to create a prosthetic device which eliminates the need for complex fabrication and specialized tools or labs, and which can be economically manufactured and distributed on a global basis.

It is desirable to create a prosthetic device which is immediately fit and aligned on the residual limb during the initial clinical visit and is adjustable and modular to accommodate different residual limb sizes and volume fluctuations that frequently occur in patients after amputation or those with heart failure and renal diseases.

It is desirable to create a prosthetic device which is one size and adjustable to fit many shapes.

BRIEF SUMMARY

There are various aspects of Applicant's system, and many variations of each aspect.

One aspect is an adjustable prosthesis system for a residual limb. The system includes an adjustable outer shell, at least one closure component, an inner liner, and an adjustable connector. The adjustable outer shell has an adjustable inner volume and an adjustable inner shape. The at least one closure component is attached to the adjustable outer shell and is adapted to adjust at least one of the adjustable inner volume and the adjustable inner shape of the adjustable outer shell. The inner liner is adapted to receive the residual limb and to be inserted in the adjustable inner volume of the adjustable outer shell. The adjustable connector has a proximal end adjustably connected to a distal end of the adjustable outer shell and is adapted to provide concurrently for a plurality of directional adjustments and/or angular adjustments of a position of the distal end of the adjustable outer shell relative to the proximal end of the adjustable connector. The distal end of the adjustable connector is adapted to connect to a shank or an other prosthetic device.

In a first variation of the adjustable prosthesis system, the adjustable outer shell includes a first limb engaging panel and a second limb engaging panel pivotally connected to a first limb engaging panel. In a variant of this variation, at least a portion of the first limb engaging panel is rigid and at least a portion of the second limb engaging panel is not rigid.

In another variation of the adjustable prosthesis system, the adjustable outer shell includes a first flap having a first extended end and a second flap opposite the first flap and having a second extended end. At least a portion of the first flap overlaps at least a portion of the second flap so that at least a portion of the first extended end is on top of the second flap and at least a portion of the second extended end is under the first flap. In a variant of this variation, the first flap has a lateral length that is longer than a lateral length of the second flap.

In another variation of the adjustable prosthesis system, the at least one closure component is selected from a group consisting of buttons, snaps, clasps, clips, elastic components, buckles, laces, ties, interlocking components, hook-and-loop fasteners, hook-and-eye fasteners, hook-shaped components, looped wires, straps, and combinations thereof.

In another variation of the adjustable prosthesis system, adjustment of the adjustable outer shell and adjustment of the adjustable connector provide for a custom-like fit on the residual limb of the adjustable prosthesis system accounting for differences in residual limb shape, circumference, volume, angle, general size, and other properties, as well as differences in gait, bone structure, and bone alignment among a plurality of amputees.

In another variation of the adjustable prosthesis system, at least a portion of the adjustable outer shell is rigid. In another variation, at least a portion of the inner liner is deformable.

In yet another variation of the adjustable prosthesis system, the adjustable connector is releasably attached to the adjustable outer shell.

In yet another variation of the adjustable prosthesis system, the directional adjustments are selected from a group consisting of a forward adjustment, a backward adjustment, a side-to-side adjustment, a rotational adjustment, and combinations thereof.

In still yet another variation of the adjustable prosthesis system, the adjustable connector includes an upper plate, a lower plate below the upper plate, and a plurality of fasteners. The upper plate is adapted to adjustably connect to the adjustable outer shell. The lower plate is adapted to adjustably connect to the upper plate and to a shank or an other prosthetic device. The fasteners adjustably connect the lower plate to the upper plate. There are several variants of this variation.

In one variant, at least one of the fasteners is a rocker bolt assembly. In another variant, at least a portion of a bottom surface of the upper plate is convex and at least a portion of an upper surface of the lower plate is concave and adapted to receive at least part of the convex portion of the bottom surface of the upper plate. In a third variant, at least a portion of a lower surface of the upper plate is textured and at least a portion of an upper surface of the lower plate is textured.

A second adjustable prosthesis system is similar to the first adjustable prosthesis system or any of the variations discussed above, but includes at least one stiffening member attached to at least a portion of the adjustable outer shell. A third adjustable prosthesis system is similar to the first adjustable prosthesis system or any of the variations discussed above, but includes a suspension system connected to the adjustable outer shell.

A fourth adjustable prosthesis system is similar to the first adjustable prosthesis system or any of the variations discussed above, but includes at least one adjustment component selected from a group consisting of a height adjustment component, a volume adjustment component, an angle adjustment component, a circumference component, and combinations thereof.

A fifth adjustable prosthesis system is similar to the first adjustable prosthesis system or any of the variations discussed above, but includes a pin suspension system with a locking pin. A variant of this variation includes a locking mechanism to lock and unlock the locking pin at a desired position. A variant of that variant includes a base plate adapted to guide the locking pin to a location adjacent the locking mechanism.

Another aspect is an adjustable prosthesis system for a residual limb. The system includes an adjustable flexible outer shell, at least one closure component attached to the adjustable flexible outer shell, an inner liner, and an adjustable connector. The adjustable flexible outer shell has an adjustable inner volume and an adjustable inner shape. The adjustable outer shell includes a first flap having a first extended end and a second flap opposite the first flap and having a second extended end. At least a portion of the first flap overlaps at least a portion of the second flap so that at least a portion of the first extended end is on top of the second flap and at least a portion of the second extended end is under the first flap. The at least one closure component is attached to the adjustable flexible outer shell and is adapted to adjust at least one of the adjustable inner volume and the adjustable inner shape of the adjustable flexible outer shell. The inner liner is adapted to receive the residual limb and to be inserted in the adjustable inner volume of the adjustable flexible outer shell. The adjustable connector has a proximal end adjustably connected to a distal end of the adjustable flexible outer shell and is adapted to provide concurrently for a plurality of directional adjustments and/or angular adjustments of a position of the distal end of the adjustable flexible outer shell relative to the proximal end of the adjustable connector. A distal end of the adjustable connector is adapted to connect to a shank or an other prosthetic device. The adjustable connector includes an upper plate, a lower plate below the upper plate, and a plurality of rocker bolt assemblies. The upper plate is adapted to adjustably connect to the adjustable flexible outer shell. The lower plate is adapted to adjustably connect to the upper plate and to a shank or an other prosthetic device. The rocker bolt assemblies adjustably connect the lower plate to the upper plate, wherein at least a portion of a bottom surface of the upper plate is convex and at least a portion of an upper surface of a lower surface is concave and adapted to receive at least part of the convex portion of the bottom surface of the upper plate. Each rocker bolt assembly has a hollow threaded socket that extends downward through one of a plurality of apertures in the bottom surface of the upper plate and further downward through a plurality of adjacent corresponding apertures in the upper surface of the lower plate. The hollow threaded socket is adapted to receive a threaded bolt. The directional adjustments are selected from a group consisting of a forward adjustment, a backward adjustment, a side-to-side adjustment, a rotational adjustment, and combinations thereof.

In a variation of this adjustable prosthesis system, the at least one closure component is selected from a group consisting of buttons, snaps, clasps, clips, elastic components, buckles, laces, ties, interlocking components, hook-and-loop fasteners, hook-and-eye fasteners, hook-shaped components, looped wires, straps, and combinations thereof.

Yet another aspect is an adjustable connector for a prosthesis system. The adjustable connector includes an upper plate, a lower plate below the upper plate, and a plurality of fasteners. The upper plate is adapted to adjustably connect to a component of the prosthesis system adjacent a residual limb. The lower plate is adapted to adjustably connect to the upper plate and to a shank or an other prosthetic device below the lower plate. The fasteners are adapted to adjustably connect the lower plate to the upper plate, thereby providing for an adjustable connection between the component of the prosthesis system adjacent the residual limb and the shank or an other prosthetic device. The adjustable connection provides for a concurrently made plurality of directional adjustments and/or angular adjustments of a position of the component of the prosthesis system relative to the shank or an other prosthetic device.

In a first variation of the adjustable connector, at least one of the fasteners is a rocker bolt assembly. In a variant of this variation, each rocker bolt assembly has a hollow threaded socket that extends downward through one of a plurality of apertures in the bottom surface of the upper plate and further downward through one of the plurality of adjacent corresponding apertures in the upper surface of the lower plate. The hollow threaded socket is adapted to receive a threaded bolt.

In another variation of the adjustable connector, at least a portion of a bottom surface of the upper plate is convex and at least a portion of an upper surface of the lower plate is concave and adapted to receive at least part of the convex portion of the bottom surface of the upper plate.

In another variation of the adjustable connector, at least a portion of the lower surface of the upper plate is textured and at least a portion of the upper surface of the lower plate is textured.

Yet another aspect is an adjustable connector for a prosthesis system. The adjustable connector includes an upper plate, a lower plate below the upper plate, and a plurality of rocker bolt assemblies. The upper plate is adapted to adjustably connect to a component of the prosthesis system adjacent a residual limb. The lower plate is adapted to adjustably connect to the upper plate and to a shank or an other prosthetic device below the lower plate. At least a portion of a bottom surface of the upper plate is convex and at least a portion of an upper surface of the lower plate is concave and adapted to receive at least part of the convex portion of the bottom surface of the upper plate. The rocker bolt assemblies are adapted to adjustably connect the lower plate to the upper plate, thereby providing for an adjustable connection between the component of the prosthesis system adjacent the residual limb and the shank or an other prosthetic device. The adjustable connection provides for a concurrently made plurality of directional adjustments and/or angular adjustments of a position of the component of the prosthesis system relative to the shank or an other prosthetic device. The directional adjustments are selected from a group consisting of a forward adjustment, a backward adjustment, a side-to-side adjustment, a rotational adjustment, and combinations thereof.

In a variation of the adjustable connector, each rocker bolt assembly has a hollow threaded socket that extends downward through one of a plurality of apertures in the bottom surface of the upper plate and further down through one of a plurality of adjacent corresponding apertures in the upper surface of the lower plate. A hollow threaded socket is adapted to receive a threaded bolt.

DETAILED DESCRIPTION

For the purpose of promoting an understanding of the present invention(s), references are made in the text to exemplary embodiments of modular prosthesis systems and of modular prosthetic devices for accommodating gait alignment and residual limb shape and volume, only some of which are described herein. It should be understood that no limitations on the scope of the invention(s) are intended by describing these exemplary embodiments. One of ordinary skill in the art will readily appreciate that alternate but functionally equivalent materials, components, and designs may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention(s).

It should be understood that the drawings are not necessarily to scale; instead, emphasis has been placed upon illustrating the principles of the invention(s). In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

Figure 10:
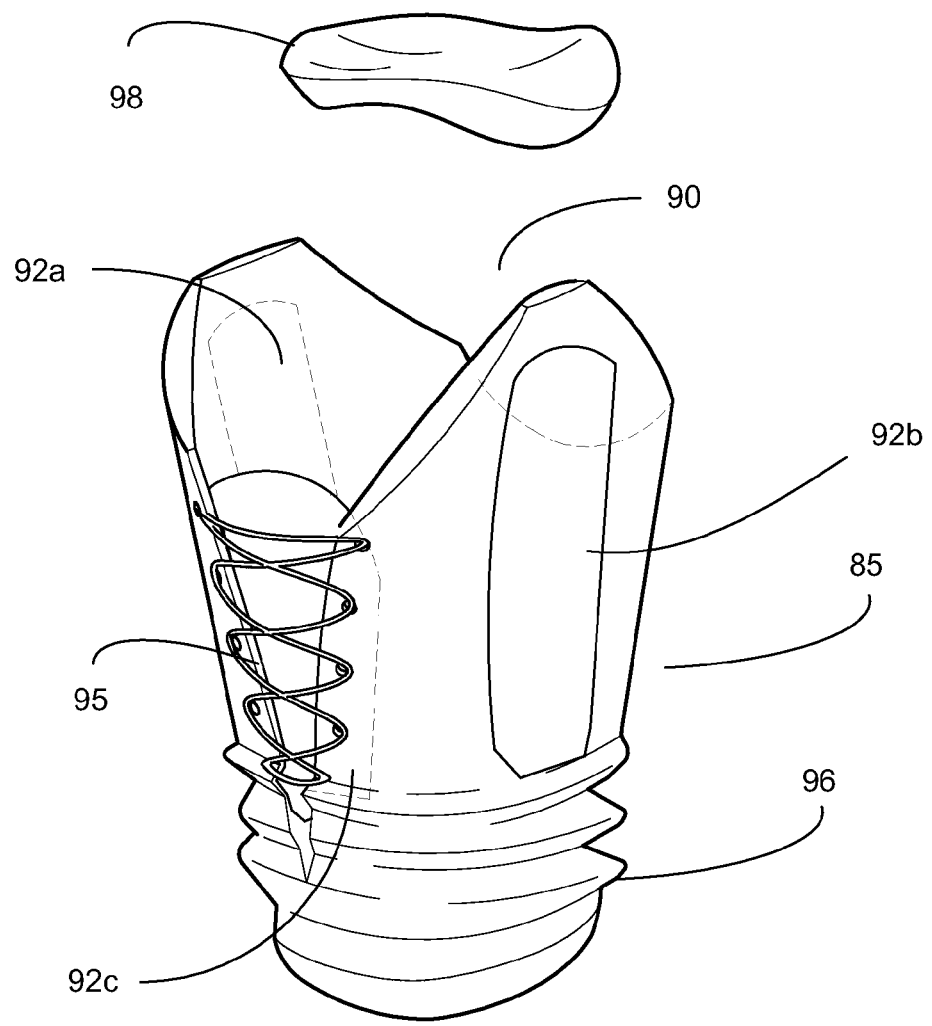
FIG. 10 illustrates a perspective view of an exemplary embodiment of a liner for a modular prosthesis system.
Figure 11:
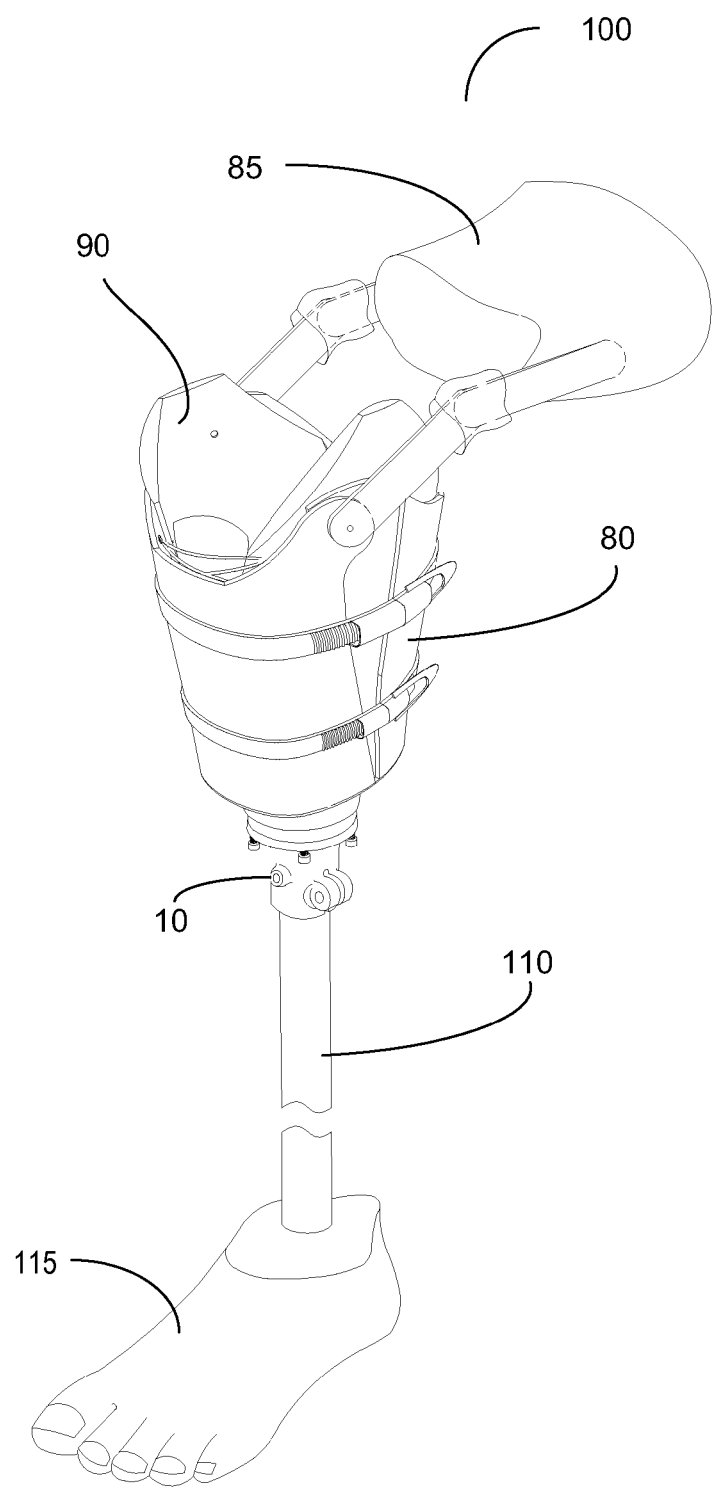
FIG. 11 illustrates a perspective view of an exemplary embodiment of an assembled modular prosthesis system.

FIG. 1 illustrates an exploded view of an exemplary embodiment of modular prosthesis system 100 comprised of connector 10, socket 80 with suspension system 85 (see FIGS. 9a and 9b), liner 90 (see FIG. 10), and shank 110 (see FIG. 11). In the embodiment shown, socket 80 and liner 90 include tightening components 84a, 84b and 95. Also visible in the embodiment shown is optional padding insert 88 which is placed at the bottom of socket 80 to support liner 90.

Figure 2:
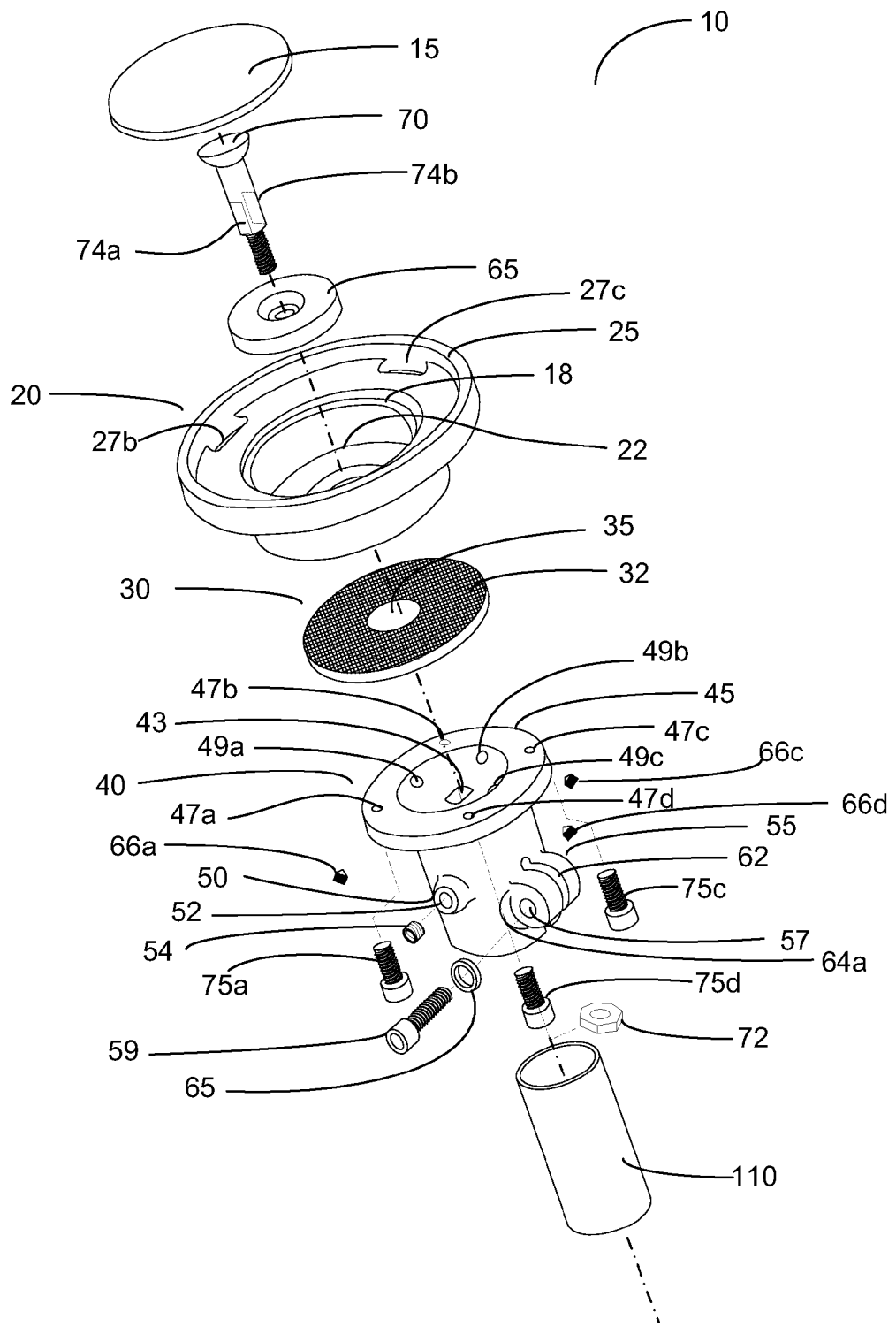
FIG. 2 illustrates an exploded view of an exemplary embodiment of a connector component for a modular prosthesis system.

FIG. 2 illustrates an exploded view of an exemplary embodiment of connector 10 for modular prosthesis system 100. In the embodiment shown, connector 10 is comprised of upper assembly 20, central plate 30, and lower assembly 40.

In the embodiment shown, upper assembly 20 is a tubular component with socket flange 25. Socket flange 25 is cup-shaped with a flat top surface. At the interface of socket flange 25 and the lower tubular portion of upper assembly 20 is ridge 18 for receiving and supporting cover 15. Socket flange 25 further includes apertures 27a, 27b, 27c, 27d (27a, 27d not visible) for inserting securing components 29a, 29b, 29c, 29d (not visible) used to secure connector 10 to socket 80. In the embodiment shown, apertures 27a, 27b, 27c, 27d are oval-shaped and are located near the edge of socket flange 25. In various other embodiments, apertures 27a, 27b, 27c, 27d are eliminated and socket 80 is secured to connector 10 in an alternate way. For example, one or more bolts or other fasteners may be threaded through apertures positioned on a substantially horizontal surface of upper assembly 20 and corresponding apertures on socket 80 (see FIG. 12).

In the embodiment shown, centered in the bottom of upper assembly 20 is aperture 22 for tapered shoulder screw 70. Aperture 22 is round and has a diameter that is substantially larger than the diameter of tapered shoulder screw 70 in this illustrated embodiment.

Central plate 30 is located between upper assembly 20 and lower assembly 40. The top surface of central plate 30 has raised grid pattern 32. In the embodiment shown, raised grid pattern 32 is uniform and has a plurality of raised protuberances in the shape of isosceles trapezoids (but other shapes may be used, and the grid pattern may be non-uniform). The bottom surface of upper assembly 20 has recessed grid pattern 28 (see FIGS. 3 and 4) that corresponds to raised grid pattern 32 on the top surface of central plate 30. Corresponding grid patterns 28, 32 on the bottom surface of upper assembly 20 and the top surface of central plate 30, respectively, allow for forward and backward adjustment and side-to-side adjustment.

In the embodiment shown, the bottom surface of central plate 30 has a rounded protuberance 37 (see FIG. 6) which corresponds to the shape of the upper surface of lower assembly 40. Central plate 30 further includes aperture 35 for tapered shoulder screw 70. In the embodiment shown, aperture 35 is round and has a diameter that is substantially larger than the diameter of the shank of tapered shoulder screw 70, but smaller than the diameter of aperture 22 in upper assembly 20.

In the embodiment shown, lower assembly 40 is a tubular component with central plate flange 45. The outer edge of the top surface of central plate flange 45 is flat, while the center portion of the top surface of central plate flange 45 is concave to accommodate rounded protuberance 37 of central plate 30.

The flattened portion of the top surface of central plate flange 45 includes a plurality of apertures 47a, 47b, 47c, 47d for central plate supporting components 75a, 75b, 75c, 75d (75b not visible). In the center of central plate flange 45 is aperture 43 for tapered shoulder screw 70. In the embodiment shown, aperture 43 is oval-shaped to accommodate and secure tapered shoulder screw 70.

In the embodiment shown, the outer edge of the concave portion on the top surface of central plate flange 45 further includes a plurality of apertures 49a, 49b, 49c, 49d (49d not visible) for insertion of set screws 66a, 66b, 66c, 66d (66b not visible). Apertures 49a, 49b, 49c, 49d pass completely through central plate flange 45 and set screws 66a, 66b, 66c, 66d help to firmly anchor connector 10 once the final position has been attained. In the embodiment shown, set screws 66a, 66b, 66c, 66d are cone point set screws; however, in other embodiments another type of set screw known in the art (e.g., domed point, cup point, dog point) may be used.

In the embodiment shown, upper assembly 20 further includes depressions 51a, 51b, 51c, 51d (see FIGS. 3 and 4) located on the top of the tubular portion of lower assembly 40 just under apertures 49a, 49b, 49c, 49d. Depressions 51a, 51b, 51c, 51d provide a space which allows a tool (e.g., a Hex driver) to be used to insert set screws 66a, 66b, 66c, 66d.

In addition, one side of tubular portion of lower assembly 40 further includes raised surface 50 which has aperture 52 for insertion of set screw 54. Aperture 52 passes completely through the side of lower assembly 40 and when set screw 54 is inserted, the end of set screw 54 crosses the plane of the inner surface of lower assembly 40 and bumps against shank 110. In the embodiment shown, the top of raised surface 50 is flat; however, in other embodiments, the top of raised surface 50 may have slight curvature, mimicking the contours of lower assembly 40. In the embodiment shown, set screw 54 is a cone point set screw.

In the embodiment shown, lower assembly 40 further includes protuberance 55 having apertures 57 for insertion of shank securing component 59. Protuberance 55 is rounded and extends perpendicularly outward from lower assembly 40. In the embodiment shown, lower assembly 40 further includes groove 62 which starts at the bottom of lower assembly 40 and extends to approximately the center of lower assembly 40, cutting protuberance 55 in half. In the embodiment shown, lower assembly 40 further includes depressions 64a, 64b (64b not visible) in lower assembly 40 on each side of protuberance 55. Depressions 64a, 64b provide a space which allows a tool (e.g., wrench, socket wrench) to be used to tighten shank securing component 59. Gap 62 allows flexibility for the clamp to squeeze around the shank 110.

In the embodiment shown, shank securing component 59 is comprised of a bolt and nut; the bolt is inserted through aperture 57 and the nut is threaded onto the end of the bolt and tightened, securing lower assembly 40 to shank 110 and preventing lower assembly 40 from rotating around shank 110.

In the embodiment shown, shank 110 has a diameter of 30 mm; however, in other embodiments, lower assembly 40 may be designed to accommodate shanks of varying diameters. In an exemplary embodiment, shank 110 will include a connector at the bottom which allows various types of feet known in the art, such as the SACH foot or the NIAGRA foot, to be connected to shank 110. In an exemplary embodiment, the length of shank 110 is adjustable, eliminating the need to cut shank 110 to a length sized for each amputee.

Tapered shoulder screw 70 is inserted through aperture 22 in upper assembly 20, aperture 35 in central plate 30, and aperture 43 in lower assembly 40. When tapered shoulder screw 70 is positioned, the threaded end of tapered shoulder screw 70 extends into lower assembly 40. Nut 72 is threaded onto the threaded end of tapered shoulder screw 70 and tightened, securing upper assembly 20, central plate 30, and lower assembly 40 together.

In the embodiment shown, nut 72 is a K-nut, that is, a nut with an attached, free-spinning washer. In the embodiment shown, the washer is an external star washer. The use of a K-nut provides maximum torsional resistance and prevents loosening caused by vibration.

In the embodiment shown, tapered shoulder screw 70 is inserted through washer 65 before tapered shoulder screw 70 is inserted through aperture 22 in upper assembly. Washer 65 has a larger diameter than aperture 22 covering aperture 22 and preventing tapered shoulder screw 70 from directly touching upper assembly 20. Washer 65 distributes the load of tapered shoulder screw 70.

In the embodiment shown, tapered shoulder screw 70 is a shoulder screw with a flat, tapered head and machined grooves 74a, 74b cut on opposite sides of tapered shoulder screw 70. Machined grooves 74a, 74b lock tapered shoulder screw 70 automatically into place inside oval-shaped aperture 43 in lower assembly 40, allowing tapered shoulder screw 70 to be tightened from one end.

In the embodiment shown, the bottom of washer 65 is flat while the top of washer 65 has a beveled outer edge. The edges of the aperture in the center of washer 65 are also beveled. The bevel angle is greater on the top of washer 65 to accommodate the tapered head of tapered shoulder screw 70. When washer 65 is used, only a small portion of the head of tapered shoulder screw 70 is visible above washer 65.

The large diameters (i.e., diameters substantially larger than the diameter of the shoulder of tapered shoulder screw 70) of aperture 22 in upper assembly 20 and aperture 35 in central plate 30, the oval shape of aperture 43 in lower assembly 40, rounded protuberance 37 of central plate 30 and corresponding concave center portion of top surface of lower assembly 40, and tapered shoulder screw 70 allow for angular adjustment of upper assembly 20 and central plate 30 in relationship to lower assembly 40. The ability to angularly adjust connector 10 allows connector 10 to accommodate various stump configurations, providing additional comfort to the amputee.

Once upper assembly 20, central plate 30, and lower assembly 40 are correctly positioned, nut 72 is tightened on tapered shoulder screw 70 and central plate supporting components 75a, 75b, 75c, 75d are inserted into apertures 47a, 47b, 47c, 47d from the bottom and are tightened until the ends of central plate supporting components 75a, 75b, 75c, 75d press against the bottom of central plate 30, supporting central plate 30 and upper assembly 20 and further securing upper assembly 20, central plate 30, and lower assembly 40 together.

Cover 15 is placed on upper assembly 20 so that it rests on ridge 18 of upper assembly 20, covering tapered shoulder screw 70 and washer 65. When cover 15 is positioned, the surface of cover 15 is flush with the inside surface of socket flange 25.

In the embodiment shown, cover 15 and ridge 18 are shown for ease of illustration. In various other embodiments, ridge 18 and cover 15 are omitted and the inner surface of socket flange 25 is a single piece.

In the embodiment shown, upper assembly 20, central plate 30, lower assembly 40, and cover 15 are comprised of polyphthalamide (i.e., PPA or high performance polyamide); however, in various other embodiments those components may be comprised of other thermoplastics/synthetic resins, such as nylon, acrylonitrile butadiene styrene (ABS), polypropylene, polyamide-imide, polybenzimidazole (PBI), polybutylene (PB-1) or combinations thereof, or any other suitable non-metal material.

Figure 3:
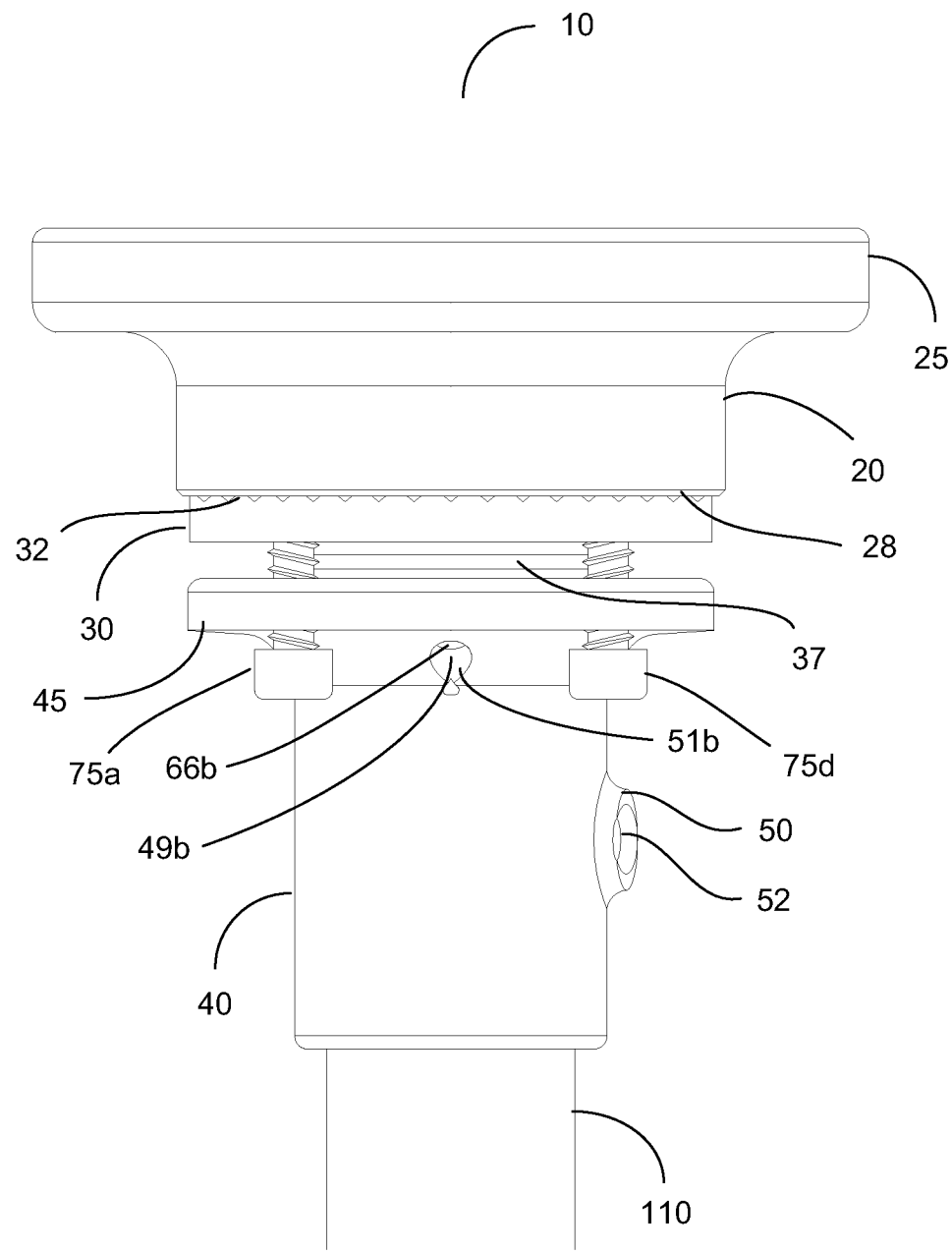
FIG. 3 illustrates a front view of an exemplary embodiment of a connector for a modular prosthesis system.

FIG. 3 illustrates a front view of an exemplary embodiment of connector 10 for modular prosthesis system 100. Visible in FIG. 3 are upper assembly 20, including socket flange 25 and recessed grid pattern 28; central plate 30, including raised grid pattern 32 and rounded protuberance 37; lower assembly 40, including central plate flange 45, aperture 49b, depression 51b, raised surface 50, and aperture 52; set screw 66b; central plate supporting components 75a, 75d; and shank 110.

Figure 4:
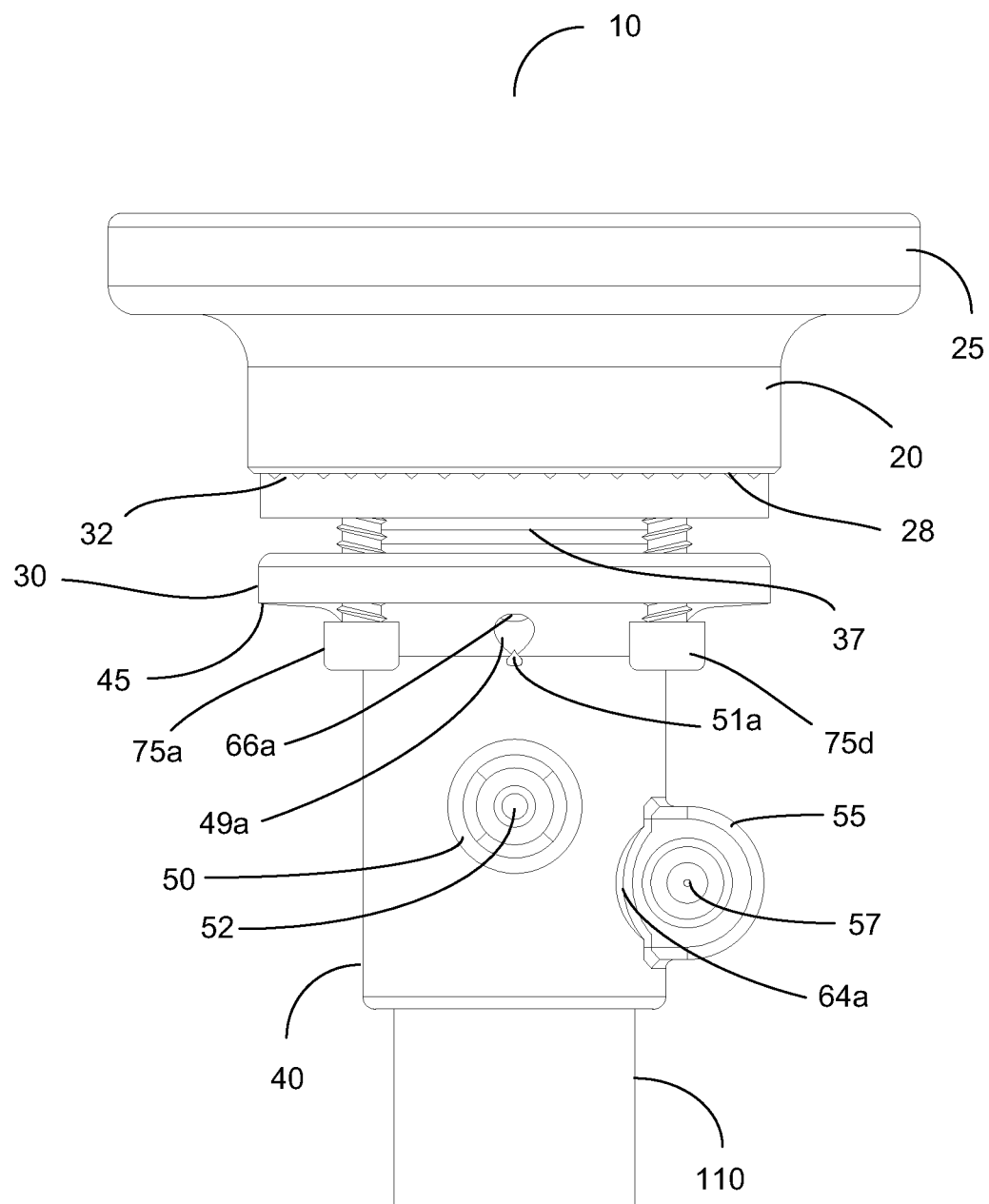
FIG. 4 illustrates a side view of an exemplary embodiment of a connector for a modular prosthesis system.

FIG. 4 illustrates a side view of an exemplary embodiment of connector 10 for modular prosthesis system 100. Visible in FIG. 4 are upper assembly 20, including socket flange 25 and recessed grid pattern 28; central plate 30, including raised grid pattern 32 and rounded protuberance 37; lower assembly 40, including central plate flange 45, aperture 49a, depression 51a, raised surface 50, aperture 52, protuberance 55, aperture 57, and depression 64a; set screw 66a; central plate supporting components 75a, 75d; and shank 110.

Figure 5:
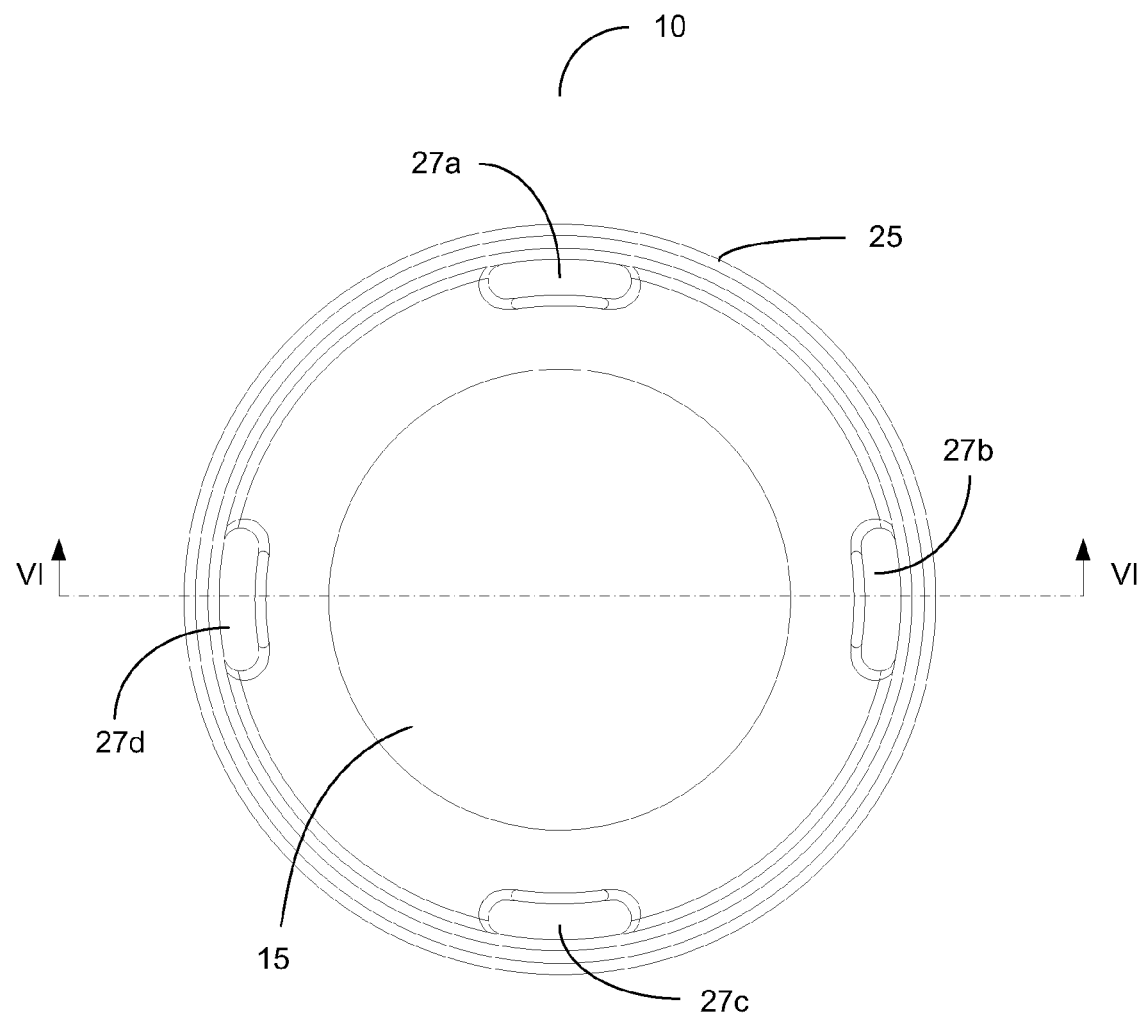
FIG. 5 illustrates a top view of an exemplary embodiment of a connector for a modular prosthesis system.

FIG. 5 illustrates a top view of an exemplary embodiment of connector 10 for modular prosthesis system 100. Visible in FIG. 5 are socket flange 25 of upper assembly 20, cover 15, and apertures 27a, 27b, 27c, 27d for securing components 29a, 29b, 29c, 29d (not visible), which are used to secure connector 10 to socket 80 (not visible).

Figure 6:
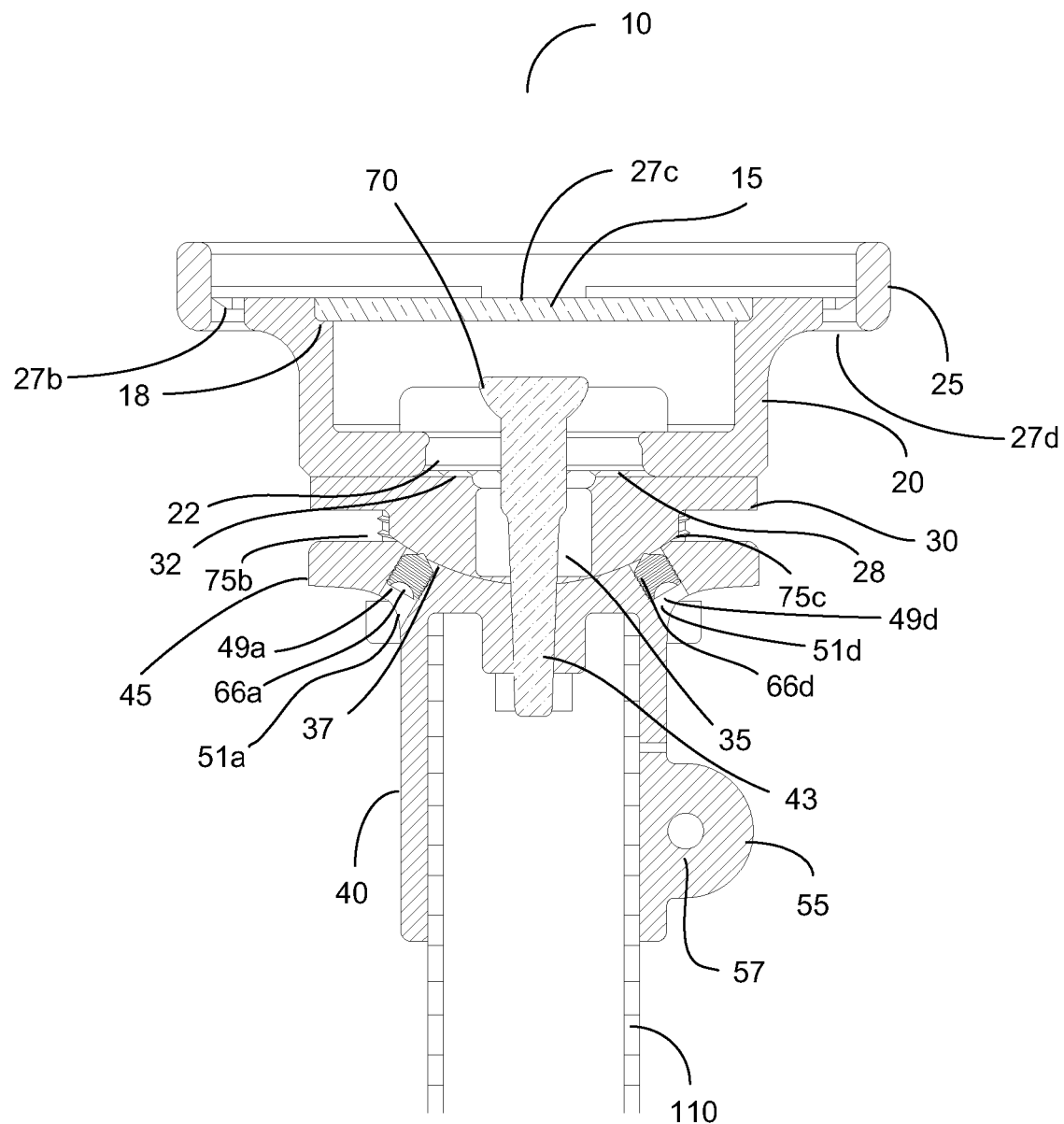
FIG. 6 illustrates a sectional view of an exemplary embodiment of a connector for a modular prosthesis system.

FIG. 6 illustrates a sectional view of an exemplary embodiment of connector 10 for modular prosthesis system 100 taken along line VI of FIG. 5. Visible in FIG. 6 are cover 15; upper assembly 20, including aperture 22, socket flange 25, recessed grid pattern 28, apertures 27b, 27c, 27d, and ridge 18; central plate 30, including aperture 35, raised grid pattern 32, and rounded protuberance 37; lower assembly 40, including aperture 43, central plate flange 45, aperture 49a, 49d, depression 51a, 51d, aperture 57, and protuberance 55; set screws 66a, 66d; central plate supporting components 75b, 75c; tapered shoulder screw 70, and shank 110.

Figure 7A:
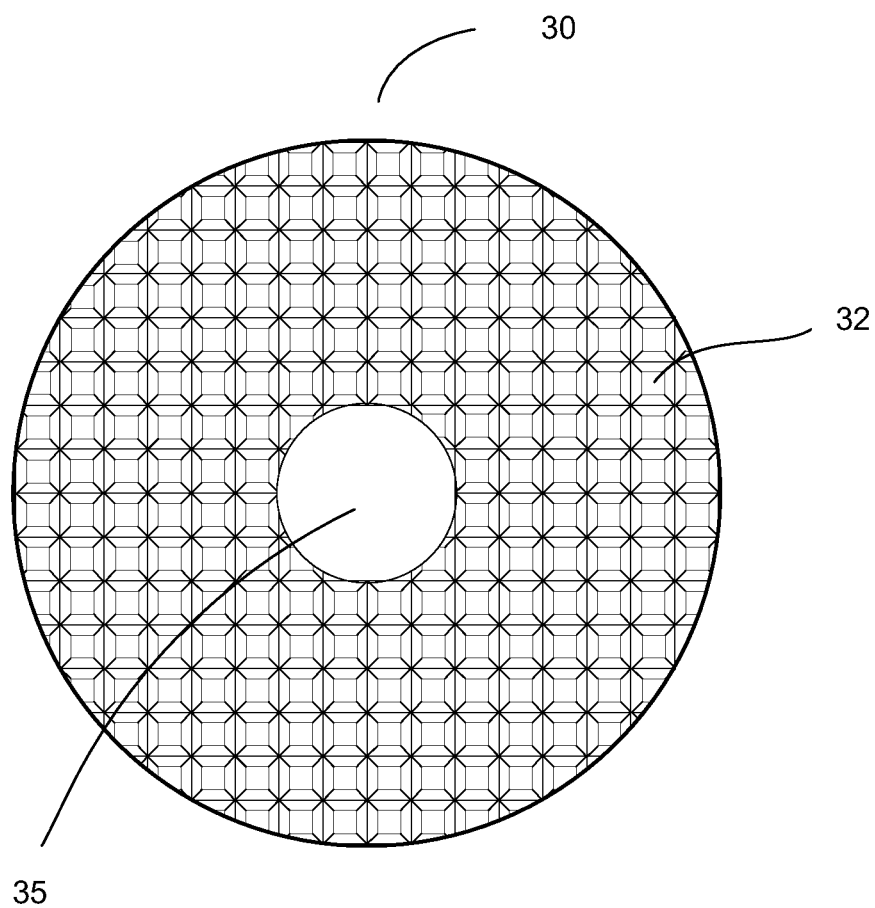
FIG. 7a illustrates a top view of an exemplary embodiment of a central plate of a connector.

FIG. 7a illustrates a top view of an exemplary embodiment of central plate 30 showing raised grid pattern 32 and aperture 35.

Figure 7B:
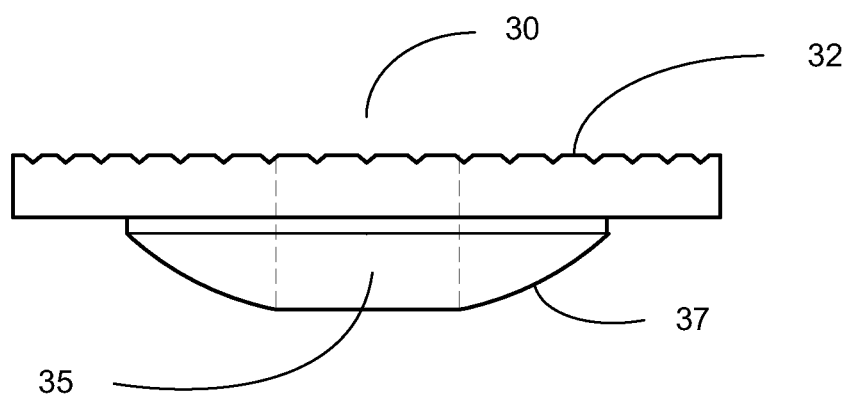
FIG. 7b illustrates a side view of an exemplary embodiment of a central plate of a connector.

FIG. 7b illustrates a side view of an exemplary embodiment of central plate 30 showing raised grid pattern 32, aperture 35, and rounded protuberance 37.

Figure 8A:
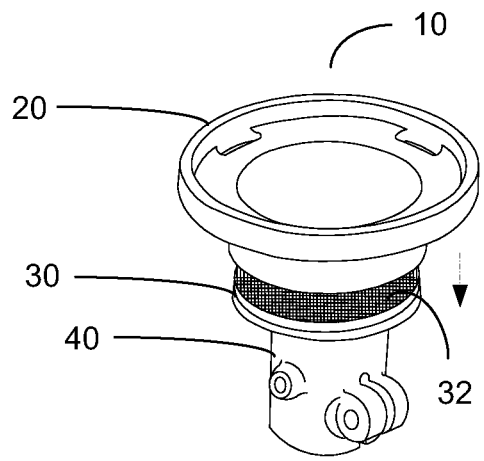
FIGS. 8a, 8b, and 8c illustrate front-back, side-to-side, and angular adjustment of an exemplary embodiment of a connector.
Figure 8B:
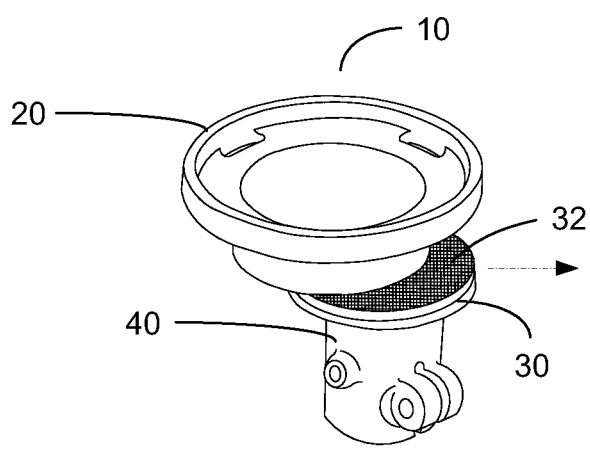
Figure 8C:
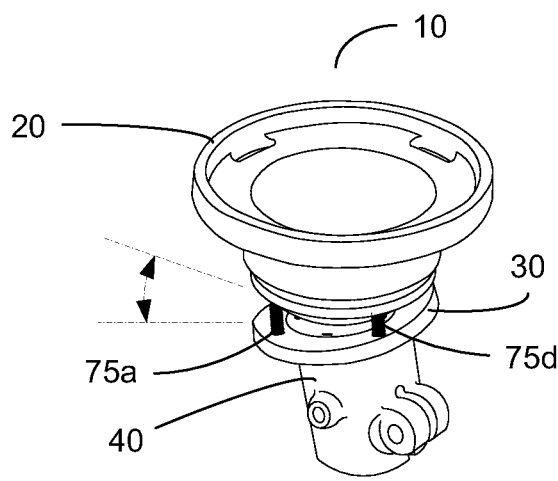

FIGS. 8a, 8b, and 8c illustrate front-back, side-to-side, and angular adjustment of an exemplary embodiment of connector 10, which allow the angle and position of prosthetic foot 115 (FIG. 11) to be changed (e.g., to compensate for foot inset-outset). In FIG. 8a, upper assembly 20 has been shifted backward (i.e., along x-axis) in relation to central plate 30 and lower assembly 40. In FIG. 8b, upper assembly 20 has been shifted sideways (i.e., along y-axis) in relation to central plate 30 and lower assembly 40.

When upper assembly 20 is shifted forward-backward or sideways (i.e., along x- or y-axis) in relation to central plate 30 and lower assembly 40, a portion of recessed grid pattern 28 (not visible) on the lower surface of upper assembly 20 and portion of raised grid pattern 32 on the upper surface of central plate 30 are exposed. The size of aperture 22 in upper assembly 20 and aperture 35 in central plate 30 permit tapered shoulder screw 70 (not visible) to be angled when upper assembly 20 is shifted forward-backward and/or sideways in relation to central plate 30 and lower assembly 40, ensuring that upper assembly 20, central plate 30, and lower assembly 40 are secure.

In FIG. 8c, upper assembly 20 and central plate 30 are tilted in relation to lower assembly 40 so that central plate 30 and central plate flange 45 on lower assembly 40 are no longer parallel. The concave center portion of the top surface of lower assembly 40 allows rounded protuberance 37 on the bottom of central plate 30 to tilt, allowing for angular adjustment of upper assembly 20 and central plate 30. When upper assembly 20 and central plate 30 are positioned at the desired angle, central plate supporting components 75a, 75b, 75c, 75d are tightened, securing lower assembly 40 to upper assembly 20 and central plate 30.

In the embodiment shown, connector 10 is capable of being adjusted in one or more directions concurrently, allowing for maximum adjustment of connector 10 to specifically accommodate each amputee's residual limb and gait. For example, connector 10 may be adjusted front-back, side-to-side, and angled. In other embodiments, connector 10 may be capable of only one type of adjustment (e.g., angular).

Figure 9A:
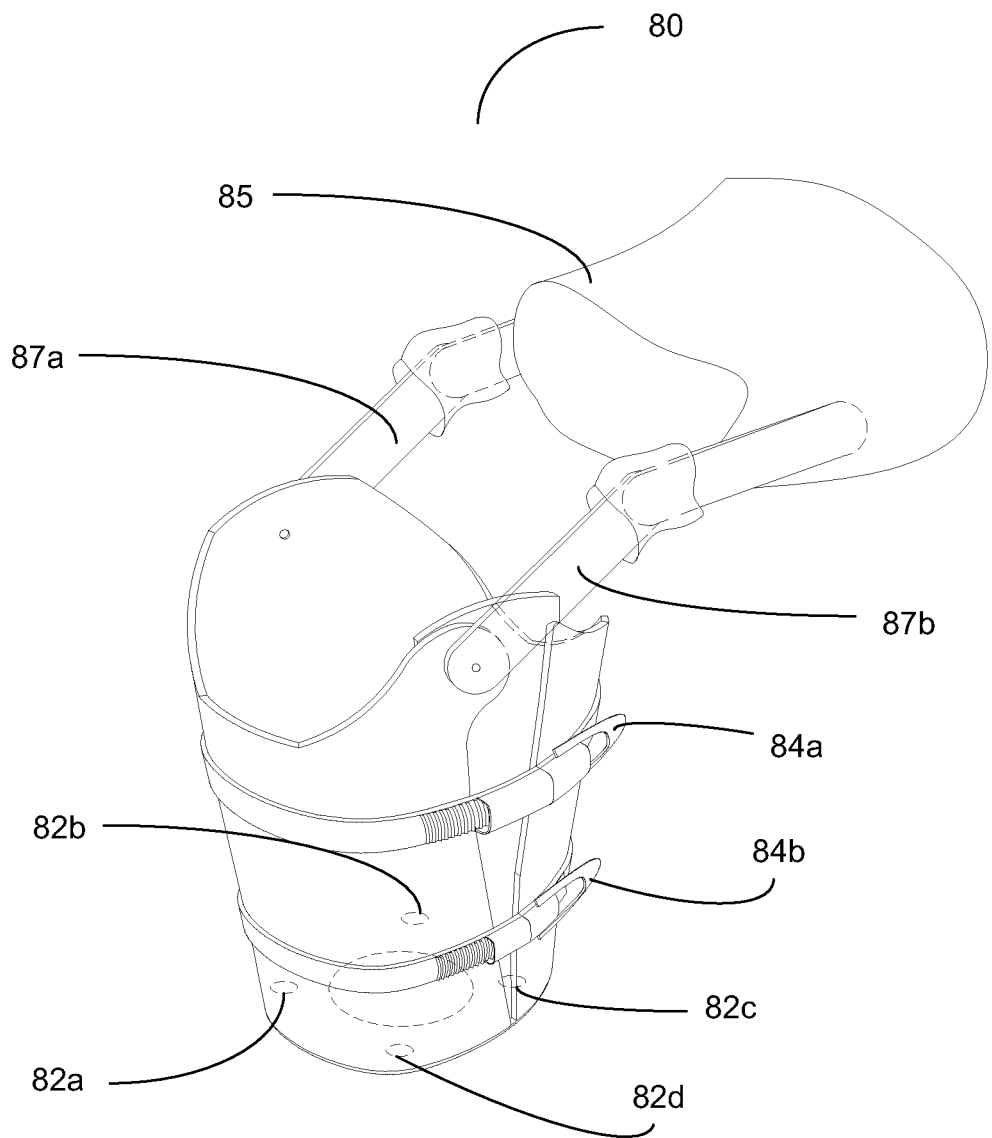
FIGS. 9a and 9b illustrate perspective views of exemplary embodiments of a socket for a modular prosthesis system.
Figure 9B:
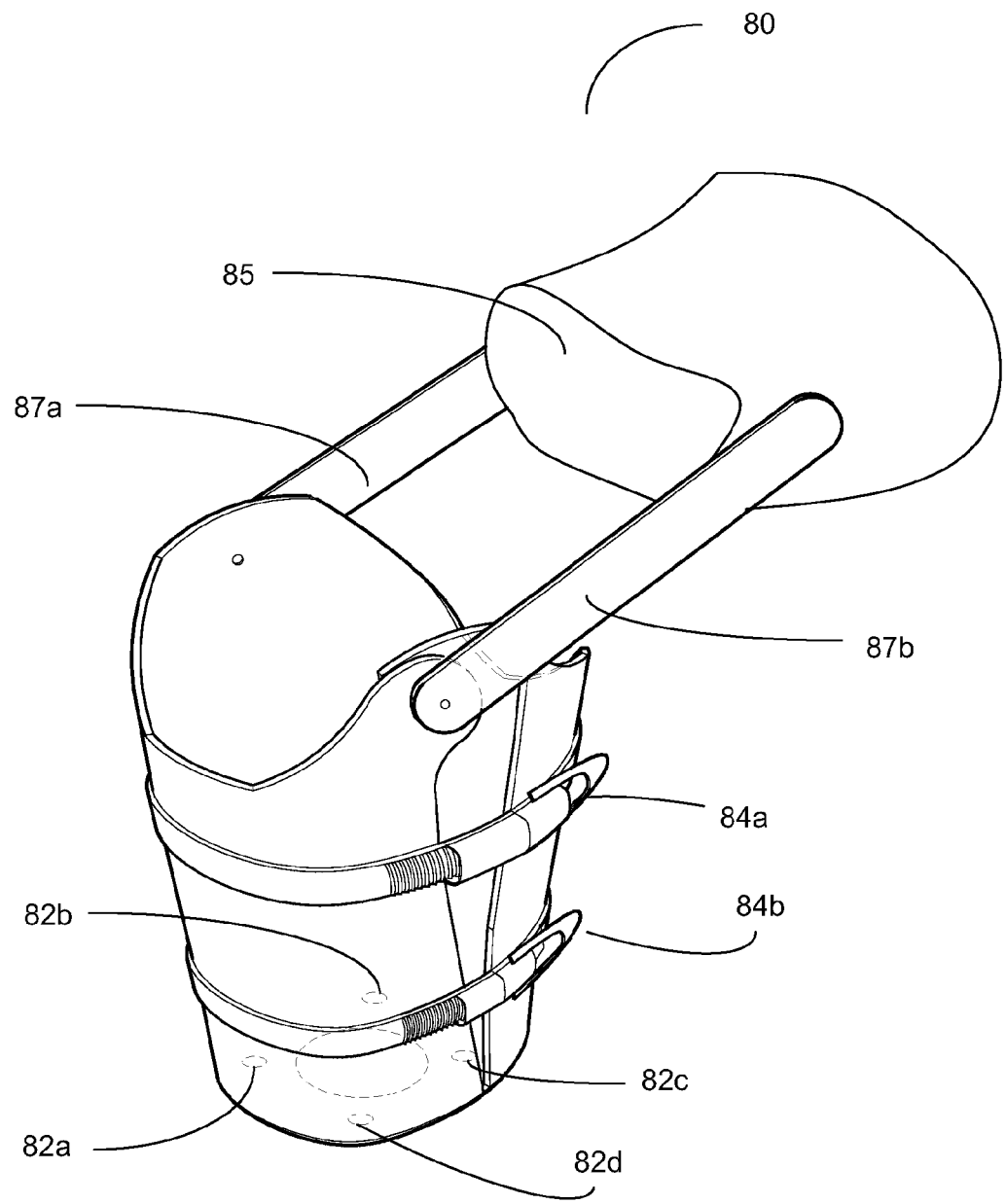

FIGS. 9a and 9b illustrate perspective views of exemplary embodiments of socket 80 for modular prosthesis system 100. Socket 80 includes tightening components 84a, 84b, which allow the tension in socket 80 to be adjusted by each amputee. In the embodiment shown, socket tightening components 84a, 84b are buckle assemblies.

In the embodiment shown, socket 80 further includes suspension system 85 with optional pivotal side joints 87a, 87b. Suspension system 85 secures the prosthesis on the amputee's residual limb. The inclusion of pivotal side joints 87a, 87b allows the amputee to move his or her knee more freely with less hindrance from the prosthesis. In various other embodiments, suspension system 85 may vary. For example, suspension system 85 may be comprised of a roll-on neoprene sleeve with an adjustable strap that goes around the amputee's thigh and one or more length-adjustable straps that connect the sleeve to socket 80.

In FIG. 9a, optional pivotal side joints 87a, 87b are comprised of two pieces connected at a joint. In various embodiments, the joint may be located further from or closer to suspension system 85. In FIG. 9b, optional pivotal side joints 87a, 87b are comprised of a single straight piece. In various embodiments, there may be fewer or more joints, the pieces may be of varying length, and/or curved or irregularly-shaped.

In various other embodiments, there may be more socket tightening components 84a, 84b and/or the type of tightening components may vary. For example, socket 80 may include laces or one or more straps secured by hook-and-loop fastener or another means, as well as combinations of such tightening components.

Also visible are apertures 82a, 82b, 82c, 82d for inserting securing components 29a, 29b, 29c, 29d (not visible) for securing connector 10 to socket 80.

FIG. 10 illustrates a perspective view of an exemplary embodiment of liner 90 for modular prosthesis system 100. Liner 90 is shaped to fit inside socket 80. In the embodiment shown, liner 90 further includes liner extension component 96 which allows the height of the liner to be adjusted to the length of each amputee's residual limb. In the embodiment shown, liner extension component 96 is a plurality of accordion fabric folds at the bottom portion of liner 90. In various other embodiments, liner extension component 96 may be comprised of adjustable or removable panels or another component that allows the length of liner 90 to be adjusted.

In the embodiment shown, liner 90 has tightening component 95 which allows the tension of liner 90 to be adjusted as the residual limb changes, accommodating long-term or daily changes of the residual limb, as well as allowing the individual amputee to adjust liner 90 to his or her comfort. For example, liner tightening component 95 allows liner 90 to be loosened as a result of swelling of the residual limb. In the embodiment shown, liner tightening component 95 is laces. In various other embodiments, liner tightening component 95 may include one or more adjustable straps.

In the embodiment shown, liner 90 includes stress distribution panels 92a, 92b secured to the outer surface of the sides of liner 90 and stress distribution panels 92c, 92d (92d not visible) secured to the outer surface of the front and back of liner 90. Stress distribution panels 92a, 92b, 92c, 92d help to distribute pressure and shear stresses. In the embodiment shown, stress distribution panels 92a, 92b are comprised of plastic. In various embodiments, the shape of the stress distribution panels varies depending on the placement of the panel (i.e., the side panels have a shape different than that of front and back panels).

In an exemplary embodiment, liner 90 further includes one or more optional removable padding inserts 98, which can be inserted into liner 90 for further adjustability, allowing liner 90 to accommodate the shape of each individual amputee's residual limb. For example, padding inserts may be inserted into the bottom of liner 90 to accommodate a bony prominence at the end of a residual limb or into the sides of liner 90 to add additional padding in areas that are less pressure tolerant.

Liner 90 is comprised of a soft, comfortable material, such as PE-LITE or silicone, that doesn't break down the skin of the amputee's residual limb. In various other embodiments, liner 90 may be comprised of a plastic mesh material or other material that allows for breathability for use in warmer climates or during physical activities. In various embodiments, liner 90 may be manufactured by gluing together layers of foam having different durometers.

FIG. 11 illustrates a perspective view of an exemplary embodiment of assembled modular prosthesis system 100. In an exemplary embodiment, modular prosthesis system 100 includes all items and components required for immediate fitting. Connector 10, shank 110, and foot 115 may be one fully adjustable system that readily connects to socket 80 and suspension system 85. Liner 90 is inserted into socket 80. In an exemplary embodiment, modular prosthesis system 100 may include a telescoping shank.

Figure 12:
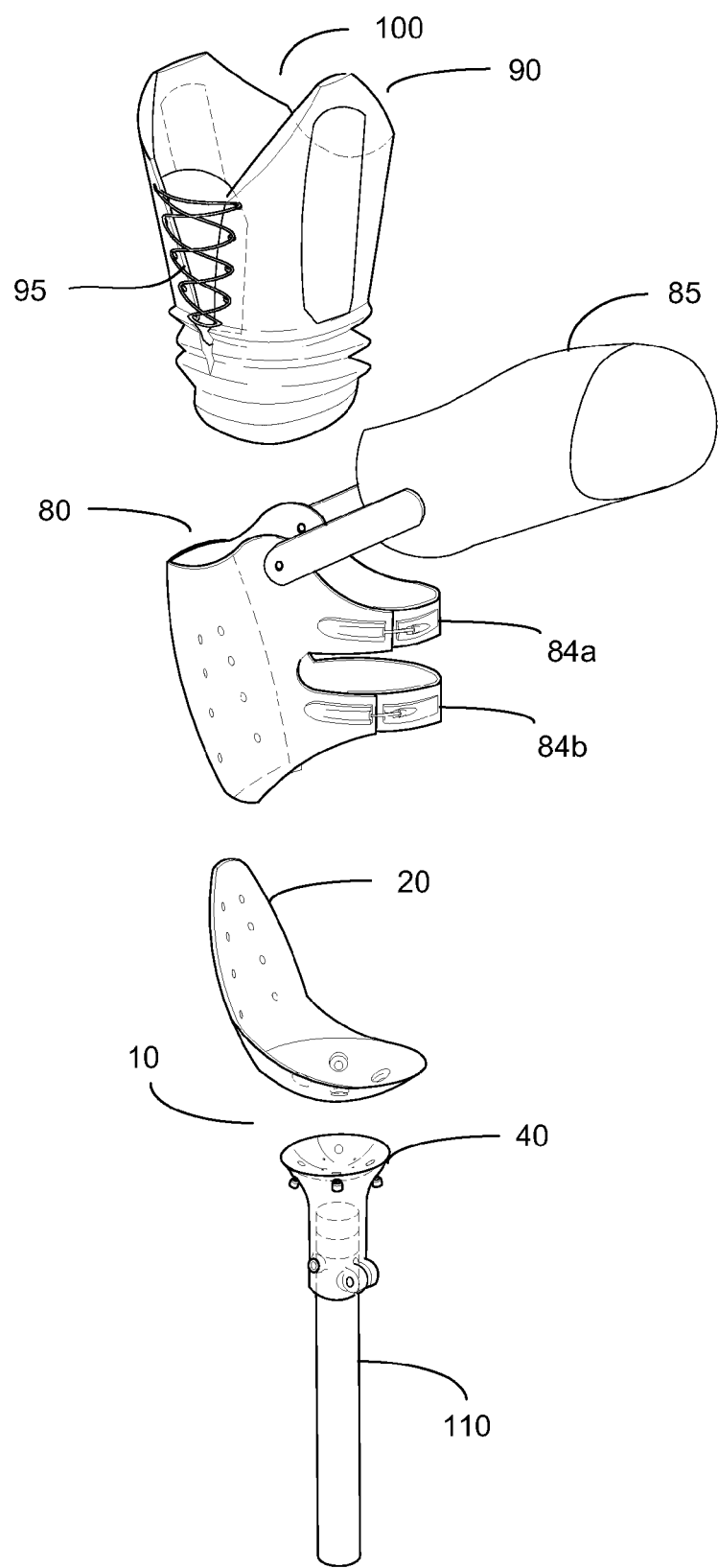
FIG. 12 illustrates an exploded view of another embodiment of a modular prosthesis system.

FIG. 12 illustrates an exploded view of another embodiment of modular prosthesis system 100 comprised of socket 80, liner 90, and connector 10. In the embodiment shown, socket 80 and liner 90 include tightening components 84a, 84b, and 95, respectively, and socket 80 further includes suspension system 85.

In the embodiment shown, connector 10 is comprised of upper assembly 20 and lower assembly 40. Upper assembly 20 is cup-shaped with a rounded bottom and a single elongated side. Lower assembly 40 is tubular-shaped having a flange with a concave center portion and a bottom portion for accepting shank 110. In the embodiment shown, upper assembly 20 is secured to lower assembly 40 by inserting a connecting screw (e.g., a tapered shoulder screw) or another type of fastener into each of the apertures in the rounded bottom of upper assembly 20 and into the apertures in the concave center portion of lower assembly 40. The position of the connecting screws can be adjusted to adjust the tilt between upper assembly 20 and lower assembly 40, allowing the position of the prosthetic foot to be adjusted (e.g., to compensate for foot inset-outset).

In the embodiment shown, the apertures in the bottom of upper assembly 20 are recessed to allow for placement of a washer.

In the embodiment shown, the single elongated side of upper assembly 20 includes a plurality of apertures which correspond to the apertures on socket 80. Socket 80 is secured to upper assembly 20 of connector 10 by threading a screw through two apertures (single row) in socket 80 and upper assembly 20. The plurality of rows of apertures accommodates for height adjustment. For example, for a shorter socket, the amputee would thread screws through the top four apertures of socket 80 and the top four apertures of upper assembly 20 (or any four corresponding apertures). For a longer socket, the amputee would thread screws through the bottom four apertures of socket 80 and the top four apertures of upper assembly 20. For shorter lengths, additional screws could be threaded through corresponding apertures to secure socket 80 and upper assembly more tightly together.

Modular prosthesis system 100 is easily fit to an individual and can be fully constructed and aligned in a reasonable amount of time. No casting or fabrication is required, eliminating the need for specialized tools and centers.

Modular prosthesis system 100 is highly adjustable, making it ideal for growing children, eliminating the need for many prosthetic revisions to insure a comfortable and functional device. In addition, modular prosthesis system 100 can be fit without a prosthetist making it desirable for developing countries, war-torn countries, and for individuals who are without insurance and/or don't have access to a prosthesis. The use of advanced technology and materials allows modular prosthesis system 100 to be economically manufactured and distributed.

Figure 13:
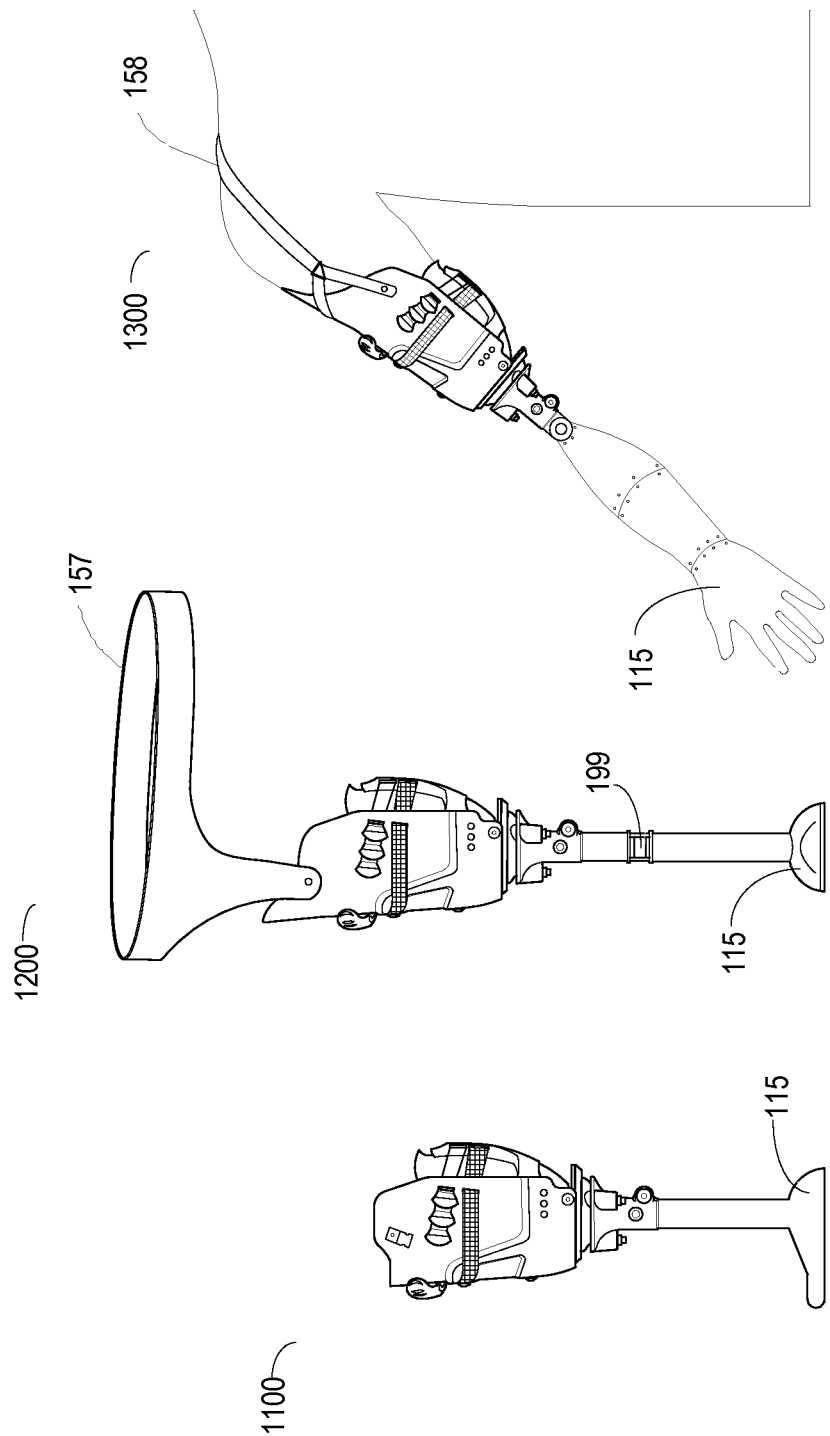
FIG. 13a illustrates an exemplary embodiment of a rapid fit modular prosthetic device for accommodating gait alignment and residual limb shape and volume for a below-the-knee residual limb.
FIG. 13b illustrates an exemplary embodiment of a rapid fit modular prosthetic device for accommodating gait alignment and residual limb shape and volume for an above-the-knee residual limb.
FIG. 13c illustrates an exemplary embodiment of a rapid fit modular prosthetic device for accommodating gait alignment and residual limb shape and volume for a residual limb which is an arm.

FIGS. 13a, 13b and 13c illustrate three different uses of a rapid fit modular prosthetic device for accommodating gait alignment and residual limb shape and volume. As illustrated in FIG. 13a, rapid fit modular prosthetic device for accommodating gait alignment and residual limb shape and volume 1100 is adapted for use on a below-the-knee residual limb. As illustrated in FIG. 13b, rapid fit modular prosthetic device for accommodating gait alignment and residual limb shape and volume 1200 may also be adapted for use with an above-the-knee residual limb. FIG. 13c illustrates rapid fit modular prosthetic device for accommodating gait alignment and residual limb shape and volume 1300 adapted for use with a residual limb which is an arm.

As illustrated in FIGS. 13a, 13b and 13c, the basic structure of rapid fit modular prosthetic device for accommodating gait alignment and residual limb shape and volume 1100, 1200, 1300 is the same. Rapid fit modular prosthetic device for accommodating gait alignment and residual limb shape and volume 1100 has prosthetic device 115 attached directly to rapid fit modular prosthetic device for accommodating gait alignment and residual limb shape and volume 1100. By comparison, rapid fit modular prosthetic device for accommodating gait alignment and residual limb shape and volume 1200 has knee 199 after prosthetic device 115 and an additional securing strap 157 to help stabilize rapid fit modular prosthetic device for accommodating gait alignment and residual limb shape and volume 1200. The orientation of prosthetic device 115 is also rotated at 90 degrees compared to rapid fit modular prosthetic device for accommodating gait alignment and residual limb shape and volume 1100.

When used for a below-the-knee residual limb, rapid fit modular prosthetic device for accommodating gait alignment and residual limb shape and volume 1100 is oriented so that it opens from the back of a wearer (i.e., at the calf). Because of the way pressure is exerted on rapid fit modular prosthetic device for accommodating gait alignment and residual limb shape and volume 1200 when used with an above-the-knee residual limb, and the movement caused by bending at the knee, rapid fit modular prosthetic device for accommodating gait alignment and residual limb shape and volume 1200 must be oriented to open from the side.

Similarly, as illustrated in FIG. 13c, rapid fit modular prosthetic device for accommodating gait alignment and residual limb shape and volume 1300 contains a different strap 158 to secure rapid fit modular prosthetic device for accommodating gait alignment and residual limb shape and volume 1300 to a residual limb which is an arm, and prosthetic device 115 is an arm instead of a foot or leg.

Figure 14:
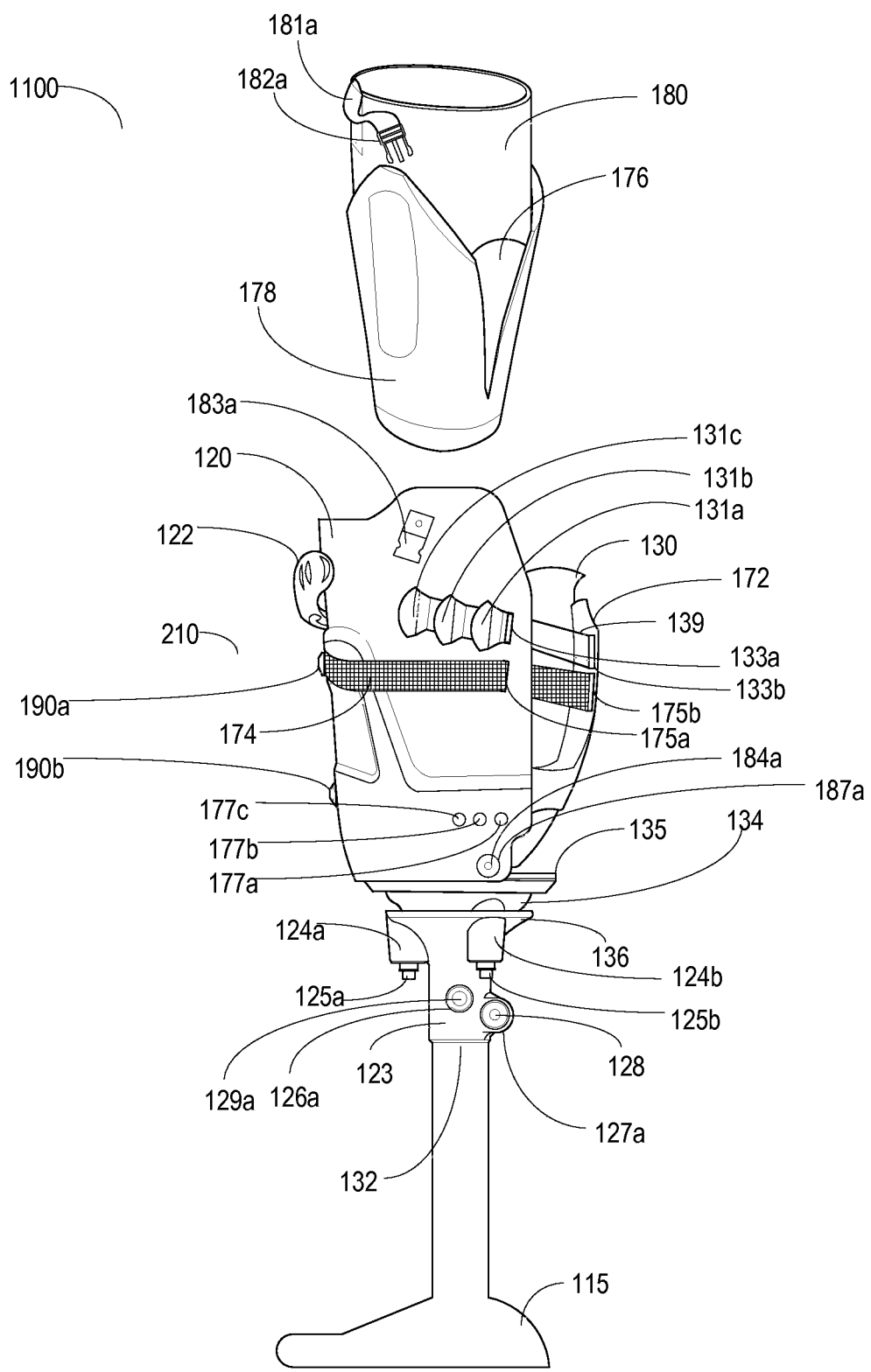
FIG. 14 illustrates an exemplary below-the-knee rapid fit modular prosthetic device for accommodating gait alignment and residual limb shape and volume.

FIG. 14 illustrates an exemplary embodiment of below-the-knee rapid fit modular prosthetic device for accommodating gait alignment and residual limb shape and volume 1100. Below-the-knee rapid fit modular prosthetic device for accommodating gait alignment and residual limb shape and volume 1100 contains rigid socket assembly 210, which is comprised of non-pivotal front limb engaging panel 120, pivotal rear limb engaging panel 130, rigid outer support rib 172, and deformable inner liner 178 with silicone liner 180. In the exemplary embodiment shown, rigid socket assembly 210 creates a tubular recess which receives a residual limb.

As illustrated in FIG. 14, pivotal rear limb engaging panel 130 overlaps non-pivotal front limb engaging panel 120 on the inside of non-pivotal front limb engaging panel 120. Rigid outer support rib 172 has an inverted T-shape and supports pivotal rear limb engaging panel 130 in front limb engaging panel 120.

In the exemplary embodiment shown, rigid outer support rib 172 is a separate physical component from rear limb engaging panel 130. In other exemplary embodiments, rigid outer support rib 172 may be permanently or temporarily connected with rear limb engaging panel 130. In still further exemplary embodiments, rigid outer support rib 172 may be singly manufactured with rear limb engaging panel 130.

In the exemplary embodiment shown, pivotal rear limb engaging panel 130 is pivoted to exert an even pressure and hold a residual limb in the place against front limb engaging panel 120. In a preferred exemplary embodiment, pivotal rear limb engaging panel 130 pivots at 10-40 degrees. (Persons skilled in the art will recognize that a wider range between 0 degrees and 90 degrees is feasible.) Rear limb engaging panel 130 is flexible and narrow as it is compressed in the contour of the more rigid and longer non-pivotal front limb engaging panel 120. Rigid outer support rib 172 provides structure to rear limb engaging panel 130.

As illustrated in the exemplary embodiment shown in FIG. 14, deformable inner liner 178 with silicone liner 180 is designed to fit within rigid socket assembly 210 to accommodate the individual and unique features of a residual limb to provide comfort and reduce impact. Silicone liner 180 cushions and conforms to the shape of a residual limb, while deformable inner liner 178 provides additional cushioning and support. In the exemplary embodiment shown, deformable inner liner 178 is made of cushioning material, such as deformable padding, foam, cushioning, gel, rubber or combinations of these materials. In further exemplary embodiments, deformable liner 178 may be malleable, moldable, or adjustable to specifically fit a residual limb.

While in the exemplary embodiment shown, silicone liner 180 is made of silicone, in further exemplary embodiments, silicone liner 180 may be made of any similar material known in the art. In still further exemplary embodiments, the material properties between silicone liner 180 and deformable inner liner 178 may be designed to provide added friction for augmented suspension when modular prosthetic device 1100 is firmly buckled around a residual limb.

In yet further exemplary embodiments, silicone liner 180 and deformable inner liner 178 may include a directional resistance material which allows silicone liner 180 to easily engage deformable inner liner 178 but prevents silicone liner 180 from being easily removed or shifted once in deformable inner liner 178. For example, the inner surface of deformable inner liner 178 and the outer surface of silicone liner 180 may contain an area, areas, or coating of a directionally resistive material. In still further exemplary embodiments, the outer surface of silicone liner 180 and the inner surface of deformable inner liner 178 may include engaging structures which allow silicone liner 180 to be easily inserted in deformable inner liner 178, but require additional force to remove from deformable inner liner 178.

In some exemplary embodiments, rigid socket assembly 210 and first convex plate base 135 with integrally molded longitudinal curved plate 134 may be modified to accommodate silicone liner 180 with a serrated pin suspension system, such as with the ALPS pin and gel liner suspension system known in the art.

Deformable liner 178 is shown having rear tongue 176 and a contoured front, which are adapted to comfortably receive a residual limb.

In the exemplary embodiment shown, silicone liner 180 also contains suspension straps 181a, 181b (not shown) with suspension strap buckles 182a, 182b (not shown). Suspension strap 181b with suspension strap buckle 182b is symmetrically arranged on the opposite side of silicone liner 180. In some exemplary embodiments, suspension straps 181a, 181b with suspension strap buckles 182a, 182b may be omitted, or additional or different securing components may be used.

Suspension strap buckles 182a, 182b engage corresponding suspension strap buckles 183a, 183b (not shown) on non-pivotal front limb engaging panel 120 to secure silicone liner 180 and deformable inner liner 178 to rigid socket assembly 210. In further exemplary embodiments, silicone liner 180 may be temporarily or permanently connected to rigid socket assembly 210 through any means known in the art, including clasps, clips, buckles, straps, adhesives, friction-fit components, contours, snaps, or combinations of these or other structures.

As illustrated in FIG. 14, non-pivotal front limb engaging panel 120 and pivotal rear limb engaging panel 130 are secured together around a residual limb by an intricate strap/buckle assembly comprised of buckle 122, looped cable 139, hook-shaped cable protuberances 131a, 131b, 131c and securing strap 174.

Securing strap 174 completely encircles non-pivotal front limb engaging panel 120 and pivotal rear limb engaging panel 130 and secures to rigid socket assembly 210 through securing strap apertures 175a, 175b, 175c (not shown). In the exemplary embodiment shown, securing strap 174 is made of a non-elastic material and serves as a safety strap. In further exemplary embodiments, securing strap 174 may be any material with a buckle or other structure which allows the tension on securing strap 174 to be adjusted. For example, the tension on securing strap 174 may be adjusted using buckles, clasps, clips, snaps or any other structure or combination of structures known in the art.

In the exemplary embodiment shown, securing strap aperture 175b creates a hollow opening perpendicular to the longitudinal portion of rigid outer support rib 172. Securing strap 174 is therefore able to pass completely through the longitudinal portion of rigid outer support rib 172. Securing strap aperture 175c (not shown) is symmetrically positioned on the opposite side of front limb engaging panel 120.

Similarly, looped cable 139 is connected on one end to buckle 122 and to hook-shaped cable protuberance 131c on the other end to partially encircle non-pivotal front limb engaging panel 120 and pivotal rear limb engaging panel 130. Looped cable 139 proceeds from buckle 122 through apertures 133c (not shown), 133b, 133a, and is then looped around one of hook-shaped cable protuberances 131a, 131b, 131c, depending on the size of a residual limb. As illustrated in FIG. 14, cable aperture 133b creates a hollow opening perpendicular to the longitudinal portion of rigid outer support rib 172. Looped cable 139 is therefore able to pass completely through the longitudinal portion of rigid outer support rib 172. Cable aperture 133c (not shown) is symmetrically positioned on the opposite side of non-pivotal front limb engaging panel 120.

In the exemplary embodiment shown, looped cable 139 is made of metal wire with a protective coating, such as rubber or any other moisture- and/or rust-resistant coating known in the art. Looped cable 139 goes through apertures 133a, 133b, 133c (not shown) to minimize the pressure and wear exerted on the ends of non-pivotal front limb engaging panel 120.

Once looped cable 139 is secured around one of hook-shaped cable protuberances 131a, 131b, 131c, buckle 122 is closed against front limb engaging panel 120 to pull looped cable 139 tight around rigid socket assembly 210. In the exemplary embodiment shown, buckle 122 is a buckle similar to the type traditionally used on ski boots. In further exemplary embodiments, buckle 122 may be any commercially available plastic buckle or assembly which allows leverage and tightening of looped cable 139. In still further exemplary embodiments, buckle 122 may be several buckles or securing components.

As illustrated in FIG. 14, non-pivotal front limb engaging panel 120 also contains base plate bolts 184a, 184b (not shown) and hinge bolt apertures 177a, 177b, 177c, with symmetrically arranged hinge bolt apertures 177d, 177e, 177f (not shown) on the opposite side of front limb engaging panel 120. Hinge bolt apertures 177a, 177b, 177c, and 177d (not shown), 177e (not shown), 177f (not shown) adjustably secure rigid outer support rib 172 and pivotal rear limb engaging panel 130 to non-pivotal front limb engaging panel 120.

Base plate bolts 184a, 184b (not shown) help join non-pivotal front limb engaging panel 120, and therefore a residual limb, to fitted base component 140 (not shown), containing first convex plate base 135 with integrally molded longitudinal curved plate 134. Base plate bolts 184a, 184b (not shown) project through base plate apertures 187a, 187b (not shown) in front limb engaging panel 120 and base plate apertures 85a (not shown), 185b (not shown) in fitted base component 140. Base plate aperture sets (e.g., 187a/187b and 185a/185b) are symmetrically positioned on opposite sides of their respective structural components.

Rocker connector bolts 125a, 125b, 125c (not shown) project through radial tubular portions 124a, 124b, 124c (not shown) of central hollow tubular portion 123 to secure integrally molded longitudinal curved plate 134 to concave plate base 136.

Hollow tubular portion 123 contains prosthetic pipe connector 132, which receives prosthetic device 115, which in the exemplary embodiment shown is a foot. In the exemplary embodiment shown, prosthetic pipe connector 132 is 30 mm in diameter. In further exemplary embodiments, prosthetic pipe connector 132 may have a diameter between 27 and 32 millimeters. Prosthetic device 115 is secured in hollow tubular portion 123 by set screws 129a, 129b (not shown), which project through set screw apertures 126a, 126b (not shown), and tightening bolt 128 in base clamping protuberances 127a, 127b (not shown).

Also illustrated in FIG. 14 are securing bolts 190a, 190b. Securing bolts 190a, 190b project through securing apertures 191a (not shown), 191b (not shown) in front limb engaging panel 120 and securing apertures 192a (not shown), 192b (not shown) in fitted base component 140 (not shown). Securing strap 174 also contains securing aperture 195 (not shown), which allows securing bolt 190a to vertically lock securing strap 174 in place.

In further exemplary embodiments securing strap 174 may be vertically locked in place by additional bolts or other structures, including, but not limited to, clips, clasps, buttons, or combinations of these and other structures.

Figure 15:
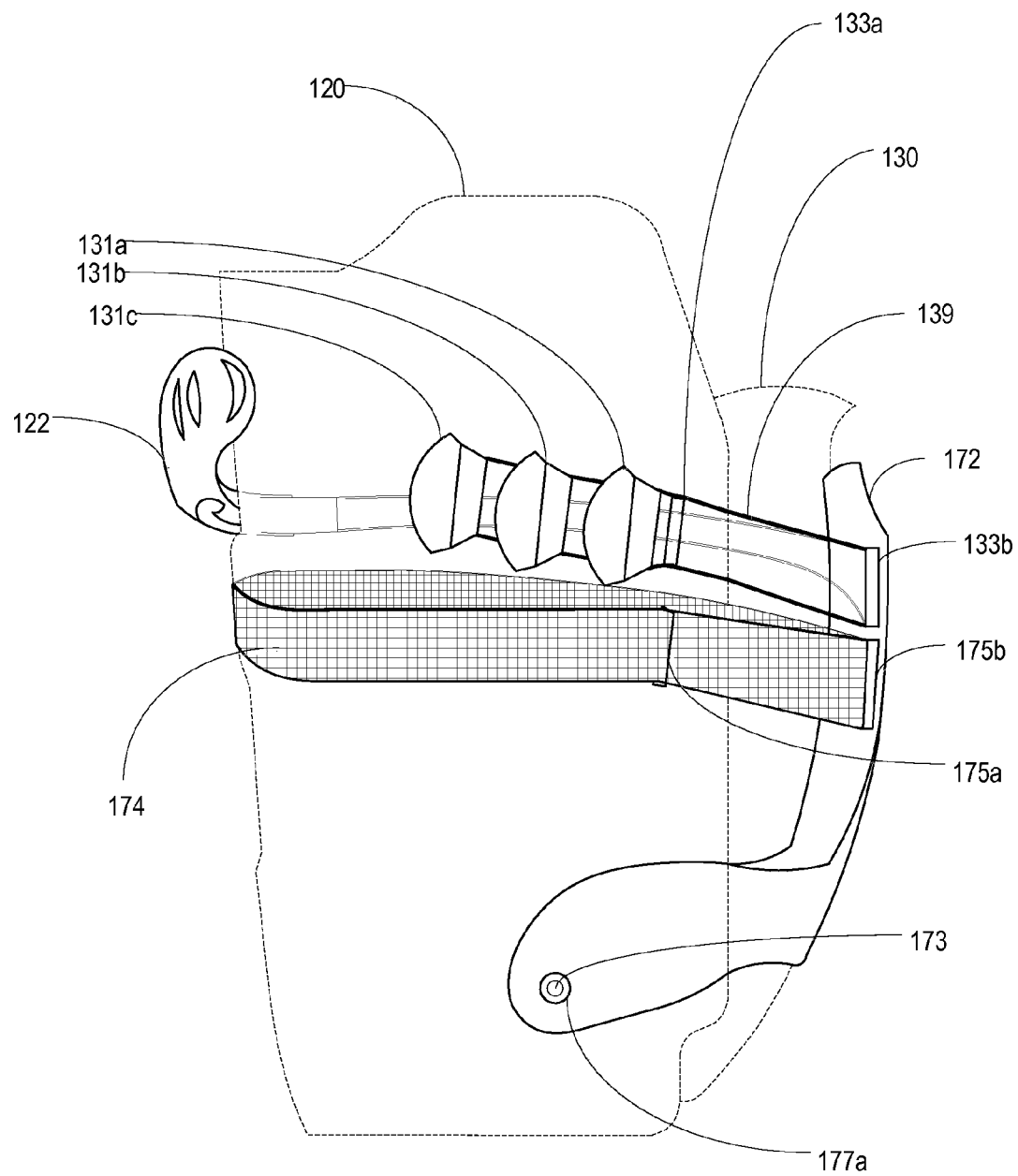
FIG. 15 illustrates an exemplary embodiment of a buckle cable system and hinge for a rapid fit modular prosthetic device for accommodating gait alignment and residual limb shape and volume.

FIG. 15 is an exemplary embodiment of a buckle/cable system of rigid socket assembly 210. The buckle/cable system secures non-pivotal front limb engaging panel 120, pivotal rear limb engaging panel 130 and rigid outer support rib 172 around a residual limb. In the exemplary embodiment shown, non-pivotal front limb engaging panel 120 and pivotal rear limb engaging panel 130 are shown in phantom to better view the components of the buckle/cable system.

As illustrated in FIG. 15, looped cable 139 is attached at one end to buckle 122. Looped cable 139 proceeds around the outside of non-pivotal front limb engaging panel 120 and goes through cable aperture 133c (not shown) on the opposite side of non-pivotal front limb engaging panel 120, and then passes through cable aperture 133b in rigid outer support rib 172. Looped cable 139 continues around the rear of rigid socket assembly 210 and passes through cable aperture 133a in non-pivotal front limb engaging panel 120. In the exemplary embodiment shown, looped cable 139 is looped around hook-shaped cable protuberance 131c, but in further exemplary embodiments, may be looped around any one of hook-shaped cable protuberances 131a, 131b, 131c, depending on the size of a residual limb. Buckle 122 tightens against non-pivotal front limb engaging panel 120 to tighten looped cable 139.

In the exemplary embodiment shown, securing strap 174 is a non-elastic component completely encircling rigid socket assembly 210. Securing strap 174 passes around the exterior of pivotal rear limb engaging panel 130 by passing through securing strap apertures 175c (not shown), 175b, 175a. Cable apertures 133a, 133b, 133c (not shown) and securing strap apertures 175a, 175b, 175c (not shown) allow looped cable 139 and securing strap 174 to tighten around rigid socket assembly 210 without putting excess pressure and strain on the edges of non-pivotal front limb engaging panel 120.

In further exemplary embodiments, rigid socket assembly 210 may contain more or fewer securing cables/straps, and securing cables or straps may have selective or continual adjustability around rigid socket assembly 210. For example, additional hook-shaped cable protuberances 131 may be available for looped cable 139. Additional tightening components, such as buckles, clasps, clips, snaps or any other structure or combination of structures, may be used to provide additional adjustment to looped cable 139 or securing strap 174.

In still further exemplary embodiments, rigid outer support rib 172 may contain additional apertures for looped cable 139 or securing strap 174.

In the exemplary embodiment shown, rigid outer support rib 172 has an inverted T-shape and is rigid to provide structural support for flexible rear limb engaging panel 130. Hinge bolt 173 projects through hinge bolt aperture 177a on non-pivotal front limb engaging panel 120, and corresponding hinge bolt apertures 117a and 118a on rear limb engaging panel 130 and rigid outer support rib 172, respectively, to attach rigid outer support rib 172 and rear limb engaging panel 130 to non-pivotal front limb engaging panel 120.

Hinge bolt 173 projects through one of hinge bolt apertures 177a, 177b (not shown), 177c (not shown), depending on the size of a residual limb. As illustrated in the exemplary embodiment shown in FIG. 15, the horizontal portion of T-shaped rigid outer support rib 172 extends against the interior of non-pivotal front limb engaging panel 120.

Rigid socket assembly 210 also contains symmetrically arranged hinge bolt apertures 177d (not shown), 177e (not shown), 177f (not shown) on the opposite side of front limb engaging panel 120, as well as symmetrically arranged hinge bolt apertures 117b (not shown), 118b (not shown) in rear limb engaging panel 130 and rigid outer support rib 172, respectively. A second hinge bolt 173 (not shown) secures rear limb engaging panel 130 and rigid outer support rib 172 to one of hinge bolt apertures 177d (not shown), 177e (not shown), 177f (not shown).

Figure 16:
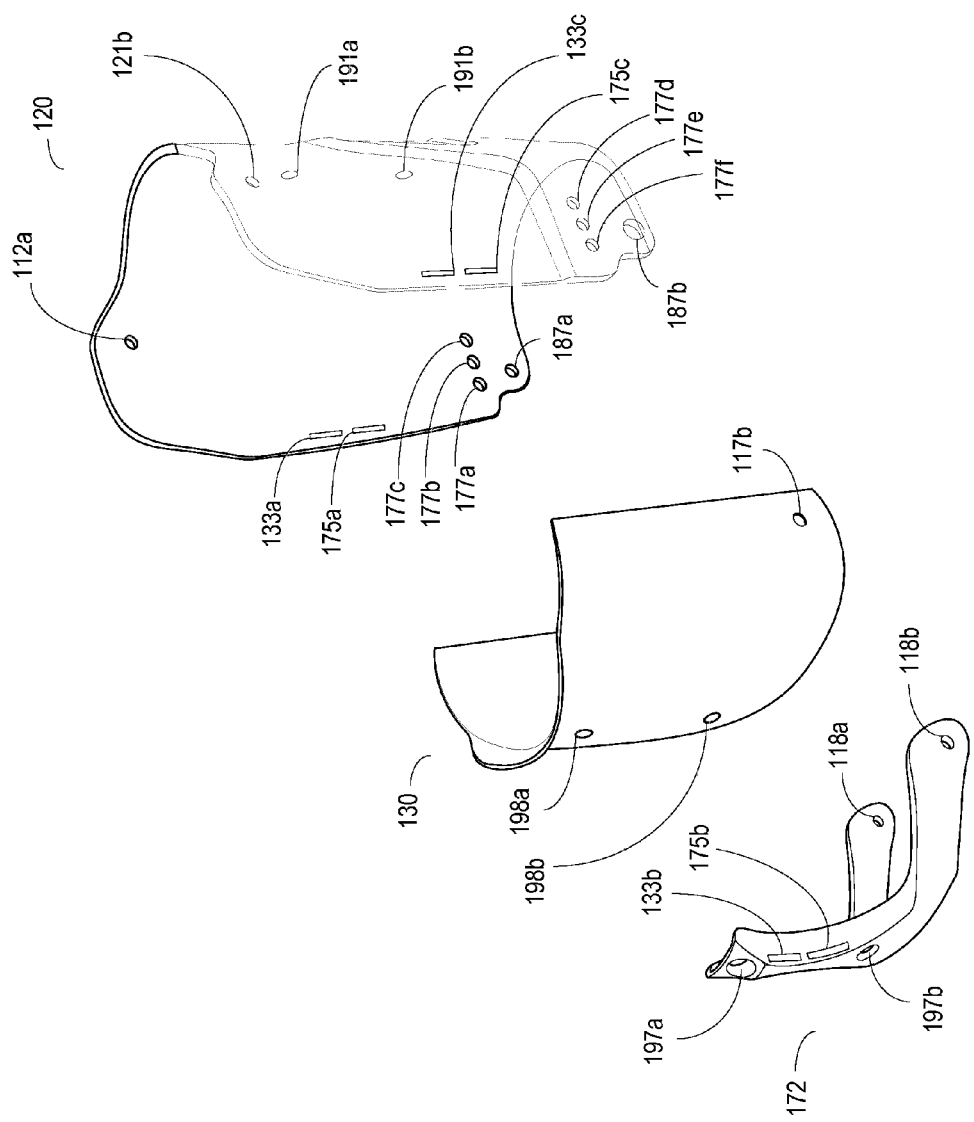
FIG. 16 illustrates an exemplary embodiment of a rigid socket assembly for a rapid fit modular prosthetic device for accommodating gait alignment and residual limb shape and volume.

FIG. 16 is an exploded view of rigid socket assembly 210. Non-pivotal front limb engaging panel 120 is shown separated from pivotal rear limb engaging panel 130 and rigid outer support rib 172. Cable apertures 133a, 133b, 133c and securing strap apertures 175a, 175b, 175c are shown without looped cable 139 (not shown) and securing strap 174 (not shown).

In the exemplary embodiment shown, rigid outer support rib 172 is a separate physical component from rear limb engaging panel 130, which securely attaches to rear limb engaging panel 130 by attachment means, such as screws or bolts, at attachment apertures 197a, 197b on rigid outer support rib and 198a, 198b on rear limb engaging panel 130. In other exemplary embodiments, rigid outer support rib 172 and rear limb engaging panel 130 may be attached by alternative structures, including, but not limited to, molding, adhesives, clips, claps, contours, or combinations of these and other attachment means.

Rigid outer support rib 172 also contains hinge bolt apertures 118a, 118b, which correspond to hinge bolt apertures 117a, 117b on rear limb engaging panel 130 and hinge bolt apertures 177a, 177b, 177c, 177d, 77e, 177f on front limb engaging panel 120. Hinge bolts 173a (not shown), 173b (not shown) engage hinge bolt aperture sets 117a/118a and 117b/118b, respectively, to adjustably and pivotally secure rigid outer support rib 172 and rear limb engaging panel 130 to front limb engaging panel 120. Hinge bolts 173a (not shown), 173b (not shown) engage one of hinge bolt apertures 177a, 177b, 177c and 177d, 177e, 177f, respectively.

In some exemplary embodiments, hinge bolts 173a (not shown), 173b (not shown) may engage symmetric hinge bolt apertures on non-pivotal front limb engaging panel 120. For example, hinge bolt 173a (not shown) may engage hinge bolt aperture 177a and hinge bolt 173b (not shown) may engage hinge bolt aperture 177f. In further exemplary embodiments, hinge bolts 173a (not shown), 173b (not shown) may engage non-symmetric hinge bolt apertures, such as 177a and 177e, respectively.

In some exemplary embodiments, hinge bolts 173a (not shown), 173b (not shown) may permanently secure rigid outer support rib 172, rear limb engaging panel 130 and front limb engaging panel 120. In other exemplary embodiments, hinge bolts 173a (not shown), 173b (not shown) may allow for selective adjustment of rigid outer support rib 172, rear limb engaging panel 130 and front limb engaging panel 120.

Base plate bolts 184a (not shown), 184b (not shown) engage base plate apertures 187a, 187b, respectively, to securely fasten front limb engaging panel 120 to fitted base component 140.

Also illustrated in FIG. 16 are attachment points 112a, 112b for suspension strap buckles 183a (not shown), 183b (not shown).

FIGS. 17a, 17b and 17c illustrate the adjustability of rigid socket assembly 210 to accommodate residual limbs of various sizes. In FIG. 17a, rigid socket assembly 210 is at its smallest size. Pivotal rear limb engaging panel 130 is recessed within front limb engaging panel 120, such that hinge bolt 173 projects through hinge bolt aperture 177c. FIG. 17b illustrates rigid socket assembly 210 with hinge bolt 173 projecting through hinge bolt aperture 177b, and FIG. 17c illustrates rigid socket assembly 210 with hinge bolt 173 projecting through hinge bolt aperture 177a.

While FIGS. 17a, 17b and 17c illustrate a single side of rigid socket assembly 210, it should be understood that front limb engaging panel 120 contains symmetrical hinge bolt apertures which are similarly engaged by a hinge bolt.

While in the exemplary embodiment illustrated in FIGS. 17a, 17b and 17c, the adjustability of rigid socket assembly 210 is limited to three pre-determined sizes, in further exemplary embodiments, additional hinge bolt apertures 177 may be provided for additional adjustability. In still further exemplary embodiments, a structure other than a hinge bolt may be used to provide continuous adjustability.

Figure 18A:
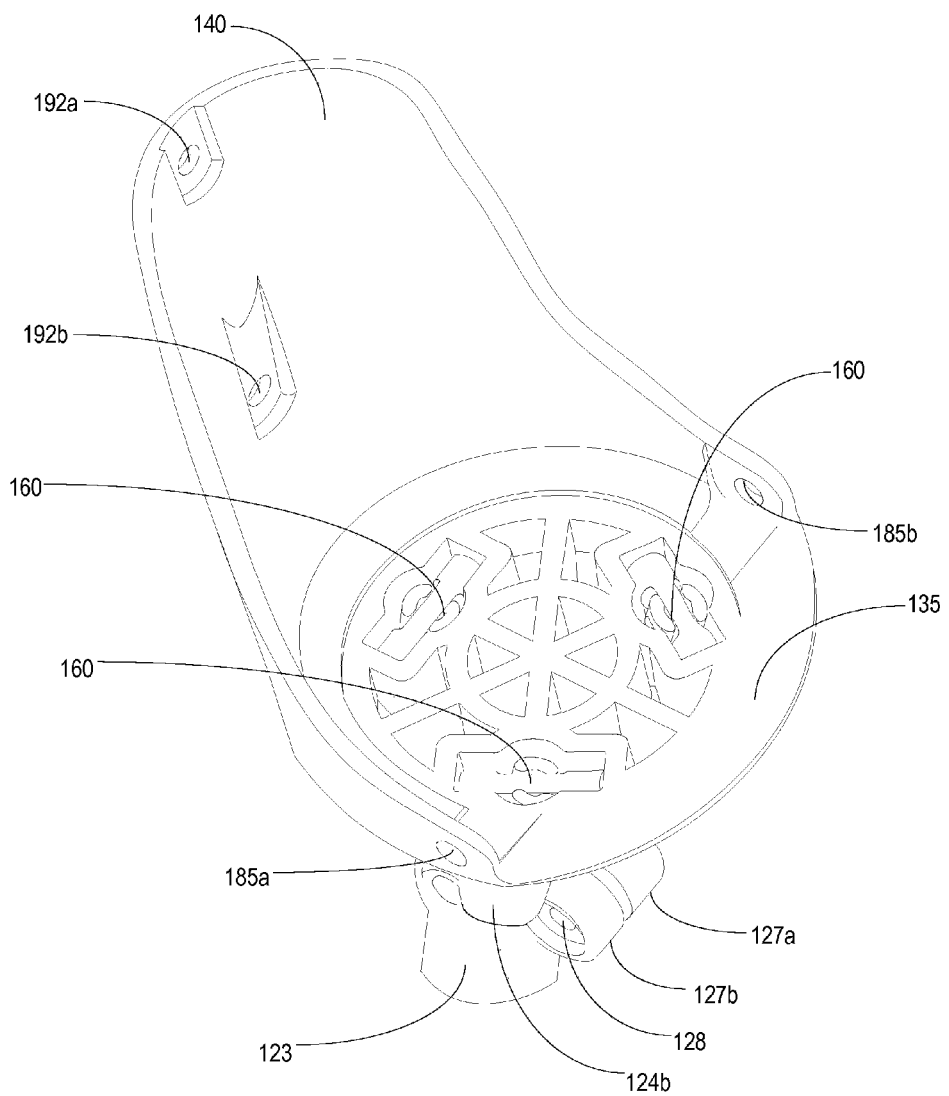
FIG. 18a illustrates an exemplary embodiment of a base component assembly for a rapid fit modular prosthetic device for accommodating gait alignment and residual limb shape and volume.
Figure 18B:
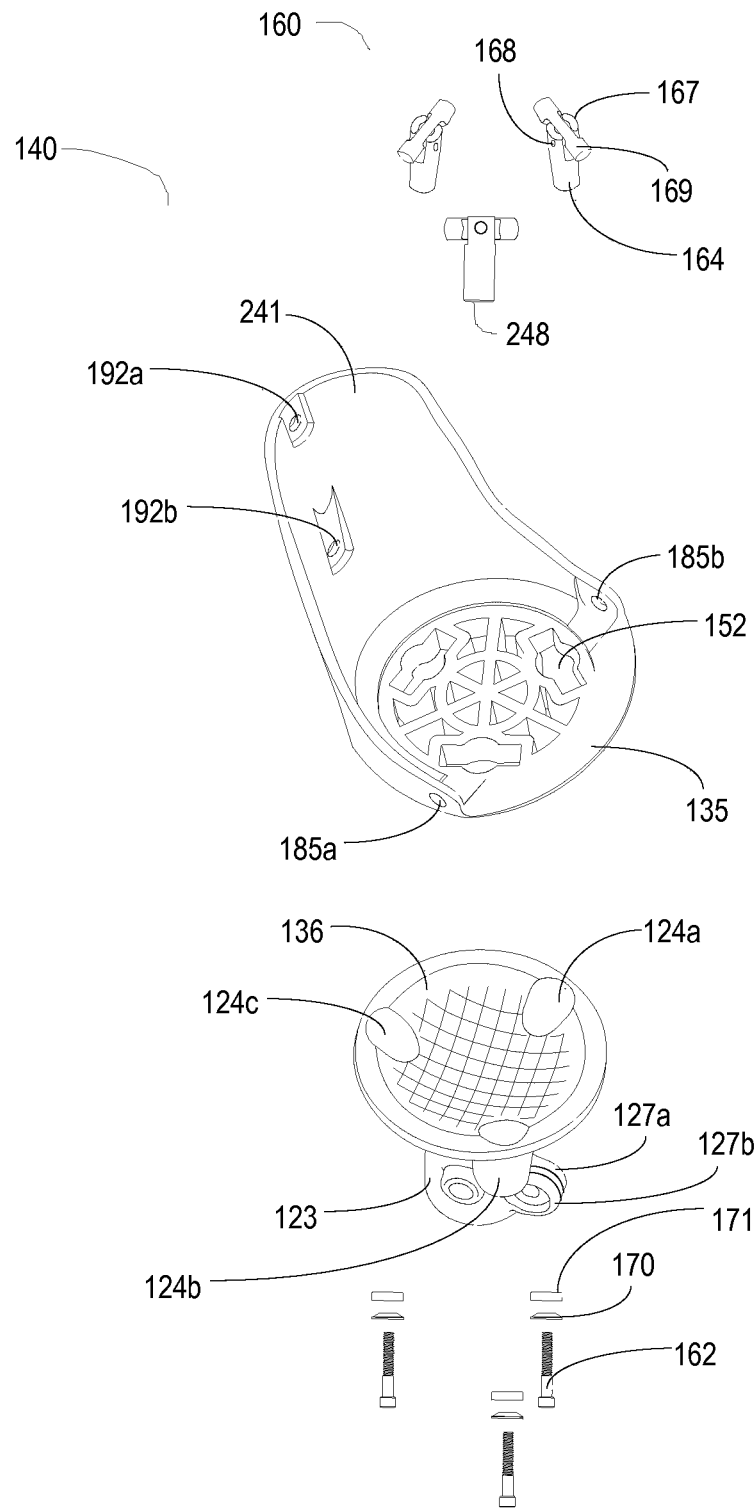
FIG. 18b illustrates an exploded view of an exemplary embodiment of a base component assembly for a rapid fit modular prosthetic device for accommodating gait alignment and residual limb shape and volume.

FIGS. 18a and 18b show the construction of an exemplary fitted base component 140. FIG. 18a illustrates an assembled fitted base component 140, with first convex plate 135 and rocker bolt assemblies 160 visible. As illustrated in FIG. 18a, convex plate 135 is an integral component with fitted base component 140 and is the top surface of fitted base component 140.

Rocker bolt assemblies 160 engage radial tubular portions 124a (not shown), 124b, 124c (not shown). Base plate bolts 184a (not shown), 184b (not shown) project through base plate apertures 185a, 185b to secure non-pivotal front limb engaging panel 120 (not shown) to fitted base component 140. When assembled, base plate apertures 185a, 185b align with base plate apertures 187a (not shown), 187b (not shown) of front limb engaging panel 120 (not shown).

Securing apertures 192a, 192b are adapted to receive securing bolts 190a (not shown), 190b (not shown), respectively, to secure fitted base component 140 to front limb engaging panel 120 (not shown).

In the exemplary embodiment shown, first convex plate 135 is constructed of a weight-bearing material.

Also illustrated in FIG. 18a are base clamping protuberances 127a, 127b with tightening bolt 128. Tightening bolt 128 pulls base clamping protuberances 127a, 127b closer together to tightly engage the pipe of a prosthetic device. In the exemplary embodiment shown, base clamping protuberances 127a, 127b are specifically designed to remain approximately 28-32 mm apart after tightening bolt 128 is tightened.

FIG. 18b is an exploded view of an exemplary fitted base component 140. Rocker bolt assemblies 160 are made of hollow threaded socket 164 with u-shaped upper portion 167 adapted to receive contoured horizontal rod 169, threaded hex bolt component 162 with convex collar washer 170 and concave funnel-shaped washer 171, and pivot pin 168. Pivot pin 168 is shown on hollow threaded socket 164 and secures contoured horizontal rod 169 to hollow threaded socket 164. Rocker bolt assemblies 160 rest in rocker bolt apertures 152 of first convex plate 135 and are unable to fall through rocker bolt apertures 152 because of contoured horizontal rod 169.

Hollow threaded socket 164 projects into radial tubular portions 124a, 124b, 124c of concave base plate 136, allowing threaded hex bolt component 162 to tighten within hollow threaded socket 164. Convex collar washer 170 and concave funnel-shaped washer 171 are secured between hollow threaded socket 164 and threaded hex bolt component 162.

In the exemplary embodiment shown, there are three rocker bolt assemblies 160, and radial tubular portions 124a (not shown), 124b, 124c (not shown), with corresponding rocker bolt apertures 152, are symmetrically arranged around concave base plate 136 and first convex plate base 135, respectively. In further exemplary embodiments, additional rocker bolt assemblies 160 may be used, and radial tubular portions 124 and rocker bolt apertures 152 may be unevenly distributed around the perimeter of concave base plate 136 and first convex plate base 135.

Base plate apertures 185a, 185b and securing bolt apertures 192a, 192b are also shown in fitted base component 140. Base plate bolts 184a, 184b (not shown) project through base plate apertures 185a, 185b and corresponding base plate apertures 187a (not shown), 187b (not shown) on non-pivotal front limb engaging panel 120 (not shown) to secure non-pivotal front limb engaging panel 120 (not shown) to fitted base component 140. Similarly, securing bolts 190a (not shown), 190b (not shown) project through securing bolt apertures 191a (not shown), 191b (not shown) on non-pivotal front limb engaging panel 120 and securing bolt apertures 192a, 192b to provide additional support in securing fitted base component 140 to rigid socket assembly 210 (not shown).

Rocker bolt assemblies 160 secure first convex plate base 135 to concave plate base 136. In the exemplary embodiment shown, concave plate base 136 is adapted to receive the lower surface of first convex plate base 135.

Figures 19A, 19B:
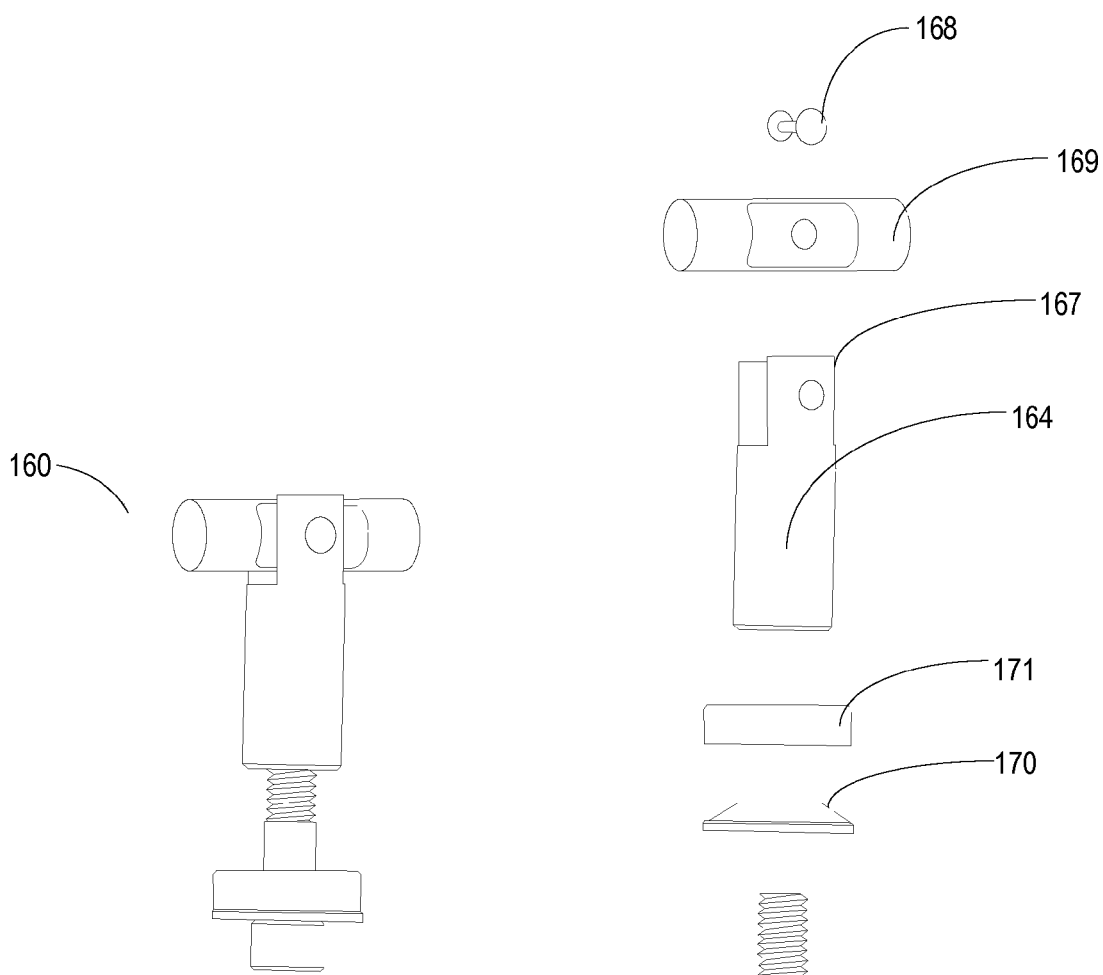
FIG. 19a illustrates an exemplary embodiment of a rocker bolt assembly.
FIG. 19b illustrates an exploded view of an exemplary embodiment of a rocker bolt assembly.

FIGS. 19a and 19b illustrate an exemplary rocker bolt assembly 160 in more detail. As illustrated, rocker bolt assembly 160 is comprised of pivot pin 168, contoured horizontal rod 169, hollow threaded socket 164 with u-shaped upper portion 167, concave funnel-shaped washer 171, convex collar washer 170 and threaded hex bolt component 162.

Pivot pin 168 pivotally secures contoured horizontal rod 169 to hollow threaded socket 164. Contoured horizontal rod 169 is therefore allowed to pivot relative to hollow threaded socket 164. In the exemplary embodiment shown, horizontal rod 169 can pivot up to 120 degrees relative to hollow threaded socket 164. Threaded hex bolt component 162 screws into hollow threaded socket 164, with concave funnel-shaped washer 171 and convex collar washer 170 secured between threaded hex bolt component 162 and hollow threaded socket 164. The construction of rocker bolt assembly 160 allows for limited movement between first convex base plate 135 and concave base plate 136.

In further exemplary embodiments, contoured horizontal rod 169 may be secured to hollow threaded socket 164 with a different securing structure. For example, contoured horizontal rod 169 may be friction fit or use a spring-pin mechanism or other structure which may pivotally secure horizontal rod 169 to hollow threaded socket 164. Different constructions of rocker bolt assemblies 160 may allow for increased movement or pivoting.

Figure 20A:
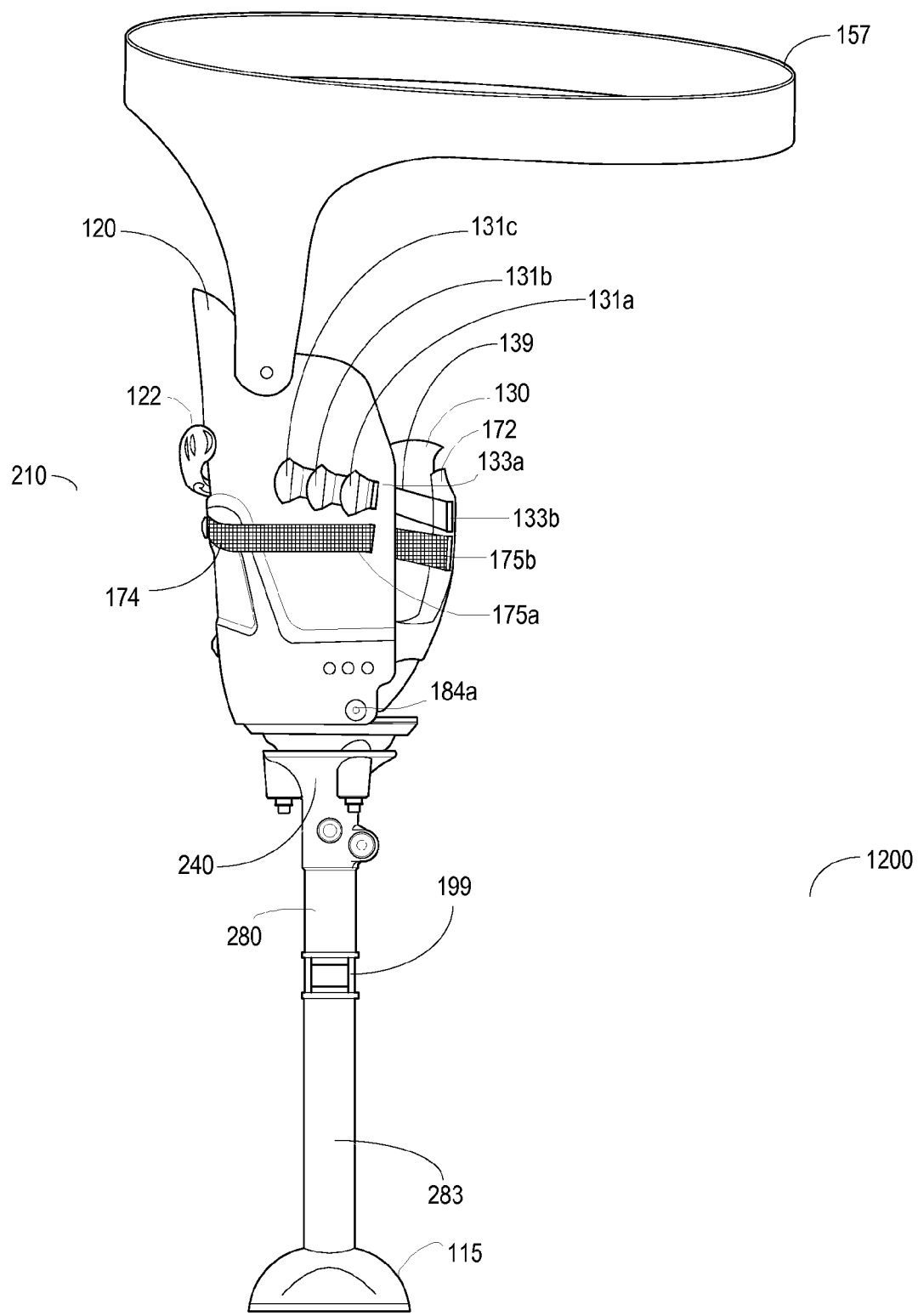
FIG. 20a is an exemplary embodiment of a rapid fit modular prosthetic device/prosthesis system for accommodating gait alignment and residual limb shape and volume for an above-the-knee residual limb.

FIG. 20a illustrates an exemplary embodiment of rapid fit modular prosthetic device for accommodating gait alignment and residual limb shape and volume adapted for an above-the-knee residual limb 1200. As illustrated, rapid fit modular prosthetic device for accommodating gait alignment and residual limb shape and volume for an above-the-knee residual limb 1200 is very similar to rapid fit modular prosthetic device for accommodating gait alignment and residual limb shape and volume for a below-the-knee residual limb 1100. However, the components of rigid socket assembly 210 may be larger to accommodate the larger size of an above-the-knee residual limb, and prosthetic device 115 includes knee 199. The entire rapid fit modular prosthetic device for accommodating gait alignment and residual limb shape and volume 1200 is also rotated 90 degrees compared to the orientation for a below-the-knee residual limb.

Rapid fit modular prosthetic device for accommodating gait alignment and residual limb shape and volume 1200 also includes waist strap 157 to help stabilize and secure rapid fit modular prosthetic device for accommodating gait alignment and residual limb shape and volume 1200.

In the exemplary embodiment illustrated in FIG. 20a, front limb engaging panel 120 and rigid outer support rib 172 are larger to accommodate a larger residual limb. Front limb engaging panel 120, specifically, needs to be taller in order to properly secure an above-the-knee residual limb. In the exemplary embodiment shown, non-pivotal front limb engaging panel 120 is 6 cm higher. Because of the way pressure is exerted on rapid fit modular prosthetic device for accommodating gait alignment and residual limb shape and volume 1200 by an above-the-knee residual limb, additional stabilizing is needed by front limb engaging panel 120. In other exemplary embodiments, rigid outer support rib 172 may be larger or of a more flattened shape to reduce projection between the legs.

In some exemplary embodiments, cable apertures 133a, 133b and securing strap apertures 175a, 175b may be positioned differently on front limb engaging panel 120 and rigid outer support rib 172 to create additional stability in securing rapid fit modular prosthetic device for accommodating gait alignment and residual limb shape and volume 1200 to a larger residual limb.

As illustrated, rapid fit modular prosthetic device for accommodating gait alignment and residual limb shape and volume 1200 contains an intricate strap/buckle system identical to that of rapid fit modular prosthetic device for accommodating gait alignment and residual limb shape and volume 1100. However, in further exemplary embodiments, rapid fit modular prosthetic device for accommodating gait alignment and residual limb shape and volume 1200 may contain additional looped cables 139, securing straps 174, buckles 122 or other securing members.

In the exemplary embodiment shown, looped cable 139 is looped around hook-shaped cable protuberance 131b, which creates a larger volume inside the recess created by non-pivotal front limb engaging panel 120 and pivotal rear limb engaging panel 130. In further exemplary embodiments, looped cable 139 may be secured using any of hook-shaped cable protuberances 131a, 131b, 131c.

Figure 20B:
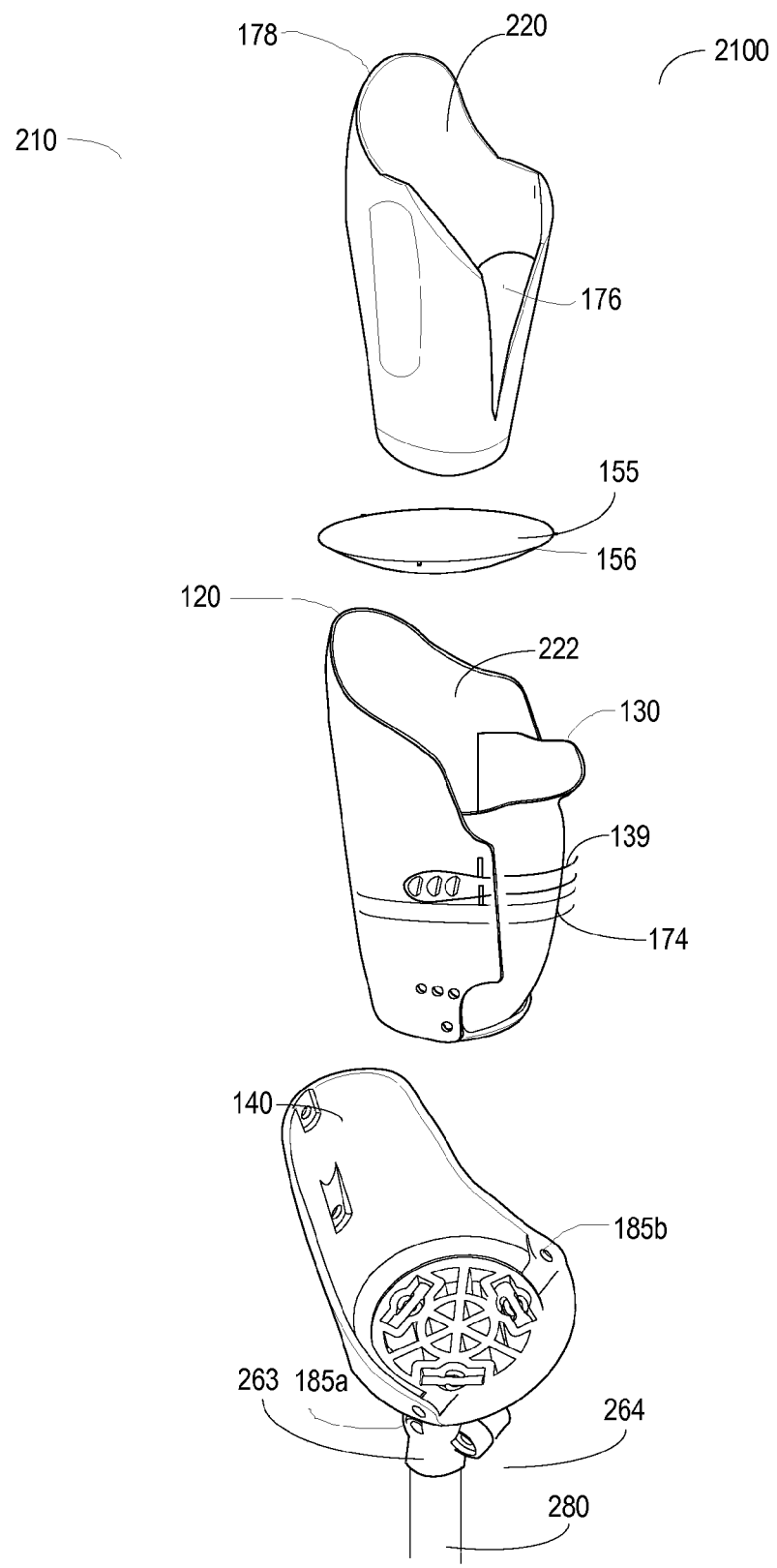
FIG. 20b is an exploded view of the above-the-knee components of an exemplary rapid fit modular prosthetic device for accommodating gait alignment and residual limb shape and volume.

FIG. 20b illustrates additional differences between rapid fit modular prosthetic device for accommodating gait alignment and residual limb shape and volume for above-the-knee residual limbs 1200 and rapid fit modular prosthetic device for accommodating gait alignment and residual limb shape and volume 1100 for below-the-knee residual limbs.

As illustrated, deformable inner liner 178 with rear tongue 176 does not contain a silicone liner. In further exemplary embodiments, deformable inner liner 178 may contain or utilize a liner made of silicone or other similar materials. Support cup 155, with support cup connectors 156, is inserted in rigid socket assembly 210 under deformable liner 178 to provide height adjustments.

In below-the-knee embodiments, the distance from a user's residual limb to the bottom of the prosthetic device is adjusted by the length of the pipe on the prosthetic device. However, in above-the-knee embodiments, the distance from a user's residual limb to the prosthetic knee must also be adjusted. Support cup 155 may be placed at any height in the tubular recess created by rigid socket assembly 210 to support a user's residual limb at the necessary height.

Support cup connectors 156 engage the interior surface of non-pivotal front limb engaging panel 120 to secure support cup 155. In the exemplary embodiment shown, support cup connectors 156 are screws which are screwed to both non-pivotal front limb engaging panel 120 and pivotal rear limb engaging panel 130. However, in further exemplary embodiments, support cup connectors 156 may be any securing structure or device known in the art, including, but not limited to, clips, clasps, braces, brackets, bolts, adhesives, friction-fit components, contours, and combinations of these and other structures. In still further exemplary embodiments, support cup 155 may be permanently, releasably or adjustably secured to rigid socket assembly 210.

In the exemplary embodiment shown, base plate apertures 185a, 185b are visible on both non-pivotal front limb engaging panel 120 and fitted base component 140. Base plate bolts 184a, 184b (not shown) project through base plate apertures 185a, 185b to secure non-pivotal front limb engaging panel 120 to fitted base component 140.

Figure 21:
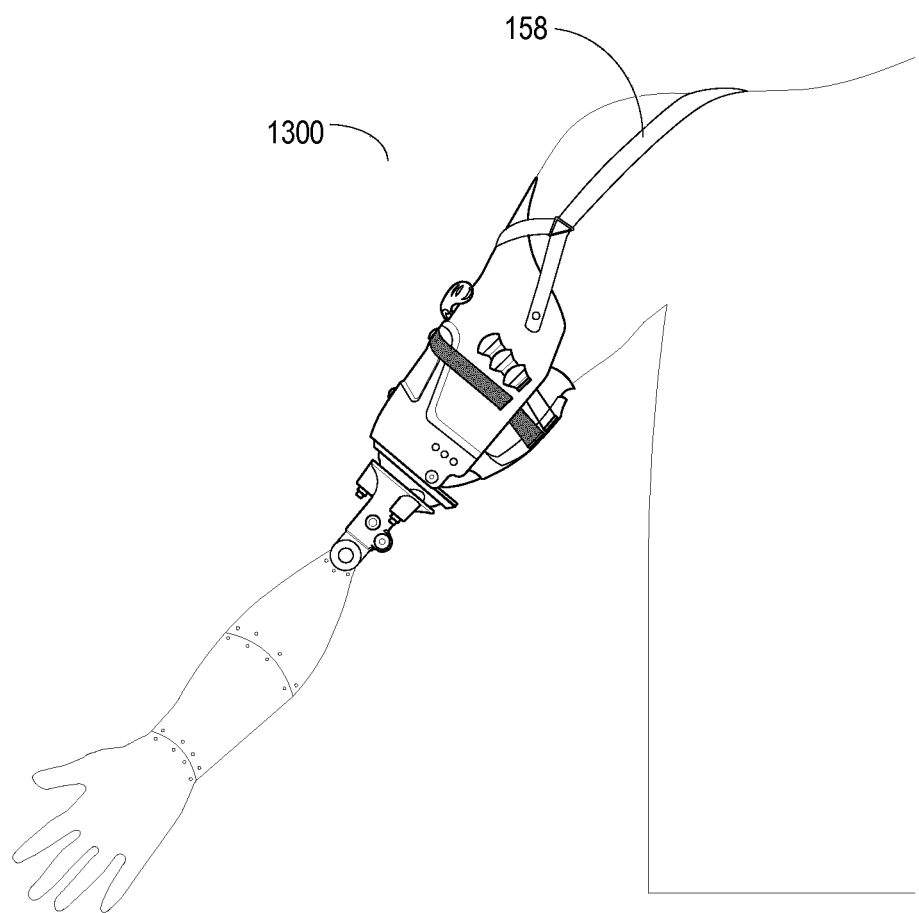
FIG. 21 illustrates an exemplary embodiment of a rapid fit modular prosthetic device for accommodating gait alignment and residual limb shape and volume adapted for use on arm-related residual limbs.

FIG. 21 illustrates rapid fit modular prosthetic device for accommodating gait alignment and residual limb shape and volume 1300 for use on a residual limb which is an arm. As illustrated, rapid fit modular prosthetic device for accommodating gait alignment and residual limb shape and volume 1300 contains basically identical structures as rapid fit modular prosthetic device for accommodating gait alignment and residual limb shape and volume 1100 for a below-the-knee residual limb 1100 and rapid fit modular prosthetic device for accommodating gait alignment and residual limb shape and volume 1200 for an above-the-knee residual limb. However, in the exemplary embodiment illustrated, rapid fit modular prosthetic device for accommodating gait alignment and residual limb shape and volume 1300 includes shoulder strap 158 to secure rapid fit modular prosthetic device for accommodating gait alignment and residual limb shape and volume 1300 to a residual limb which is an arm.

FIG. 20a illustrates an exemplary embodiment of an above-the-knee modular prosthesis system 1200. As illustrated in FIG. 20a, modular prosthesis system 1200 includes universal outer housing 210, consisting of soft inner liner 220 (not shown) and outer shell 120.

Closure components 139, 174 on outer shell 120 allow outer shell 120 to be adjusted to the circumference of an amputee's residual limb. In the exemplary embodiment shown, closure component 139 is a looped wire running from buckle 122 to secure around one of hook-shaped protuberances 131b, and closure component 174 is a strong non-elastic strap completely encircling outer shell 120 and serves as a safety strap. In further exemplary embodiments, outer shell 120 may contain any number of closure components, and closure components may be any structure or device known in the art to allow width adjustability of outer shell 22. For example, closure components may include, but are not limited to, buttons, snaps, clasps, clips, elastic components, buckles, laces, ties, interlocking components, hook-and-loop fasteners, hook-and-eye fasteners, hook-shaped components, and any combination of these and other structures and devices.

Universal outer housing 210 releasably secures to connector assembly 240 and connecting tube 280. Suspension component 157, which in the exemplary embodiment shown is a waist strap, helps an amputee more securely hold modular prosthesis system 1200 to a residual limb. In further exemplary embodiments, suspension component 157 may be any adjustable securing component or device known in the art, including, but not limited to, suspenders, belts, clasps or other attachment means which releasably attach to a user's clothing or existing belt, or any combination of these and other structures.

In some exemplary embodiments, suspension component 157 may contain additional elements to create a suspension system. For example, a liner or sleeve which fits over a residual limb may be provided with suspension component 157. In further exemplary embodiments, a liner or sleeve may include a cushioning gel substance or other component. In still further embodiments, a liner or sleeve may contain directionally frictional materials which allow the liner or sleeve to easily slide into outer housing 210, but require additional force to be removed from outer housing 210.

In yet further exemplary embodiments, outer housing 210 and connector assembly 240 may be adapted to accommodate a liner or sleeve with a serrated pin suspension system, such as the ALPS pin and gel liner suspension system known in the art.

In the exemplary embodiment shown, universal outer housing 210 is a single unit constructed of rigid plastic. In further exemplary embodiments, outer housing 210 may be multiple separate components molded or joined together, such as with closure components 139, 174. In still other exemplary embodiments, outer housing 210 may be constructed of a stronger material, such as metals, or materials specifically designed to withstand the pressure and wear caused by an amputee's activities. Closure components 139, 174 may be selected based on the material of outer housing 210 or the specific forces generated by an individual amputee's residual limb.

In the exemplary embodiment shown in FIG. 20a, connector tube 280 connects to prosthetic knee 199, which connects to below-the-knee shank 283, which is a standard below-the-knee shank known in the art and provides height adjustment for the distance from knee 199 to the prosthetic device 115 which contacts the ground.

Figure 22:
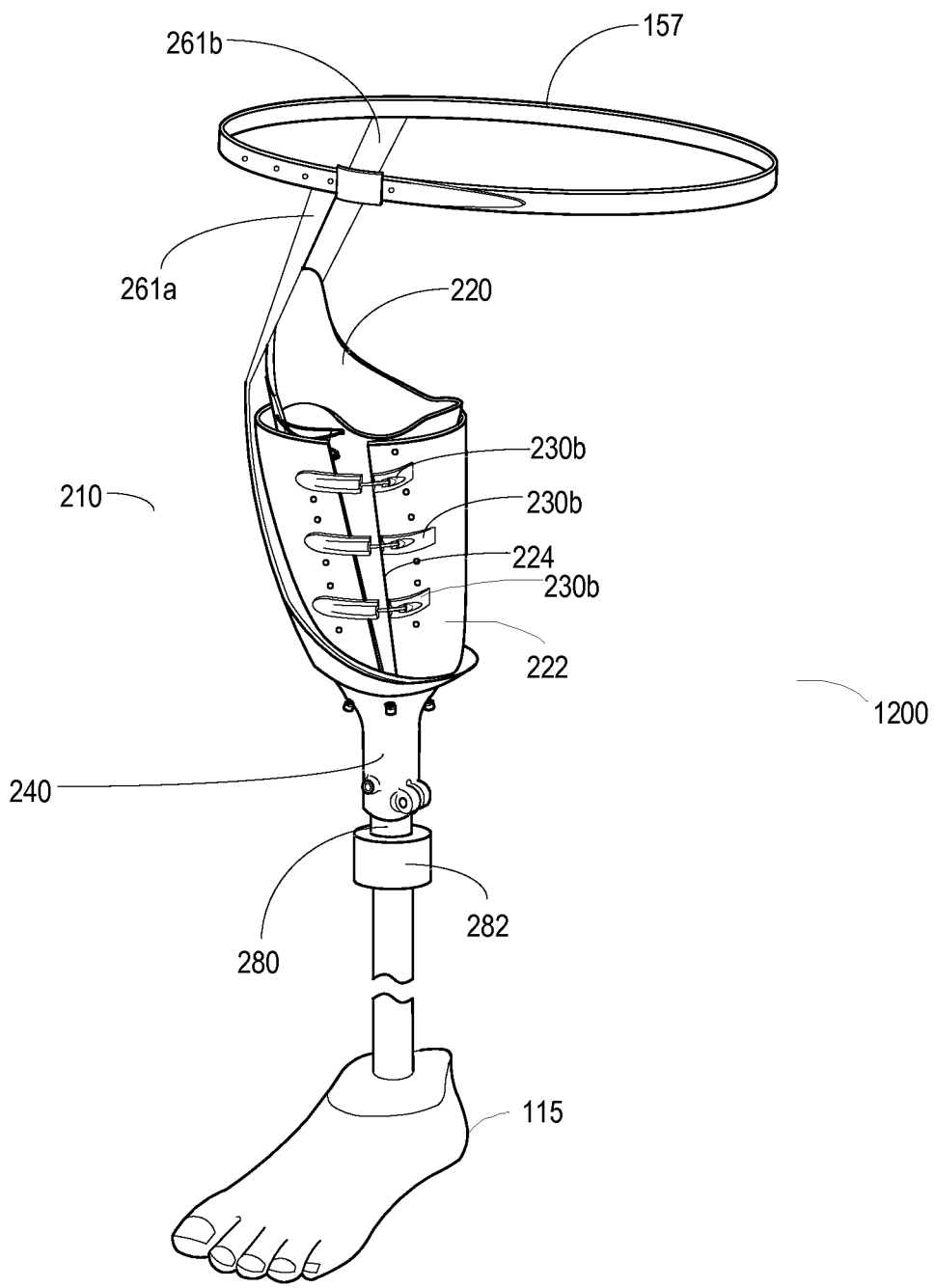
FIG. 22 illustrates an alternative embodiment of an above-the-knee modular prosthesis system with soft inner liner.

FIG. 22 illustrates an alternative embodiment of an above-the-knee modular prosthesis system 1200 with soft inner liner 220. In the exemplary embodiment shown, soft inner liner 220 fits within the cavity created by outer shell 222 and provides comfortable support for a residual limb. Soft inner liner 220 may also decrease the internal volume of the cavity created by outer shell 222 to help accommodate a residual limb having a smaller circumference.

In the exemplary embodiment shown, inner liner 220 is created of a deformable material, such as cushion, foam, gel or other pillow-like material which deforms to specifically contour a residual limb. In other exemplary embodiments, inner liner 220 may be custom-made to fit a specific residual limb.

As illustrated in FIG. 22, suspension component 157 is a belt with two side straps 261a, 261b which attach to outer housing 210. In other exemplary embodiments, side straps 261a, 261b may be attached to inner liner 220.

In the exemplary embodiment shown, outer housing 210 contains three identical closure components 230b which are buckles. Closure components 230b tighten against outer shell 222 to close gap 224 and apply pressure around a residual limb to keep it in outer housing 210. In further exemplary embodiments, closure components may each be different. In yet further exemplary embodiments, closure components may be specifically designed or positioned to apply pressure at specific points around a residual limb.

Outer housing 210 attaches to connector 240, which in the exemplary embodiment shown is adjustable for making angular adjustments. For example, connector 240 may be able to tilt backwards, forwards and/or to the sides to account for differences in an individual's gait and natural bone alignment. Connector 240 provides adjustment of the angle of the prosthesis and leg on the amputee to optimally align the prosthesis. After it is adjusted and put into the proper position angle, connector 240 is tightly secured in place such that it provides a stable and non-movable attachment for safe ambulation.

Connector 240 attaches outer housing 210 to connector pipe 280, which is a standard diameter pipe connector known in the art. In the exemplary embodiments shown in FIGS. 20a and 22, connector 280 is drawn attached to knee component 282, which connects via shank 283 to a foot-like prosthetic limb. In further exemplary embodiments, shank 283 may be any prosthetic shank known in the art.

Figure 23:
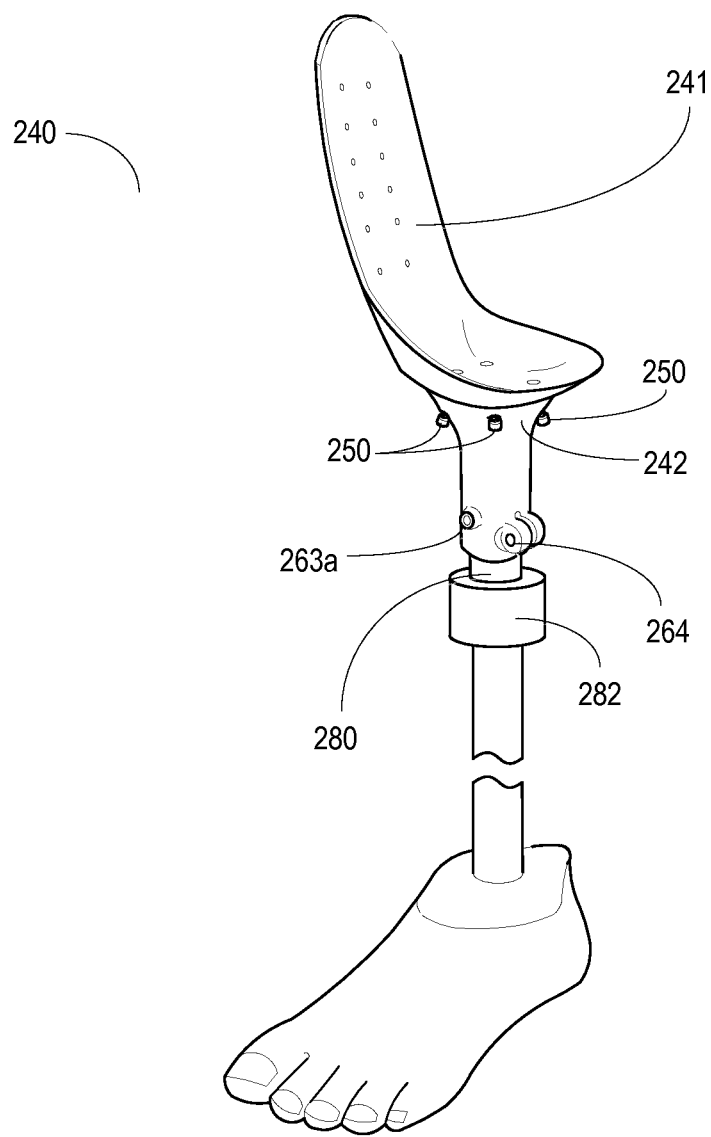
FIG. 23 illustrates an exemplary connector assembly for a modular prosthesis system.

FIGS. 23 and 18a illustrate exemplary connector assemblies 240, 140 for a modular prosthesis system 1200.

As illustrated in FIG. 23, connector assembly 240 includes upper plate 241 and lower plate 242 joined by bolts 250. Lower plate 242 contains an inner tubular recess for receiving connector pipe 280. Set screws 263a and 263b (not shown) and tightening bolt 264 help tighten connector pipe 280 to connector assembly 240.

Bolts 250 allow for gait adjustability. When a residual limb is secured in outer housing 210 (not shown), outer housing 210 (not shown) is securely attached to upper plate 241. Upper plate 241 and lower plate 242 may be pivotally adjustable, relative to each other, to conform modular prosthesis system 1200 to a specific individual. In further exemplary embodiments, upper plate 241 and lower plate 242 may contain a limited degree of rotational adjustability. Bolts 250 allow an amputee to account for differences in bone structure, curvature, and alignment.

FIG. 18b is an alternative exemplary connector assembly 140. Upper plate 241 connects to lower plate 136 using specialized bolts comprised of a hollow, pivotal female end 248 with threaded male end 162. Washers 171 may be optionally included with male end 162. Pivotal female ends 248 project downwards through bolt apertures 152, and male ends 162 project upwards through corresponding bolt channels 124a to engage female ends 248. Pivotal female ends 248 allow limited movement and adjustability of upper plate 241 relative to lower plate 136.

In the exemplary embodiment illustrated, once a desired position has been reached, the pivotal bolts assemblies may be tightened into place, permanently or adjustably, to prevent upper plate 241 and lower plate 136 from moving under the forces exerted by a residual limb and movement of an amputee. In further exemplary embodiments, upper plate 241 and lower plate 136 may be secured together with a limited amount of allowable movement for such things as absorbing excessive gait forces.

While upper plate 241 and lower plate 136 are illustrated as joined by three pivotal bolt assemblies, in further exemplary embodiments, upper plate 241 and lower plate 136 may be adjustably attached through any structure or device known in the art, including, but not limited to, screws, pins, bolts, interlocking components, or any combination of these and other structures or devices.

Both FIGS. 23 and 18b show different structures to provide limited adjustability of modular prosthetic system 1200 to account for differences in bone structure, shape and alignment, as well as differences in gait, to create a custom-like fit for each amputee.

In some exemplary embodiments, as illustrated in FIG. 18b, upper plate 241 and/or lower plate 136 may contain surface textures which may facilitate or incrementally limit the adjustability of connector assembly 240. As shown in FIG. 18b, lower plate 136 contains a grid pattern which corresponds to a similar grid pattern on the under-surface of upper plate 241. The corresponding grid patterns create a plurality of locations to which connector assembly 240 may be positioned. When the grid-like surfaces connect, the position is more stable and resistant to change when experiencing the various forces applied to connector assembly 240 by a residual limb and the general movement of an amputee.

FIG. 20*b* is an exploded view of an exemplary above-the-knee modular prosthesis system 1200. Soft inner liner 220 is removed from outer shell 222. In some exemplary embodiments, soft inner liner 220 may contain closure components, such as laces, buckles, hook-and-eye fasteners, hook-and-loop fasteners or other structures or combinations of structures known in the art to secure soft inner liner 220 around a residual limb. As illustrated, outer shell 222 contains closure components 139, 174, which are a looped cable and securing band, as shown in FIG. 20*a*. Height adjustment component 155 is shown between inner liner 220 and outer shell 222. Connector assembly 140 contains connector 280, rotationally and vertically secured in place by set screw 263 and tightening bolt 264.

In the exemplary embodiment shown, height adjustment component 155 is a plate which may be positioned within outer shell 222 to adjust for the distance between a residual limb and the natural location of a knee joint. As illustrated, height adjustment component 155 is friction-fit within outer shell 222. In further exemplary embodiments, height adjustment component 155 may contain pins, bolts, or other structures adapted to project through outer shell 222, creating a more permanent adjustment. In still further exemplary embodiments, outer shell 222 may contain a plurality of pre-determined height-adjustment locations to which height adjustment component 155 may be secured.

In further exemplary embodiments, height adjustment component 155 may also be used to adjust to the angle of a residual limb and therefore alter the angle at which modular prosthetic system 1200 is attached. For example, height adjustment component 155 may be pivotally attached to outer shell 222, or secured to outer shell 222 at an angle.

In some exemplary embodiments, height adjustment component 155 may be made of a solid material, such as plastics or metals. In further exemplary embodiments, height adjustment component 155 may contain a form of cushioning or padding to decrease the pressure on a residual limb. However, height adjustment component 155 will need to be able to support the weight of an amputee.

In further exemplary embodiments, when height adjustment is not necessary, height adjustment component 155 may be omitted. In yet further exemplary embodiments, an additional cushion or padded component may be placed between inner liner 220 and outer shell 222.

In yet further exemplary embodiments, inserts and adjustment components of various shapes, sizes and contours may be added to adjust for a residual limb's circumference, volume, size, angle, and other properties. For example, modular prosthetic system 1200 may include height adjustment components, volume adjustment components, angle adjustment components, circumference adjustment components and combinations of such adjustment components. By providing modular adjustment components, modular prosthetic system 1200 may be manufactured in a standard size, or select standard sizes, yet adjusted to provide a near custom fit for each residual limb. For example, universal outer housing 210 may be manufactured in three sizes, with variations in soft inner liner 220 and height adjustment component 155 and the adjustability provided by closure components 139, 174 and other components creating a wide range of sizes.

In the exemplary embodiments described, components of modular prosthetic system 1200 may be disposable. For example, the various liners, pads and adjustment components may be specifically designed to be quickly and easily changed and disposable as an amputee's residual limb changes size or shape. In other exemplary embodiments, components of modular prosthetic system 1200 which experience wear may be designed to be replaced and disposed as they weaken.

In other exemplary embodiments, components of modular prosthetic system 1200 may be specifically designed and manufactured for efficient shipping. For example, liners, shells and other components may be specifically designed to nest within each other, saving room during shipping. Other components, such as bolts, screws and closure components, may also be assembled for shipping.

Modular prosthetic system 1200 also allows a prosthetic limb to be quickly and securely attached to a residual limb. The adjustability of the various components provides a quick way to create a custom-like fit by accounting for differences in residual limb shape, circumference, volume and general size, as well as differences in gait, bone structure and bone alignment. Because it is not necessary to create custom pieces or molds, modular prosthetic system 1200 may be implemented immediately.

Another exemplary embodiment of Applicant's adjustable prosthesis system 1400 is illustrated in FIGS. 24-28. The system includes an outer shell 310, one or more closure components (not shown), such as a strap(s), buckle(s), or clasp(s), an inner liner 378, and an adjustable connector assembly 340, which connects the adjustable outer shell 310 to a shank 332 or another prosthetic device in a manner discussed in more detail below in view of FIGS. 28A and 28B. The system also may include a locking pin 386 and a locking mechanism 395, which also are discussed below in connection with the connector assembly 340 illustrated in FIGS. 28A and 28B.

Figures 26A, 26B:
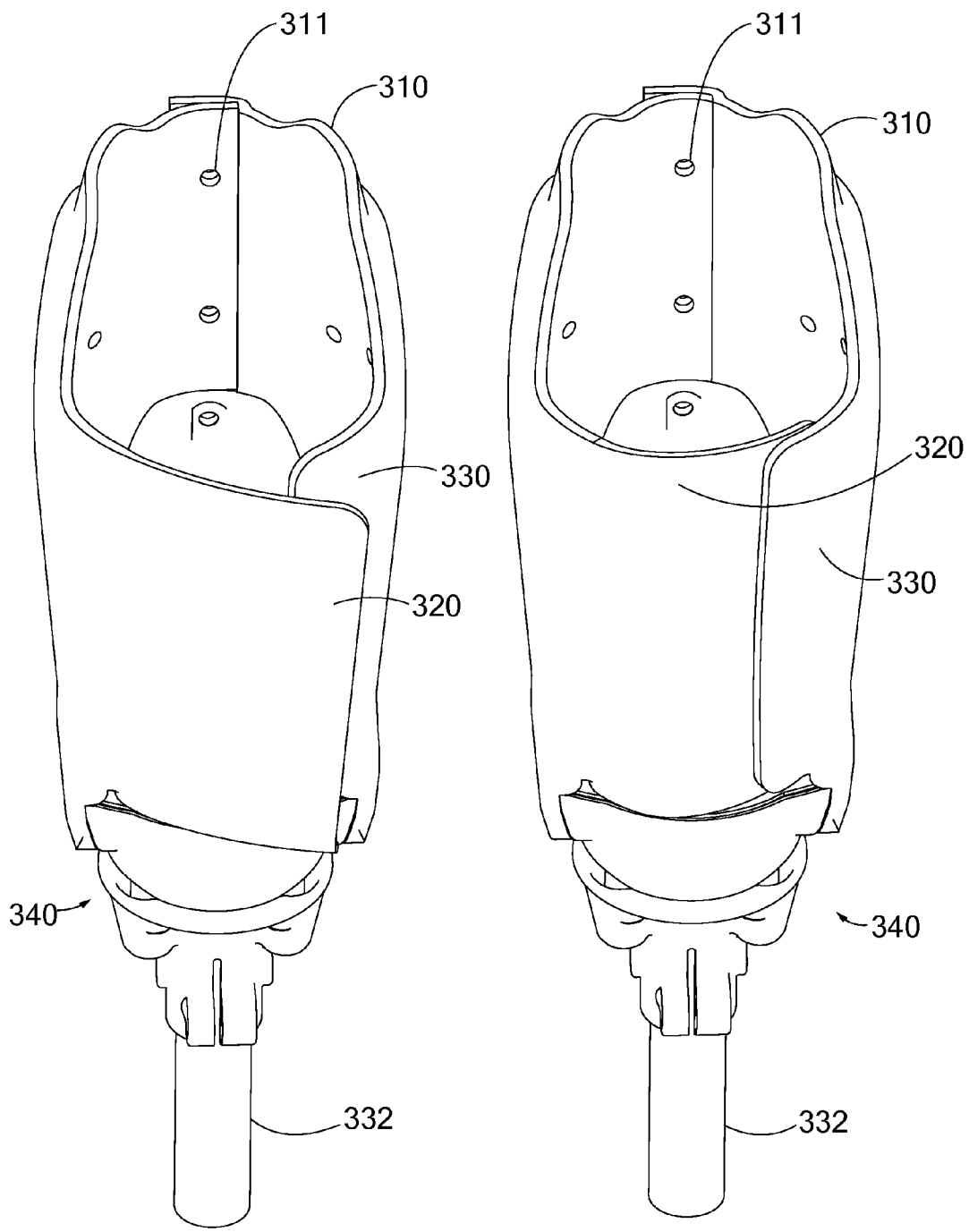
FIG. 26A illustrates a perspective view of an exemplary embodiment of an outer shell connected to a shank by a connector for use in an adjustable prosthesis system.
FIG. 26B illustrates a perspective view of another exemplary embodiment of an outer shell connected to a shank by a connector for use in an adjustable prosthesis system.
Figure 27B:
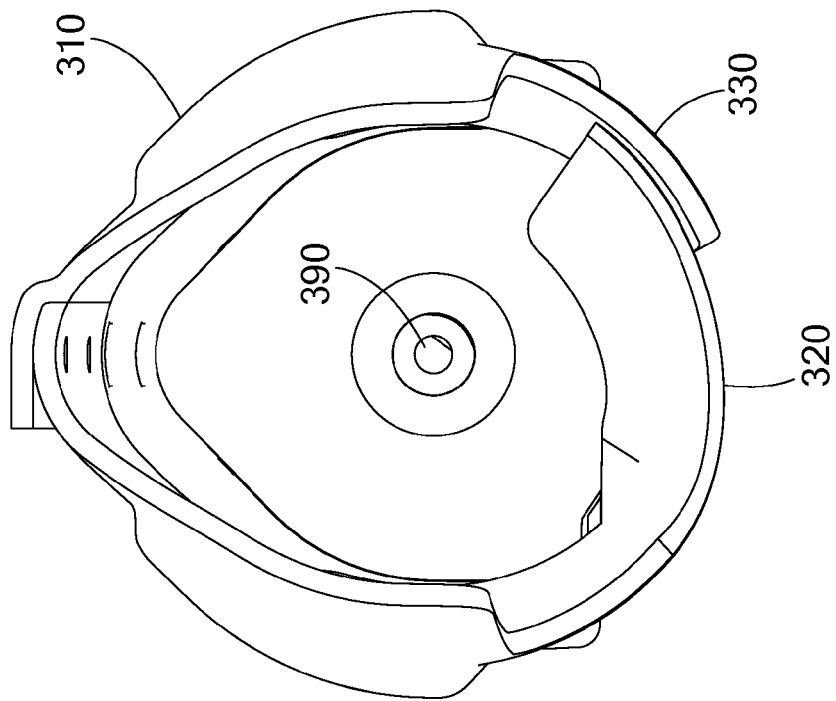
FIG. 27B illustrates a perspective top view of the exemplary embodiment of the outer shell illustrated in FIG. 26B.
Figure 27A:
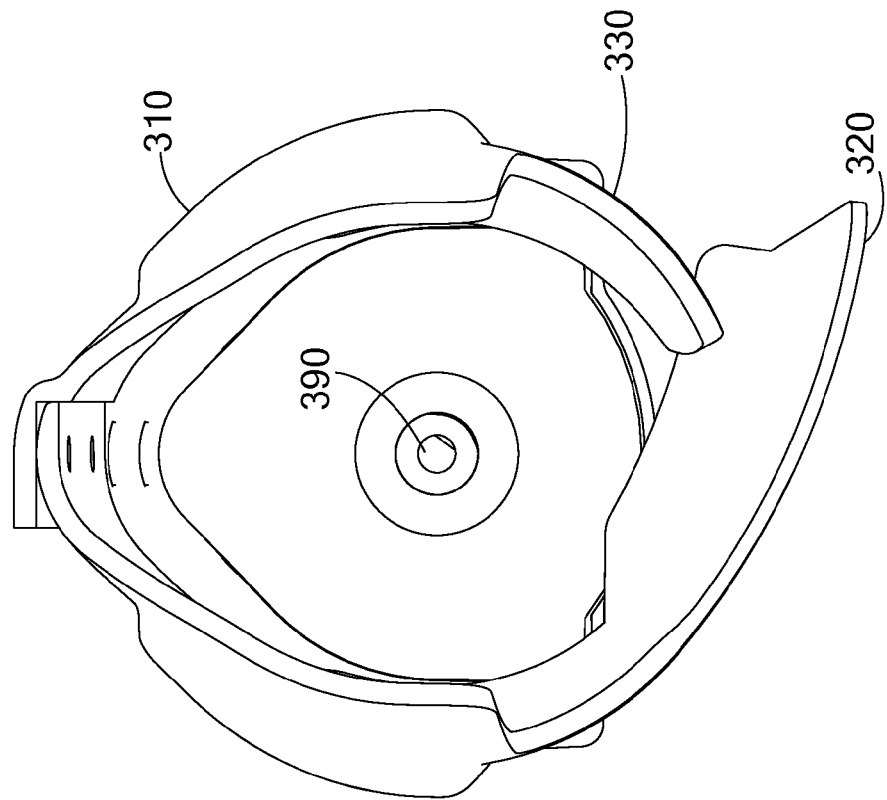
FIG. 27A illustrates a perspective top view of the exemplary embodiment of the outer shell illustrated in FIG. 26A.

The inner liner 378, which receives a residual limb, is inserted into the adjustable outer shell 310, which is primarily (substantially) constructed of a flexible material or a stiff material with flexible regions. In this embodiment, the outer shell 310 has two opposing, overlapping flaps 320, 330, as illustrated in FIGS. 26A, 26B, 27A and 27B. As shown in those figures, one flap 320 is longer than the other flap 330 in this exemplary embodiment. During use, the longer flap 320 may overlap the shorter flap 330, as illustrated in FIGS. 26A and 27A; or the shorter flap 330 may overlap the longer flap 320, as illustrated in FIGS. 26B and 27B. A closure component(s) (not shown) is used to hold the overlapping flaps 320, 330 in place and to tighten or loosen the adjustable outer shell 310 about the residual limb in the inner liner 378 positioned in the adjustable outer shell 310.

Optional stiffening components (not shown) may be included on the sides of outer shell 310. For example, long, narrow strips of metal or other material may be placed in a longitudinal position on the sides of the outer shell 310 shown in FIG. 26A or 26B. In one embodiment, the stiffening components may be molded in place in the flexible material of the outer shell 310. Selective stiffening parts (not shown) also may be encapsulated in the flexible material of the outer shell 310.

As shown in FIGS. 27A and 27B, a hole 390 for receiving the locking pin 386 is provided in the bottom of the adjustable outer shell 310.

Figure 28A:
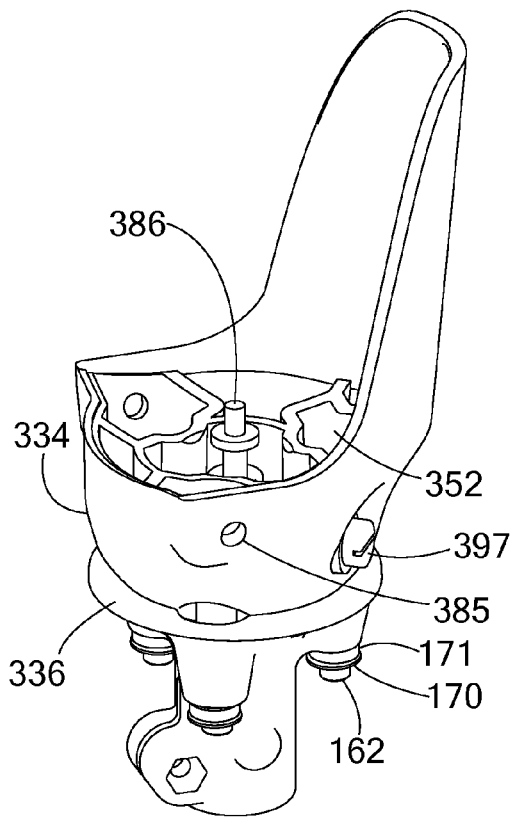
FIG. 28A illustrates a perspective view of an exemplary embodiment of a connector assembly for use in an adjustable prosthesis system.
Figure 28B:
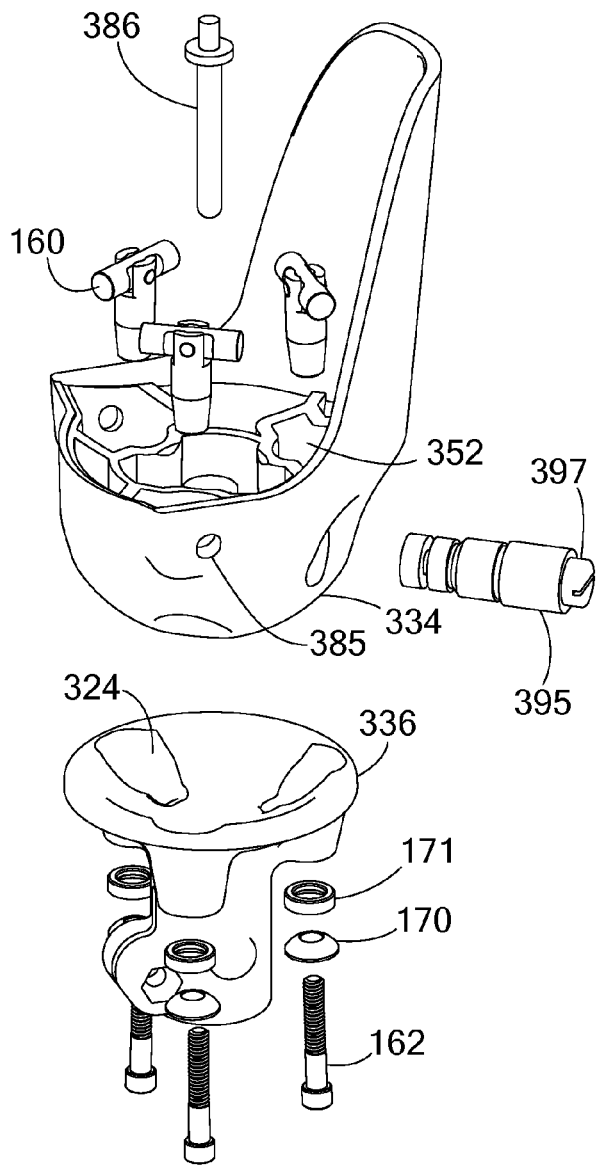
FIG. 28B illustrates a perspective exploded view of the exemplary embodiment of the connector assembly illustrated in FIG. 28A.

FIG. 28A shows the connector assembly 340 used in this exemplary embodiment. An exploded view of the connector assembly 340, as shown in FIG. 28B, shows the various components of the connector assembly 340.

Figure 25:
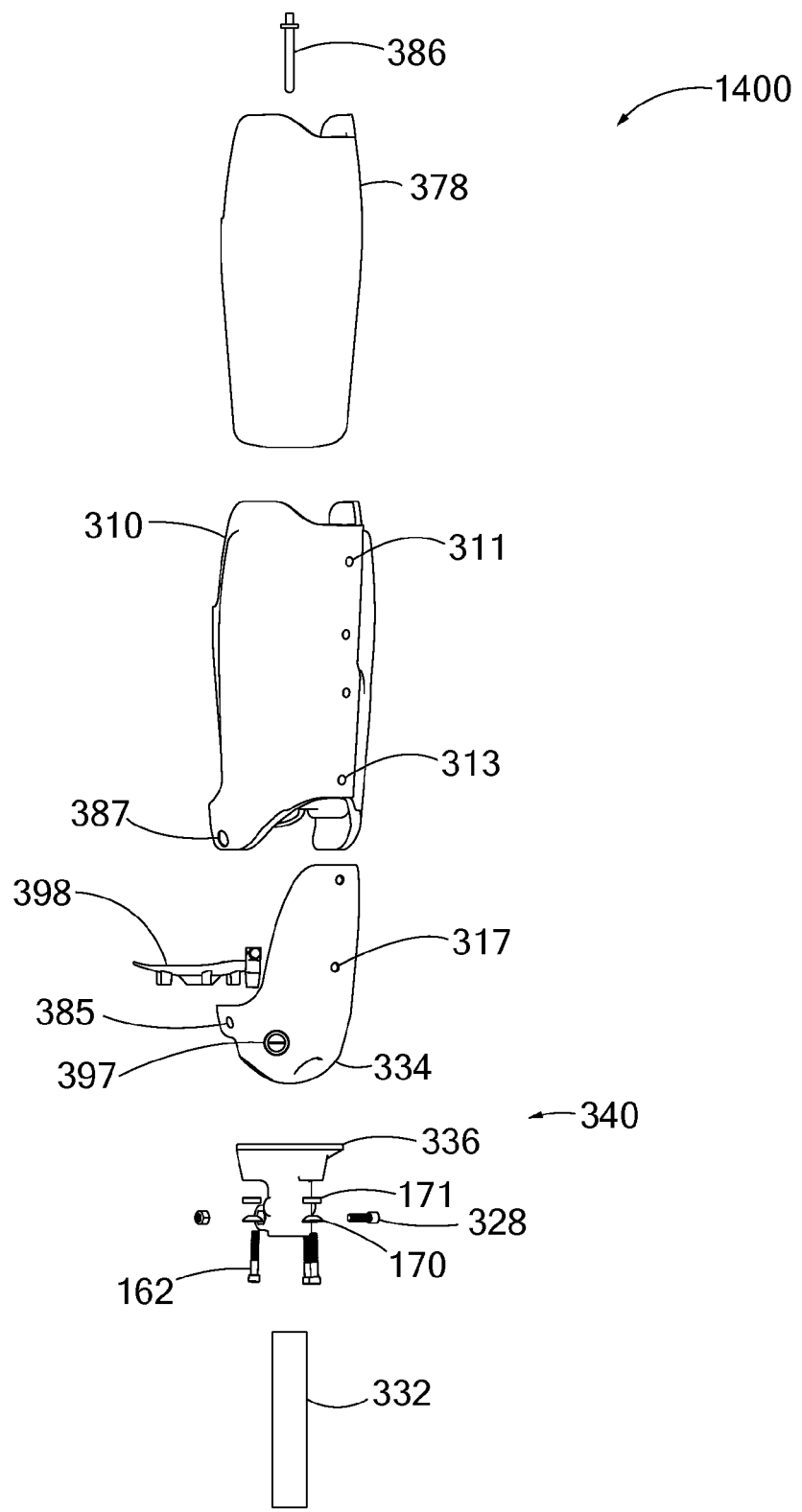
FIG. 25 is a slightly rotated view of the exemplary embodiment of the adjustable prosthesis system illustrated in FIG. 24.

The connector assembly 340 includes an upper plate 334 having a convex bottom surface and a lower plate 336 having a concave upper surface to receive the convex bottom surface of the upper plate. The upper plate 334 is connected to the outer shell 310 by a fastener(s) (not shown) at apertures 385 and 387. In addition, as shown in FIG. 25, the two apertures 317 on the back of plate 334 are connected by fasteners (not shown) to the two lower apertures 313 on the back of outer shell 310. Fasteners (not shown) connect the two sides of the outer shell 310 at the two upper apertures 311.

Rocker bolt assemblies 160 fasten the upper plate 334 and the lower plate 336 in this exemplary embodiment. As previously discussed, FIGS. 19a and 19b illustrate the exemplary rocker bolt assembly 160 in more detail. As explained in that previous discussion, each rocker bolt assembly 160 receives a threaded bolt component 162 with convex collar washer 170 and concave funnel-shaped washer 171. Rocker bolt assemblies 160 rest in rocker bolt apertures 352 of the upper plate 334 and are unable to fall through rocker bolt apertures 352 because of the horizontal rod 169 (FIG. 19b).

Hollow threaded socket 164 projects into aperture 324 on the lower plate 336, allowing threaded hex bolt component 162 to tighten within hollow threaded socket 164. Convex collar washer 170 and concave funnel-shaped washer 171 are secured between hollow threaded socket 164 and threaded hex bolt 162.

In the exemplary embodiment illustrated in FIGS. 28A and 28B, there are three rocker bolt assemblies 160. In further exemplary embodiments, additional rocker bolt assemblies 160 may be used.

The locking pin 386 is guided into the bottom of the adjustable outer shell 310 and into the hole 390 (see FIGS. 27A and 27B) where it engages the locking mechanism 395, which in the embodiment shown is a one-way clutch. The one-way clutch prevents the locking pin 386 from being pulled out (and prevents the residual limb from coming out also). The locking mechanism 395 is released by pushing on the button 397, which releases the locking pin 386. Persons skilled in the art will recognize that the locking mechanism 395 (one-way clutch) may be operated by means other than pushing a button 397, such as twisting a knob.

Figure 24:
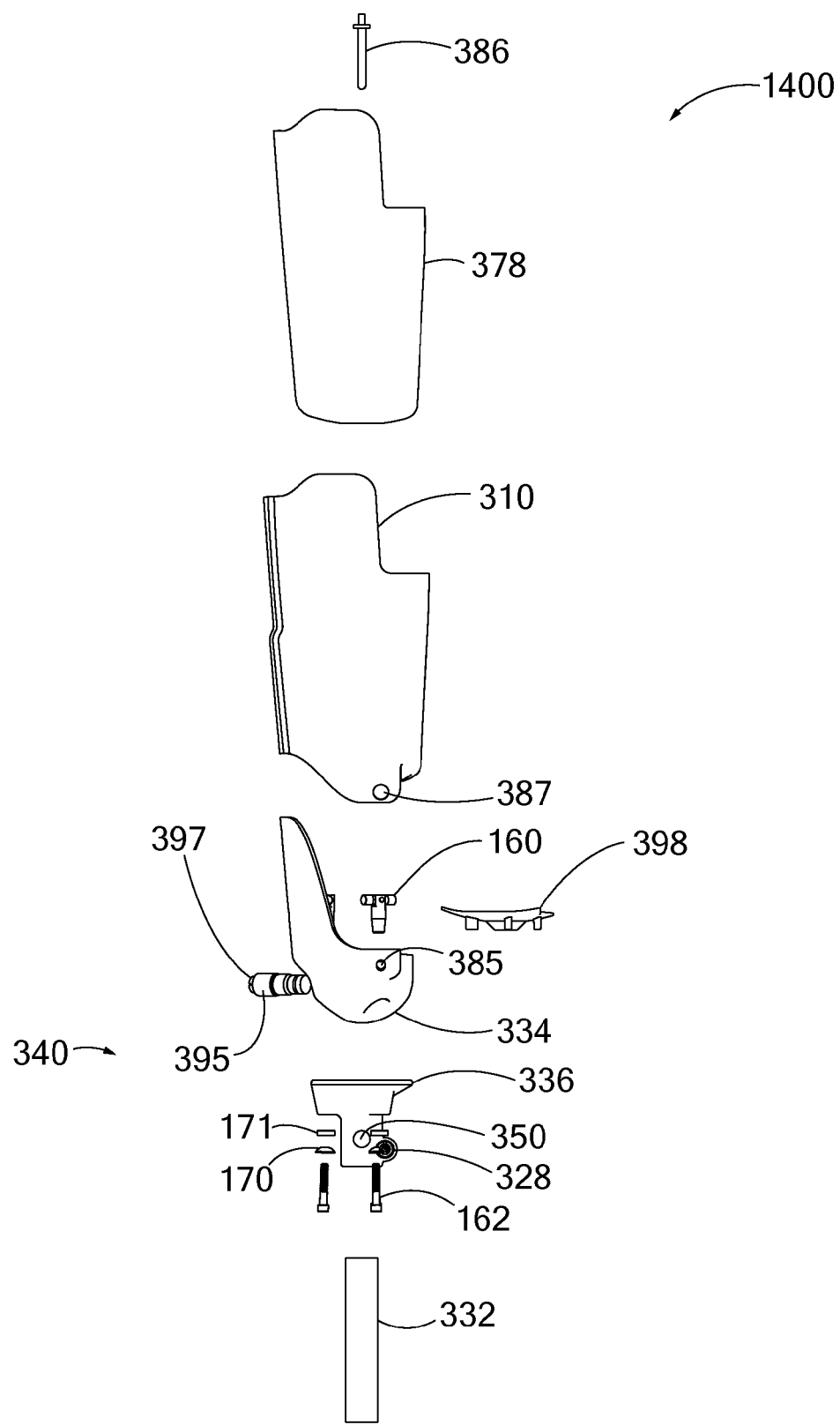
FIG. 24 illustrates a perspective exploded view of an exemplary embodiment of an adjustable prosthesis system.

As shown in FIGS. 24 and 25, a bottom plate 398 is positioned between the bottom of the outer shell 310 and the connector assembly 340 to accommodate the locking pin 386 suspension system and cover the rocker bolts 160.

As also shown in FIGS. 24 and 25, a fastener 328, such as a bolt and nut in the exemplary embodiment, is used to clamp the lower plate 336 of connector assembly 340 to the shank 332. Optional set screws (not shown) may be inserted in aperture 350 and an other aperture (not shown) on the opposite side of plate 336 to be used to adjust the positioning of the shank 332.

In the exemplary embodiments shown in the drawings and discussed in the Detailed Description, various fasteners and adjustment components are used, including bolts, nuts, screws, washers, sets screws, etc. Persons skilled in the art will recognize that other types of fasteners and adjustment components could be used as well instead of those shown and discussed. Similarly, various types of components used for closing, tightening, and securing are illustrated and discussed, including straps, looped cables, laces, buckles, cable protuberances, buttons, snaps, clasps, clips, elastic components, ties, interlocking components, hook-and-loop fasteners, hook-and-eye fasteners, hook-shaped components, and any combination of these and other structures and devices. Persons skilled in the art will also recognize that other types of closing, tightening, and securing components also could be used as well instead of those shown and discussed.

Applicant's systems and devices include many other embodiments and variations thereof which are not illustrated in the drawings or discussed in the Detailed Description section. Those embodiments and variations, however, do fall within the scope of the appended claims and equivalents thereof.

Persons skilled in the art will recognize that the embodiments and variations illustrated in the drawings and discussed in the Detailed Description section do not disclose all of the possible arrangements of Applicant's systems and devices, and that other arrangements are possible. Accordingly, all such other arrangements are contemplated by Applicant's systems and devices, and are within the scope of the appended claims and equivalents thereof.

Persons skilled in the art also will recognize that many other embodiments incorporating Applicant's inventive concepts are possible, as well as many variations of the embodiments illustrated and described herein.

Although illustrated and described herein with reference to certain specific embodiments, Applicant's apparatus and devices are nevertheless not intended to be limited to the details shown. Rather, various modifications may be made in the details within the scope and range of equivalents of the claims without departing from the spirit of the invention.

What is claimed is:

1. An adjustable prosthesis system for a residual limb, comprising:

an adjustable flexible outer shell having an adjustable inner volume and an adjustable inner shape, wherein the adjustable outer shell comprises a first flap having a first extended end, and a second flap opposite the first flap and having a second extended end, wherein at least a portion of the first flap overlaps at least a portion of the second flap so that at least a portion of the first extended end is on top of the second flap and at least a portion of the second extended end is under the first flap;

at least one closure component attached to the adjustable flexible outer shell and adapted to adjust at least one of the adjustable inner volume and the adjustable inner shape of the adjustable flexible outer shell;

an inner liner adapted to receive the residual limb and to be inserted in the adjustable inner volume of the adjustable flexible outer shell; and an adjustable connector having a proximal end adjustably connected to a distal end of the adjustable flexible outer shell and adapted to provide concurrently for a plurality of directional adjustments and/or angular adjustments of a position of the distal end of the adjustable flexible outer shell relative to the proximal end of the adjustable connector, a distal end of the adjustable connector being adapted to connect to a shank or an other prosthetic device, wherein the adjustable connector comprises an upper plate adapted to adjustably connect to the adjustable flexible outer shell, a lower plate below the upper plate and adapted to adjustably connect to the upper plate and to a shank or an other prosthetic device, and a plurality of rocker bolt assemblies adjustably connecting the lower plate to the upper plate, wherein at least a portion of a bottom surface of the upper plate is convex and at least a portion of an upper surface of the lower plate is concave and adapted to receive at least part of the convex portion of the bottom surface of the upper plate, wherein each rocker bolt assembly has a hollow threaded socket that extends downward through one of a plurality of apertures in the bottom surface of the upper plate and further downward through one of a plurality of adjacent corresponding apertures in the upper surface of the lower plate, the hollow threaded socket adapted to receive a threaded bolt, and wherein the directional adjustments are selected from a group consisting of a forward adjustment, a backward adjustment, a side-to-side adjustment, a rotational adjustment, and combinations thereof.

2. An adjustable prosthesis system as in claim 1, wherein said at least one closure component is selected from a group consisting of buttons, snaps, clasps, clips, elastic components, buckles, laces, ties, interlocking components, hook-and-loop fasteners, hook-and-eye fasteners, hook-shaped components, looped wires, straps, and combinations thereof.

3. An adjustable prosthesis system as in claim 1, wherein the first flap has a lateral length that is longer than a lateral length of the second flap.

4. An adjustable prosthesis system as in claim 1, further comprising at least one stiffening member attached to at least a portion of the adjustable flexible outer shell.

5. An adjustable prosthesis system as in claim 1, wherein adjustment of the adjustable flexible outer shell and adjustment of the adjustable connector provide for a custom-like fit on the residual limb of the adjustable prosthesis system accounting for a plurality of differences in at least some of residual limb shape, circumference, volume, angle, general size, and other properties, as well as a plurality of differences in at least some of gait, bone structure, bone curvature, and bone alignment among a plurality of amputees.

6. An adjustable prosthesis system as in claim 1, wherein at least a portion of the inner liner is deformable.

7. An adjustable prosthesis system as in claim 1, wherein the adjustable connector is releasably attached to the adjustable flexible outer shell.

8. An adjustable prosthesis system as in claim 1, further comprising a suspension system connected to the adjustable flexible outer shell.

9. An adjustable prosthesis system as in claim 1, further comprising at least one adjustment component selected from a group consisting of a height adjustment component, a volume adjustment component, an angle adjustment component, a circumference adjustment component, and combinations thereof.

10. An adjustable prosthesis system as in claim 1, further comprising a pin suspension system with a locking pin.

11. An adjustable prosthesis system as in claim 10, further comprising a locking mechanism to lock and unlock the locking pin at a desired position.

12. An adjustable prosthesis system as in claim 11, further comprising a base plate adapted to guide the locking pin to a location adjacent the locking mechanism.

13. An adjustable prosthesis system as in claim 1, wherein at least a portion of a lower surface of the upper plate is textured and at least a portion of an upper surface of the lower plate is textured.

14. An adjustable connector for a prosthesis system, comprising:
an upper plate adapted to adjustably connect to a component of the prosthesis system adjacent a residual limb;
a lower plate below the upper plate and adapted to adjustably connect to the upper plate and to a shank or an other prosthetic device below the lower plate; and
a plurality of rocker bolt assemblies adapted to adjustably connect the lower plate to the upper plate thereby providing for an adjustable connection between the component of the prosthesis system adjacent the residual limb and the shank or an other prosthetic device,
whereby the adjustable connection provides for a concurrently made plurality of directional adjustments and/or angular adjustments of a position of the component of the prosthesis system relative to the shank or an other prosthetic device while the component of the prosthesis system is on the residual limb,
wherein each rocker bolt assembly has a hollow threaded socket that extends downward through one of a plurality of apertures in a bottom surface of the upper plate and further downward through one of a plurality of adjacent corresponding apertures in an upper surface of the lower plate, the hollow threaded socket adapted to receive a threaded bolt.

15. An adjustable connector for a prosthesis system, comprising:
an upper plate adapted to adjustably connect to a component of the prosthesis system adjacent a residual limb;
a lower plate below the upper plate and adapted to adjustably connect to the upper plate and to a shank or an other prosthetic device below the lower plate; and
a plurality of fasteners adapted to adjustably connect the lower plate to the upper plate, thereby providing for an adjustable connection between the component of the prosthesis system adjacent the residual limb and the shank or an other prosthetic device,
whereby the adjustable connection provides for a concurrently made plurality of directional adjustments and/or angular adjustments of a position of the component of the prosthesis system relative to the shank or an other prosthetic device,
wherein at least one of the fasteners is a rocker bolt assembly, and
wherein each rocker bolt assembly has a hollow threaded socket that extends downward through one of a plurality of apertures in a bottom surface of the upper plate and further downward through one of a plurality of adjacent corresponding apertures in an upper surface of the lower plate, the hollow threaded socket adapted to receive a threaded bolt.

16. An adjustable connector as in claim 15, wherein at least a portion of a lower surface of the upper plate is textured and at least a portion of an upper surface of the lower plate is textured.

17. An adjustable connector as in claim 15, wherein at least a portion of a bottom surface of the upper plate is convex and at least a portion of an upper surface of the lower plate is concave and adapted to receive at least part of the convex portion of the bottom surface of the upper plate.

18. An adjustable connector as in claim 15, wherein the directional adjustments are selected from a group consisting of a forward adjustment, a backward adjustment, a side-to-side adjustment, a rotational adjustment, and combinations thereof.

19. An adjustable connector for a prosthesis system, comprising:
an upper plate adapted to adjustably connect to a component of the prosthesis system adjacent a residual limb;
a lower plate below the upper plate and adapted to adjustably connect to the upper plate and to a shank or an other prosthetic device below the lower plate,
wherein at least a portion of a bottom surface of the upper plate is convex and at least a portion of an upper surface of the lower plate is concave and adapted to receive at least part of the convex portion of the bottom surface of the upper plate; and
a plurality of rocker bolt assemblies adapted to adjustably connect the lower plate to the upper plate, thereby providing for an adjustable connection between the component of the prosthesis system adjacent the residual limb and the shank or an other prosthetic device, whereby the adjustable connection provides for a concurrently made plurality of directional adjustments and/or angular adjustments of a position of the component of the prosthesis system relative to the shank or an other prosthetic device, wherein the directional adjustments are selected from a group consisting of a forward adjustment, a backward adjustment, a side-to-side adjustment, a rotational adjustment, and combinations thereof, and wherein each rocker bolt assembly has a hollow threaded socket that extends downward through one of a plurality of apertures in the bottom surface of the upper plate and further downward through one of a plurality of adjacent corresponding apertures in the upper surface of the lower plate, the hollow threaded socket adapted to receive a threaded bolt.

20. An adjustable connector as in claim 19, wherein at least a portion of a lower surface of the upper plate is textured and at least a portion of an upper surface of the lower plate is textured.

21. An adjustable connector for a prosthesis system, comprising:

an upper plate adapted to adjustably connect to a component of the prosthesis system adjacent a residual limb;

a lower plate below the upper plate and adapted to adjustably connect to the upper plate and to a shank or an other prosthetic device below the lower plate, wherein at least a portion of a bottom surface of the upper plate is convex and at least a portion of an upper surface of the lower plate is concave and adapted to receive at least part of the convex portion of the bottom surface of the upper plate; and a plurality of rocker bolt assemblies adapted to adjustably connect the lower plate to the upper plate, thereby providing for an adjustable connection between the component of the prosthesis system adjacent the residual limb and the shank or an other prosthetic device, whereby the adjustable connection provides for a concurrently made plurality of directional adjustments and/or angular adjustments of a position of the component of the prosthesis system relative to the shank or an other prosthetic device while the component of the prosthesis system is on the residual limb, wherein each rocker bolt assembly has a hollow threaded socket that extends downward through one of a plurality of apertures in the bottom surface of the upper plate and further downward through one of a plurality of adjacent corresponding apertures in the upper surface of the lower plate, the hollow threaded socket adapted to receive a threaded bolt.

* * * * *